(12) United States Patent
Thompson et al.

(10) Patent No.: US 10,941,379 B2
(45) Date of Patent: Mar. 9, 2021

(54) MICROBIAL SYSTEM FOR BIOSYNTHESIS OF NATURAL AND ENGINEERED PRODUCTS COUPLED TO IN SITU EXTRACTION IN SUPERCRITICAL $CO_2$

(71) Applicant: Massachusetts Institute of Technology, Cambridge, MA (US)

(72) Inventors: Janelle Renee Thompson, Cambridge, MA (US); Kyle C. Peet, Acton, MA (US); Adam J. E. Freedman, Cambridge, MA (US); Kristala Lanett Jones Prather, Milton, MA (US); Jason Thomas Boock, Dorchester, MA (US); Michael T. Timko, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 395 days.

(21) Appl. No.: 15/590,925

(22) Filed: May 9, 2017

(65) Prior Publication Data
US 2018/0119089 A1    May 3, 2018

Related U.S. Application Data

(60) Provisional application No. 62/423,187, filed on Nov. 16, 2016, provisional application No. 62/333,415, filed on May 9, 2016.

(51) Int. Cl.

| | |
|---|---|
| *C12N 1/32* | (2006.01) |
| *C12P 7/16* | (2006.01) |
| *C12P 7/22* | (2006.01) |
| *C12M 1/34* | (2006.01) |
| *C12N 1/20* | (2006.01) |
| *C12M 1/06* | (2006.01) |
| *C12N 9/88* | (2006.01) |
| *C12P 7/04* | (2006.01) |
| *C12M 1/00* | (2006.01) |
| *C12P 7/64* | (2006.01) |
| *C12Q 1/68* | (2018.01) |
| *C12R 1/07* | (2006.01) |
| *C12N 15/00* | (2006.01) |

(52) U.S. Cl.
CPC ............ *C12N 1/32* (2013.01); *C12M 1/06* (2013.01); *C12M 21/00* (2013.01); *C12M 41/40* (2013.01); *C12N 1/20* (2013.01); *C12N 9/88* (2013.01); *C12P 7/04* (2013.01); *C12P 7/16* (2013.01); *C12P 7/22* (2013.01); *C12P 7/6427* (2013.01); *C12P 7/6472* (2013.01); *C12Q 1/68* (2013.01); *C12R 1/07* (2013.01); *C12N 15/00* (2013.01); *Y02E 50/10* (2013.01); *Y02P 20/544* (2015.11)

(58) Field of Classification Search
None
See application file for complete search history.

(56) References Cited

U.S. PATENT DOCUMENTS 6,211,422 B1    4/2001    DeSimone et al.

OTHER PUBLICATIONS

Cody, R. et al Energy Analysis of Butanol Extraction Using Supercritical Carbon Dioxide WPI downloaded from https://digitalcommons.wpi.edu/cgi/viewcontent.cgi?article=4388&context=mqp-all Oct. 27, 2019.*
Branduardi, P. et al., Biotechnol Biofuels, 2013.*
Boock et al., Systems biology towards a continuous platform for biofuels production: Engineering an environmentally-isolated Bacillus strain for biofuel production and recovery under supercritical CO2. 2017 Genomic Sciences Program Annual PI meeting. Feb. 6-8, 2017. 315-316. Retrieved from https://www.orau.gov/gsp2017/2017-gsp-abstract-book.pdf on Jun. 28, 2017.
Branduardi et al., A novel pathway to produce butanol and isobutanol in *Saccharomyces cerevisiae*. Biotechnol Biofuels. May 4, 2013;6(1):68. doi: 10.1186/1754-6834-6-68.
Cody et al., Energy analysis of butanol extraction using supercritical carbon dioxide. Worchester Polytechnic Institute. Apr. 28, 2016. 1-44. Retrieved from https://web.wpi.edu/pubs/e-project/available/e-project-042816-040328/unrestricted/sc_butoh_extraction._rc.vs.hv_2016.pdf on Jun. 28, 2017.
Conlon et al., Extraction of bio-butanol using supercritical carbon dioxide. WPI. Apr. 2016. 1-67. Retrieved from https://web.wpi.edu/pubs/e-project/available/e-project-042816-093354/unrestricted/mqp_final_report.pdf on Jun. 28, 2017.
Dispirito et al., Semi-continuous extraction of bio-alcohols using supercritical carbon dioxide. WPI. Mar. 24, 2017. 1-89. Retrieved from https://web.wpi.edu/pubs/e-project/available/e-project-032317-124330/unrestricted/stolz_dispirito_mqp_report..pdf on Jun. 28, 2017.
Freedman et al., Systems biology towards a continuous platform for biofuels production: heterologous gene expression and isobutanol synthesis in B. megaterium SR7 and biofuel extraction under supercritical CO2. 2017 Genomic Sciences Program Annual PI meeting. Feb. 6-8, 2017. 317-318. Retrieved from https://www.orau.gov/gsp2017/2017-gsp-abstract-book.pdf on Jun. 28, 2017.
Freedman, Surveying and harnessing the genetic, (meta)genomic, and metabolic potential of the deep carbonated biosphere. MIT. Jun. 7, 2016. 1-190. Retrieved from https://dspace.mit.edu/handle/1721.1/104482 on Jun. 28, 2017.
Korneli et al., Getting the big beast to work—systems biotechnology of Bacillus megaterium for novel high-value proteins. J Biotechnol. Jan. 20, 2013;163(2):87-96. doi:10.1016/j.jbiotec.2012.06.018. Epub Jun. 28, 2012.
Marriott, Green extraction, separation and reactions using liquid or supercritical C02. Botanix Ltd. 2015. 1-36. Retrieved from https://www.york.ac.uk/res/gcrn/presentations/ray%20marriott%20-%20botanix.pdf. On Jun. 28, 2017.
Peet et al., Draft Genome Sequences of Supercritical $CO_2$-Tolerant Bacteria Bacillus subterraneus MITOT1 and Bacillus cereus MIT0214. Genome Announc. Apr. 9, 2015;3(2). pii: e00140-15. doi: 10.1128/genomeA.00140-15.

(Continued)

*Primary Examiner* — Heidi Reese
(74) *Attorney, Agent, or Firm* — Wolf, Greenfield & Sacks, P.C.

(57) ABSTRACT

Provided herein are methods of producing a bioproduct by culturing a cell in a multiphase reactor that comprises supercritical $CO_2$, near critical $CO_2$, or liquid $CO_2$.

8 Claims, 36 Drawing Sheets

Specification includes a Sequence Listing.

(56) References Cited

OTHER PUBLICATIONS

Peet et al., Microbial growth under supercritical $CO_2$. Appl Environ Microbiol. Apr. 2015;81(8):2881-92. doi: 10.1128/AEM.03162-14. Epub Feb. 13, 2015.
Peet, Demonstrating biocompatibility with supercritical $CO_2$: Biphasic cultivation of *Bacillus* spp. and probing acclimation mechanisms through proteome and lipid analysis. MIT. May 5, 2015. 1-152. Retrieved from https://dspace.mit.edu/handle/1721.1/97795#filesarea. On Jun. 28, 2017.
Sheppard et al., Retro-biosynthetic screening of a modular pathway design achieves selective route for microbial synthesis of 4-methylpentanol. Nat Commun. Sep. 24, 2014;5:5031. doi: 10.1038/ncomms6031.
Veettil et al., Can microbially derived advanced biofuels ever compete with conventional bioethanol? A critical review. Bioresources. Sep. 28, 2016;11:10711-10755.
[No Author Listed], Erpetoichthys calabaricus chromosome 10, fErpCal1.1, whole genome shotgun sequence. RefSeq No. NC_041403.1. NCBI. 1 page.
Anbu et al., Formations of Calcium Carbonate Minerals by Bacteria and Its Multiple Applications. Springerplus. Mar. 1, 2016;5:250, 26 pages. doi: 10.1186/s40064-016-1869-2. eCollection 2016.
Arioli et al., Carbamoylphosphate Synthetase Activity Is Essential for the Optimal Growth of *Streptococcus thermophilus* in Milk. J Appl Microbiol. Jul. 2009;107(1):348-54. doi: 10.1111/j.1365-2672.2009.04213.x. Epub Mar. 16, 2009.
Atsumi et al., Engineering the Isobutanol Biosynthetic Pathway in *Escherichia coli* by Comparison of Three Aldehyde Reductase/Alcohol Dehydrogenase Genes. Appl Microbiol Biotechnol. Jan. 2010;85(3):651-7. doi: 10.1007/s00253-009-2085-6. Epub Jul. 16, 2009.
Aziz et al., The Rast Server: Rapid Annotations Using Subsystems Technology. BMC Genomics. Feb. 8, 2008;9:75. doi: 10.1186/1471-2164-9-75.
Baier et al., Fluorescence-Based Methods for the Detection of Pressure-Induced Spore Germination and Inactivation. High Pressure Research. 2010;31:110-5.
Baines et al., The Long-Term Fate of CO2 in the Subsurface: Natural Analogues for CO2 Storage. Geological Society London Special Publ. Jan. 2004;233(1):59-85.
Barker et al., Experimental Observations of the Effects of Bacteria on Aluminosilicate Weathering. American Mineralogist.1998;83:1551-63.
Biddle et al., Metagenomic Signatures of the Peru Margin Subseafloor Biosphere Show a Genetically Distinct Environment. PNAS USA. Jul. 29, 2008;105(30):10583-8. doi: 10.1073/pnas.0709942105. Epub Jul. 23, 2008.
Biedendieck et al., Metabolic Engineering of Cobalamin (Vitamin B12) Production in Bacillus Megaterium. Microb Biotechnol. Jan. 2010;3(1):24-37. doi: 10.1111/j.1751-7915.2009.00125.x. Epub Jun. 10, 2009.
Boone et al., Diffusion of the Interspecies Electron Carriers H2 and Formate in Methanogenic Ecosystems and Its Implications in the Measurement of Km for H2 or Formate Uptake. Appl Environ Microbiol. Jul. 1989; 55(7): 1735-1741.
Brock et al., Thermus Aquaticus Gen. N. and Sp. N., a Nonsporulating Extreme Thermophile. J Bacteriol. Apr. 1969;98(1):289-97.
Brockman et al., Dynamic Metabolic Engineering: New Strategies for Developing Responsive Cell Factories. Biotechnol J. Sep. 2015;10(9):1360-9. doi: 10.1002/biot.201400422. Epub Apr. 13, 2015.
Budisa et al., Supercritical Carbon Dioxide and Its Potential as a Life-Sustaining Solvent in a Planetary Environment. Life (Basel). Aug. 8, 2014;4(3):331-40. doi: 10.3390/life4030331.
Buerger et al., Microbial Scout Hypothesis, Stochastic Exit from Dormancy, and the Nature of Slow Growers. Appl Environ Microbiol. May 2012;78(9):3221-8.
Cappa et al., Carbon Dioxide in Mississippian Rocks of the Paradox Basin and Adjacent Areas, Colorado, Utah, New Mexico, and Arizona. edited by 2000-H U.S. Geological Survey Bulletin. 1995. 30 pages.
Carlson et al., Comparison of Denitrification by Pseudomonas Stutzeri, Pseudomonas Aeruginosa, and Paracoccus Denitrificans. Appl Environ Microbiol. Apr. 1983; 45(4): 1247-1253.
Carver et al., Act: The Artemis Comparison Tool. Bioinformatics. Aug. 15, 2005;21(16):3422-3. Epub Jun. 23, 2005.
Chien et al., Deoxyribonucleic Acid Polymerase from the Extreme Thermophile Thermus Aquaticus. J Bacteriol. Sep. 1976;127(3):1550-7.
Cody et al., Energy analysis of butanol extraction using supercritical carbon dioxide. Worchester Polytechnic Institute. Aug. 4, 2016. 1-44. Retrieved from https://web.wpi.edu/pubs/eproject/available/e-project-042816040328/unrestricted/sc_butoh_extraction._rc.vs.hv_2016.pdf on Jun. 28, 2017.
Connor et al., 3-Methyl-1-Butanol Production in *Escherichia coli*: Random Mutagenesis and Two-Phase Fermentation. Appl Microbiol Biotechnol. Apr. 2010;86(4):1155-64. doi: 10.1007/s00253-009-2401-1. Epub Jan. 14, 2010.
Coppi et al., Development of a Genetic System for Geobacter Sulfurreducens. Appl Environ Microbiol. Jul. 2001;67(7):3180-7.
Cronin et al., The Use of Flow Cytometry to Study the Germination of Bacillus Cereus Endospores.Cytometry A. Mar. 2007;71(3):143-53.
Crump et al., Bacterioplankton Community Shifts in an Arctic Lake Correlate with Seasonal Changes in Organic Matter Source. Appl Environ Microbiol. Apr. 2003;69(4):2253-68.
Cunliffe, Correlating Carbon Monoxide Oxidation with Cox Genes in the Abundant Marine Roseobacter Clade. ISME J. Apr. 2011;5(4):685-91. doi: 10.1038/ismej.2010.170. Epub Nov. 11, 2010.
Cunningham et al., Microbially Enhanced Geologic Containment of Sequestered Supercritical CO2. Energy Procedia. 2009:3245-52.
Dinneen, Today in Energy: U.S. fuel ethanol production continues to grow into 2017. EIA. Retrieved from: https://www.eia.gov/conference/2008/conf_pdfs/Tuesday/Dinneen. Accessed 2007.
Eichler et al., Oxidation of Primary Aliphatic Alcohols by Acetobacterium *Carbinolicum* Sp. Nov., a Homoacetogenic Anaerobe. Archives of Microbiology. 1984;140:147-52.
El-Tarabily et al., Isolation and Characterisation of Sulfur-Oxidising Bacteria, Including Strains of Rhizobium, from Calcareous Sandy Soils and Their Effects on Nutrient Uptake and Growth of Maize (*Zea mays* L.). Australian Journal of Agricultural Research. 2006;57:101-11.
Emerson et al., Metagenomic Analysis of a High Carbon Dioxide Subsurface Microbial Community Populated by Chemolithoautotrophs and Bacteria and Archaea from Candidate Phyla. Environ Microbiol. Jun. 2016;18(6):1686-703. doi: 10.1111/1462-2920.12817. Epub Apr. 8, 2015.
Engelhardt et al., Biogeography of Rhizobium Radiobacter and Distribution of Associated Temperate Phages in Deep Subseafloor Sediments.ISME J. Jan. 2013;7(1):199-209. doi: 10.1038/ismej.2012.92. Epub Aug. 2, 2012.
Eppinger et al., Genome Sequences of the Biotechnologically Important Bacillus Megaterium Strains Qm B1551 and Dsm319. J Bacteriol. Aug. 2011;193(16):4199-213. doi: 10.1128/JB.00449-11. Epub Jun. 24, 2011.
Fernandes et al., Denitrification: An Important Pathway for Nitrous Oxide Production in Tropical Mangrove Sediments (Goa, India). Journal of Environmental Quality. Jul. 2010;39:1507-16.
Finster et al., *Sulfurospirillum arcachonense* Sp. Nov., a New Microaerophilic Sulfur-Reducing Bacterium. International Journal of Systematic and Evolutionary Microbiology. 1997;47(4):1212-17.
Gagen et al., Functional Gene Analysis Suggests Different Acetogen Populations in the Bovine Rumen and Tammar Wallaby Forestomach. Applied and Environmental Microbiology. 2010;76(23):7785-95.
Gaidenko et al., General Stress Transcription Factor Simgab and Sporulation Transcription Factor Sigmah Each Contribute to Survival of Bacillus Subtilis under Extreme Growth Condtions. J Bacteriol. Jul. 1998;180(14):3730-3.
Gao et al., Spatial Isolation and Environmental Factors Drive Distinct Bacterial and Archaeal Communities in Different Types of Petroleum Reservoirs in China. Sci Rep. Feb. 3, 2016;6:20174, 12 pages. doi: 10.1038/srep20174.

(56) References Cited

OTHER PUBLICATIONS

Ghosh et al., Isolation and Characterization of Superdormant Spores of *bacillus* Species. J Bacteriol. Mar. 2009;191(6):1787-97. doi: 10.1128/JB.01668-08. Epub Jan. 9, 2009.
Gilfillan et al., The Noble Gas Geochemistry of Natural CO2 Gas Reservoirs from the Colorado Plateau and Rocky Mountain Provinces, USA. Geochimica et Cosmochimica Acta. 2008;72(4):1174-98.
Grigoriev, Analyzing Genomes with Cumulative Skew Diagrams. Nucleic Acids Res. May 15, 1998;26(10):2286-90.
Hamady et al., Fast Unifrac: Facilitating High-Throughput Phylogenetic Analyses of Microbial Communities Including Analysis of Pyrosequencing and Phylochip Data. ISME J. Jan. 2010;4(1):17-27. doi: 10.1038/ismej.2009.97. Epub Aug. 27, 2009.
Hartman et al., Structure, Function, Regulation and Assembly of D-Ribulose-1,5-Bisphosphate Carboxylase/Oxygenase. Annual Review of Biochemistry. 1994;63:197-234.
Haszeldine et al., Natural Geochemical Analogues for Carbon Dioxide Storage in Deep Geological Porous Reservoirs, a United Kingdom Perspective. Oil and Gas Science and Technology. 2005;60(1): 33-49.
Holloway et al., Review of Natural CO2 Occurrences and Their Relevance to CO2 Storage. edited by International Energy Agency. Sep. 2005 124 pages.
Hu et al., Metabolic Engineering of Methylobacterium Extorquens Am1 for 1-Butanol Production. Biotechnol Biofuels. Oct. 21, 2014;7(1):156. doi: 10.1186/s13068-014-0156-0. eCollection 2014.
Hubert et al., Oil Field Souring Control by Nitrate-Reducing Sulfurospirillum Spp. That Outcompete Sulfate-Reducing Bacteria for Organic Electron Donors. Applied and Environmental Microbiology. 2007;73: 2644-52.
John et al., Retentive Memory of Bacteria: Long-Term Regulation of Dehalorespiration in Sulfurospirillum Multivorans. J Bacteriol. Mar. 2009;191(5):1650-5. doi: 10.1128/JB.00597-08. Epub Dec. 19, 2008.
Johnson, Biodiversity and Ecology of Acidophilic Microorganisms. FEMS Microbiology Ecology. 1998;27: 307-17.
Katano et al., Complete Genome Sequence of Oscillibacter Valericigenes Sjm18-20t(=Nbrc 101213t). Stand Genomic Sci. Jul. 30, 2012;6(3):406-14. doi: 10.4056/sigs.2826118.
Kataoka et al., Development of Butanol-Tolerant Bacillus Subtilis Strain Grsw2-B1 as a Potential Bioproduction Host. AMB Express. May 30, 2011;1(1):10. doi: 10.1186/2191-0855-1-10.
Kharaka et al., Gas-Water-Rock Interactions in Frio Formation Following CO2 Injection: Implications for the Storage of Greenhouse Gases in Sedimentary Basins. Geology.2006;34: 577-80.
Kieft et al., Changes in Ester-Linked Phospholipid Fatty Acid Profiles of Subsurface Bacteria During Starvation and Desiccation in a Porous Medium. Appl Environ Microbiol. Sep. 1994;60(9):3292-9.
Klein et al., Cold Shock Response of Bacillus Subtilis: Isoleucine-Dependent Switch in the Fatty Acid Branching Pattern for Membrane Adaptation to Low Temperatures. J Bacteriol. Sep. 1999;181(17):5341-9.
Kopke et al., Clostridium Ljungdahlii Represents a Microbial Production Platform Based on Syngas. Proc Natl Acad Sci U S A. Jul. 20, 2010;107(29):13087-92. doi: 10.1073/pnas.1004716107. Epub Jul. 2, 2010.
Labelle et al., Influence of Acidic Ph on Hydrogen and Acetate Production by an Electrosynthetic Microbiome. Plos One. 2014;9(10):e109935, 10 pages.
Lal, Carbon Sequestration. Philosophical Transactions of the Royal Society B: Biological Sciences. 2008;363(1492):815-30.
Lam et al., Engineering Alcohol Tolerance in Yeast. Science. 2014;346:71-5.
Lee et al., *Desulfosporosinus youngiae* Sp. Nov., a Spore-Forming, Sulfate-Reducing Bacterium Isolated from a Constructed Wetland Treating Acid Mine Drainage. International Journal of Systematic and Evolutionary Microbiology. 2009;59:2743-46.

Levinson et al., Activation Energy for Glucose-Induced Germination of Bacillus Megaterium Spores. Journal of Bacteriology. 1970;103:269-70.
Liu et al., A Novel Arsenate Respiring Isolate That Can Utilize Aromatic Substrates. FEMS Microbial Ecology. 2004;48: 323-32.
Liu et al., Complete Genome Sequence of the Industrial Strain Bacillus Megaterium Wsh-002. J Bacteriol. Nov. 2011;193(22):6389-90. doi: 10.1128/JB.06066-11.
Lloyd et al., Microbial Transformations of Arsenic in the Environment: From Soda Lakes to Aquifers. Elements. 2006; 2: 85-90.
Magge et al., Analysis of Dye Binding by and Membrane Potential in Spores of *bacillus* Species. J Appl Microbiol. Mar. 2009;106(3):814-24. doi: 10.1111/j.1365-2672.2008.04048.x.
[No Author Listed], *Climate Change 2007: The Physical Science Basis*. IPCC. Cambridge, United Kingdom: Cambridge University Press, 2007. 1007 pages.
Albertsen et al., Genome sequences of rare, uncultured bacteria obtained by differential coverage binning of multiple metagenomes. Nat Biotechnol. Jun. 2013;31(6):533-8.
Allis et al., Natural CO2 Reservoirs on the Colorado Plateau and Southern Rocky Mountains: Candidates for CO2 Sequestration. Paper presented at the Proceedings of First National Conference on Carbon Sequestration. Washington, D.C. Jan. 2001.
Aloisi et al., Nucleation of Calcium Carbonate on Bacterial Nanoglobules. Geology. 2006;34(12):1017-20.
Atsumi et al., Metabolic engineering of *Escherichia coli* for 1-butanol production. Metab Eng. Nov. 2008;10(6):305-11.
Atsumi et al., Non-fermentative pathways for synthesis of branched-chain higher alcohols as biofuels. Nature. Jan. 3, 2008;451(7174):86-9.
Aziz et al., The RAST Server: rapid annotations using subsystems technology. BMC Genomics. Feb. 8, 2008;9:75.
Ballivet-Tkatchenko et al., Direct Synthesis of Dimethyl Carbonate with Supercritical Carbon Dioxide: Characterization of a Key Organotin Oxide Intermediate. Catalysis Today. Jun. 2006;115:80-7.
Bastian et al., Engineered ketol-acid reductoisomerase and alcohol dehydrogenase enable anaerobic 2-methylpropan-1-ol production at theoretical yield in *Escherichia coli*. Metab Eng. May 2011;13(3):345-52.
Beckman, A challenge for green chemistry: designing molecules that readily dissolve in carbon dioxide. Chem Commun (Camb). Sep. 7, 2004;(17):1885-8.
Booyaratanakornkit et al., Transcriptional responses of the deep-sea hyperthermophile Methanocaldococcus jannaschii under shifting extremes of temperature and pressure. Extremophiles. May 2007;11(3):495-503.
Braissant et al., Bacterially Induced Mineralization of Calcium Carbonate in Terrestrial Environments: The Role of Exopolysaccharides and Amino Acids. Journal of Sedimentary Research. 2003;73(3):485-90.
Buchfink et al., Fast and Sensitive Protein Alignment Using Diamond. Nature Methods. 2015;12:59-60.
Buday et al., Improved Acetone-Butanol Fermentation Analysis Using Subambient HPLC Column Temperature. Enzyme and Microbial Technology. Jan. 1990;12(1):24-7.
Chang et al., Arsenic in an as-Contaminated Abandoned Mine Was Mobilized from Fern-Rhizobium to Frond-Bacteria via the Ars Gene. Biotechnology and Bioprocess Engineering. Oct. 2010;15(5):862-73.
Chivian et al., Environmental genomics reveals a single-species ecosystem deep within Earth. Science. Oct. 10, 2008;322(5899):275-8.
Colwell et al., Microorganisms from Deep, High Temperature Sandstones: Constraints on Microbial Colonization. FEMS Microbial Ecology 20 (1997): 425-35.
Connor et al., Microbial production of advanced transportation fuels in non-natural hosts. Curr Opin Biotechnol. Jun. 2009;20(3):307-15.
David et al., Optimization of antibody fragment production in Bacillus megaterium: the role of metal ions on protein secretion. J Biotechnol. Oct. 1, 2010;150(1):115-24.

(56) References Cited

OTHER PUBLICATIONS

De Beer et al., Saturated CO2 Inhibits Microbial Processes in CO2-Vented Deep-Sea Sediments. Biogeosciences 10 (2013): 5639-49.
De Bok et al., Interspecies Electron Transfer in Methanogenic Propionate Degrading Consortia. Water Res. Mar. 2004;38(6):1368-75.
De La Plaza et al., Biochemical and Molecular Characterization of Alpha-Ketoisovalerate Decarboxylase, an Enzyme Involved in the Formation of Aldehydes from Amino Acids by Lactococcus Lactis. FEMS Microbiol Lett. Sep. 15, 2004;238(2):367-74.
Dodsworth et al., Ammonia oxidation, denitrification and dissimilatory nitrate reduction to ammonium in two US Great Basin hot springs with abundant ammonia-oxidizing archaea. Environ Microbiol. Aug. 2011;13(8):2371-86.
Edgar, Uparse: Highly Accurate OTU Sequences from Microbial Amplicon Reads. Nat Methods. Oct. 2013;10(10):996-8.
Ehrenberg et al., Plagioclase Dissolution Related to Biodegradation of Oil in Brent Group Sandstones (Middle Jurassic) of Gullfaks Field, Northern North Sea. Sedimentology 48 (2001): 703-22.
Eisenmann et al., Lithotrophic Growth of Sulfurospirillum Deleyianum with Sulfide as Electron Donor Coupled to Respiratory Reduction of Nitrate to Ammonia. Archives of Microbiology. 1995;164:180-85.
Ezeji et al., Acetone butanol ethanol (ABE) production from concentrated substrate: reduction in substrate inhibition by fed-batch technique and product inhibition by gas stripping. Appl Microbiol Biotechnol. Feb. 2004;63(6):653-8.
Ezeji et al., Achievements and perspectives to overcome the poor solvent resistance in acetone and butanol-producing microorganisms. Appl Microbiol Biotechnol. Feb. 2010;85(6):1697-712.
Ezeji et al., Bioproduction of butanol from biomass: from genes to bioreactors. Curr Opin Biotechnol. Jun. 2007;18(3):220-7.
Ferris et al., Synthesis of long prebiotic oligomers on mineral surfaces. Nature. May 2, 1996;381(6577):59-61.
Fischer et al., Selection and optimization of microbial hosts for biofuels production. Metab Eng. Nov. 2008;10(6):295-304.
Foster, When protons attack: microbial strategies of acid adaptation. Curr Opin Microbiol. Apr. 1999;2(2):170-4.
Gilfillan et al., Solubility trapping in formation water as dominant CO(2) sink in natural gas fields. Nature. Apr. 2, 2009;458(7238):614-8.
Goris et al., Insights into organohalide respiration and the versatile catabolism of Sulfurospirillum multivorans gained from comparative genomics and physiological studies. Environ Microbiol. Nov. 2014;16(11):3562-80.
Guerout-Fleury et al., Plasmids for ectopic integration in Bacillus subtilis. Gene. Nov. 21, 1996;180(1-2):57-61.
GVR. Isobutanol Market Analysis by Product (Synthetic, Bio-Based), Application (Oil & Gas, Solvents & Coatings, Chemical Intermediates) and Segment Forecasts to 2022. Isobutanol Market Size, Share—Global Industry Report, 2022. Edited by Grand View Research, 2015. 8 pages.
Hammond et al., Enzymatic-Reactions in Supercritical Gases. Applied Biochemistry and Biotechnology.1985;11:393-400.
Hattori et al., Involvement of formate as an interspecies electron carrier in a syntrophic acetate-oxidizing anaerobic microorganism in coculture with methanogens. J Biosci Bioeng. 2001;91(3):294-8.
Hyatt et al., Conditions affecting Bacillus megaterium spore germination in glucose or various nitrogenous compounds. J Bacteriol. Jun. 1962;83:1231-7.
Inui et al., Expression of Clostridium acetobutylicum butanol synthetic genes in Escherichia coli. Appl Microbiol Biotechnol. Jan. 2008;77(6):1305-16.
Irwin et al., Isotopic Evidence for Source of Diagenetic Carbonate Formed During the Burial of Organic Rich Sediments. Nature 269 (1977): 209-13.
Isenschmid et al., The influence of pressure and temperature of compressed CO2 on the survival of yeast cells. J Biotechnol. May 1, 1995;39(3):229-37.
Itavaara et al., Characterization of bacterial diversity to a depth of 1500 m in the Outokumpu deep borehole, Fennoscandian Shield. FEMS Microbiol Ecol. Aug. 2011;77(2):295-309.
Kaden et al., Cysteine-mediated electron transfer in syntrophic acetate oxidation by cocultures of Geobacter sulfurreducens and Wolinella succinogenes. Arch Microbiol. Jul. 2002;178(1):53-8.
Kawanami et al., Chemical Fixation of Carbon Dioxide to Styrene Carbonate under Supercritical Conditions with Dmf in the Absence of Any Additional Catalysts. Chemical Communication. 2000:2089-90.
Kelly et al., *The Prokaryotes a Handbook on the Biology of Bacteria. Third Edition*. Volume 2: Ecophysiology and Biochemistry. Springer, 2006. 1157 pages.
Khosravi-Darani et al., Application of supercritical fluid extraction in biotechnology. Crit Rev Biotechnol. Oct.-Dec. 2005;25(4):231-42.
Kim et al., A sporulation medium for Bacillus anthracis. J Appl Bacteriol. Jun. 1974;37(2):265-7.
Kirk, Variation in energy available to populations of subsurface anaerobes in response to geological carbon storage. Environ Sci Technol. Aug. 1, 2011;45(15):6676-82.
Knoshaug et al., Butanol tolerance in a selection of microorganisms. Appl Biochem Biotechnol. May 2009;153(1-3):13-20.
Knutson et al., Effect of Pressurized Solvents on Ethanol Production by the Thermophilic Bacterium Clostridium Thermocellum. Journal of Supercritical Fluids 16 (1999): 149-56.
Komlos et al., Biofilm Barriers to Contain and Degrade Dissolved Trichloroethylene. Environmental Progress 23 (2004): 69-77.
Laitinen et al., Supercritical Fluid Extraction of 1-Butanol from Aqueous Solutions. Journal of Supercritical Fluids 15 (1999): 245-52.
Lee et al., Isobutanol Production in Engineered *Saccharomyces cerevisiae* by Overexpression of 2-Ketoisovalerate Decarboxylase and Valine Biosynthetic Enzymes. Bioprocess and Biosystems Engineering. 2012;35(9):1467-75. DOI 10.1007/s00449-012-0736-y.
Lee et al., Mineralization of Gaseous CO2 by Bacillus Megaterium in Close Environment System. Water, Air, & Soil Pollution. 2014;225(1787):1-8. DOI 10.1007/s11270-013-1787-7.
Leitner, Supercritical Carbon Dioxide as a Green Reaction Medium for Catalysis. Accounts of Chemical Research. 2002;35(9): 746-56.
Letain et al., Development of a Genetic System for the Chemolithoautotrophic Bacterium Thiobacillus Denitrificans. Applied and Environmental Microbiology. 2007;73(10):3265-71.
Li et al., Engineering Bacillus Subtilis for Isobutanol Production by Heterologous Ehrlich Pathway Construction and the Biosynthetic 2-Ketoisovalerate Precursor Pathway Overexpression. Applied Microbiology and Biotechnology. 2011;91(3):577-89.
Liao et al., Effects of High-Pressure Carbon Dioxide on Proteins and DNA in *Escherichia coli*. Microbiology. 2011;157: 709-20. DOI 10.1099/mic.0.046623-0.
Liu et al., How Microbes Tolerate Ethanol and Butanol. New Biotechnology. 2009;26:117-21.
Magnuson et al., Reductive Dechlorination of Tetrachloroethene to Ethene by a Two-Component Enzyme Pathway. Applied and Environmental Microbiology. Apr. 1998;64(4):1270-75.
Malten et al., Production and Secretion of Recombinant Leuconostoc mesenteroides dextransucrase DsrS in Bacillus megaterium. Biotechnology and Bioengineering. 2005;89(2):206-18.
Marshall et al., Long-Term Operation of Microbial Electrosynthesis Systems Improves Acetate Production by Autotrophic Microbiomes. Environmental Science & Technology. 2013;47:6023-29.
Martens et al., Microbial Production of Vitamin B12. Applied and Environmental Microbiology. 2002;58(3):275-85.
Martin-Galiano et al., The Promoter of the Operon Encoding the F0f1 Atpase of *Streptococcus pneumoniae* Is Inducible by Ph. Molecular Microbiology. 2001;41(6):1327-38.
Marty et al., Kinetics of Lipase-Catalyzed Esterification in Supercritical CO2. Biotechnology and Bioengineering. 1992;39(3):273-80.
Mascia et al., End-to-End Continuous Manufacturing of Pharmaceuticals: Integrated Synthesis, Purification, and Final Dosage Formation. Angewandte Chemie International Edition. 2013;52:12359-63.

(56) References Cited

OTHER PUBLICATIONS

Matsuda et al., Alcohol Dehydrogenase Is Active in Supercritical Carbon Dioxide. Chemical Communications. 2000;15:1367-68.
Matsuda et al., Biocatalysis in Supercritical CO2. Current Organic Chemistry. 2005;9:299-315.
Matsuda et al., Conversion of Pyrrole to Pyrrole-2-Carboxylate by Cells of Bacillus Megaterium in Supercritical CO2. Chemical Communications. 2001;1(21):2194-95.
Matsuda et al., Enzymatic Reactions in Supercritical CO2: Carboxylation, Asymmetric Reduction and Esterification. Catalysis Today. 2004; 96:103-11.
Matsuda et al., Novel Continuous Carboxylation Using Pressurized Carbon Dioxide by Immobilized Decarboxylase. Tetrahedron Letters. 2008;49:6019-20.
Mitchell et al., Biofilm Enhanced Geologic Sequestration of Supercritical CO2. International Journal of Greenhouse Gas Control. 2009;3: 90-99.
Mitchell et al., Resilience of Planktonic and Biofilm Cultures to Supercritical CO2. The Journal of Supercritical Fluids. 2008;47: 318-25.
Mizrahi-Man et al., Taxonomic Classification of Bacterial 16s Rrna Genes Using Short Sequencing Reads: Evaluation of Effective Study Designs. Plos One. 2013;8(1):e53608.
Moro et al., Transformation of Bacillus Megaterium by Electroporation. Biotechnology Techniques. 1995;9(8): 589-90.
Morozova et al., CO2SINK Group. Monitoring of the Microbial Community Composition in Deep Subsurface Saline Aquifers During CO2 Storage in Ketzin, Germany. Energy Procedia. 2011;4:4362-70.
Morozova et al., Monitoring of the Microbial Community Composition of the Saline Aquifers During CO2 Storage by Fluorescence in Situ Hybridisation. International Journal of Greenhouse Gas Control. 2010;4(6): 981-89.
Morris et al., Microbial Syntrophy: Interaction for the Common Good. FEMS Microbiol Ecology. 2013;37(3):384-406.
Mu et al., Changes in the Deep Subsurface Microbial Biosphere Resulting from a Field-Scale CO2 Geosequestration Experiment. Frontiers in Microbiology. May 2014; 5(209): 1-11.
Mukhopadhyay et al., Salt Stress in Desulfovibrio Vulgaris Hildenborough: An Integrated Genomics Approach. Journal of Bacteriology. Jun. 2006;188(11): 4068-78.
Nakamura et al., Lipase Activity and Stability in Supercritical Carbon Dioxide. Chemical Engineering Communications. 1986;45: 207-12.
Nakayama et al., Complete Genome of a Nonphotosynthetic Cyanobacterium in a Diatom Reveals Recent Adaptations to an Intracellular Lifestyle. Proceedings of the National Academy of Sciences of the United States of America. 2014;111(31): 11407-12.
Nedwell et al., Hydrogen as an Electron Donor for Sulfate-Reducing Bacteria in Slurries of Salt Marsh Sediment. Microbial Ecology. 1981;7(4):305-13.
NETL, Carbon Dioxide Enhanced Oil Recovery: Untapped Domestic Energy Supply and Long Term Carbon Storage Solution. US Department of Energy, National Energy Technology Laboratory. 2010:1-32.
Nielsen et al., Engineering Alternative Butanol Production Platforms in Heterologous Bacteria. Metabolic Engineering. 2009;11:262-73.
Nigam et al., Production of Liquid Biofuels from Renewable Resources. Progress in Energy and Combustion Science. 2011; 37:52-68.
Ogasawara et al., Novel Regulation Targets of the Metal-Response Bass-Basr Two-Component System of *Escherichia coli*. Microbiology. 2012;158:1482-92.
Onstott, Impact of CO2 Injections on Deep Subsurface Microbial Ecosystems and Potential Ramifications for the Surface Biosphere. In: Carbon Dioxide Capture for Storage in Deep Geologic Formations, vol. 2. 2005. Thomas et al., Eds. Chapter 30:1217-1250.

Oppermann et al., Soil Microbial Community Changes as a Result of Long-Term Exposure to a Natural CO2 Vent. Geochimica et Cosmochimica Acta. 2010;74(9):2697-716.
Orr, Onshore Geologic Storage of CO2. Science. Sep. 25, 2009;325:1656-58.
Ortuño et al., Supercritical Carbon Dioxide Inactivation of *Escherichia coli* and *Saccharomyces cerevisiae* in Different Growth Stages. The Journal of Supercritical Fluids. 2012;63: 8-15.
Oudshoorn, Recovery of Bio-Based Butanol. Technische Universiteit Delft. 2012. ISBN 978-90-5335-561-9.
Oulé et al., *Escherichia coli* Inactivation Mechanism by Pressurized CO2. Canadian Journal of Microbiology. 2006;52:1208-17.
Oulé et al., Microbial Effect of Pressurized CO2 and the Influence of Sensitizing Additives. European Journal of Scientific Research. 2010;41(4):569-81.
Pham et al., Characterizing Microbial Diversity in Production Water from an Alaskan Mesothermic Petroleum Reservoir with Two Independent Molecular Methods. Environmental Microbiology. 2009;11(1):176-87.
Phelps et al., Comparison between Geochemical and Biological Estimates of Subsurface Microbial Activities. Microbial Ecology. 1994; 28(3):335-49.
Poechlauer et al., Continuous Processing in the Manufacture of Active Pharmaceutical Ingredients and Finished Dosage Forms: An Industry Perspective. Organic Process Research & Development. 2012;16:1586-90.
Preheim et al., Distribution-Based Clustering: Using Ecology to Refine the Operational Taxonomic Unit. Applied and Environmental Microbiology. Nov. 2013;79(21):6593-603.
Quast et al., The Silva Ribosomal RNA Gene Database Project: Improved Data Processing and Web-Based Tools. Nucleic Acids Research. 2013; 41:D590-D596.
Rabinowitz et al., Reasonable, Foreseeable Development: Oil, Natural Gas, and Carbon Dioxide in Canyons of the Ancients National Monument. San Juan Public Lands Center Bureau of Land Management. Apr. 2005; 1-66.
Rastogi et al., Microbial and Mineralogical Characterizations of Soils Collected from the Deep Biosphere of the Former Homestake Gold Mine, South Dakota. Microbial Ecology. 2010; 60(3):539-50.
Richard et al., *Escherichia coli* Glutamate- and Arginine-Dependent Acid Resistance Systems Increase Internal Ph and Reverse Transmembrane Potential. Journal of Bacteriology. Sep. 2004;186:6032-6041.
Richhardt et al., An Improved Transconjugation Protocol for Bacillus Megaterium Facilitating a Direct Genetic Knockout. Applied Microbiology and Biotechnology. 2010; 86:1959-65.
Roberge et al., Microreactor Technology: A Revolution for the Fine Chemical and Pharmaceutical Industries?. Chemical Engineering & Technology. 2005;28(3): 318-23.
Rodriguez-Contreras et al., High Production of Poly(3-Hydroxybutyrate) from a Wild Bacillus Megaterium Bolivian Strain. Journal of Applied Microbiology. 2013; 114: 1378-87.
Romão et al., Characterization of the [Nife] Hydrogenase from the Sulfate Reducer Desulfovibrio Vulgaris Hildenborough. Biochemical and Biophysical Research Communications. 1997;240: 75-79.
Roseboom et al., The Active Site of the [Fefe]-Hydrogenase from Desulfovibrio Desulfuricans. Ii. Redox Properties, Light Sensitivity and Co-Ligand Exchange as Observed by Infrared Spectroscopy. Journal of Biological Inorganic Chemistry. 2006;11:102-18.
Roth et al., Germination of Spores of Certain Aerobic Bacilli under Anaerobic Conditions. J Bacteriol. Jun. 24, 1955;71:162-6.
Sabirzyanov et al., Solubility of Water in Supercritical Carbon Dioxide. High Temp. 2002;40(2):231-4.
Salgin et al., The Enantioselective Hydrolysis of Racemic Naproxen Methyl Ester in Supercritical CO2 Using Candida Rugosa Lipase. J Supercrit Fluids. 2007;43:310-6.
Salter et al., Reagent Contamination Can Critically Impact Sequence-Based Microbiome Analyses. BMC Biol. 2014;12:87, 12 pages.
Santillan et al., Isolation and Characterization of a CO2-Tolerant Lactobacillus Strain from Crystal Geyser, Utah, U.S.A. Front Earth Sci. Jul. 23, 2015;3:41, 11 pages.

(56) References Cited

OTHER PUBLICATIONS

Santos et al., Siderophore Production by Bacillus Megaterium: Effect of Growth Phase and Cultural Conditions. App Biochem Biotechnol. 2014;172:549-60. Epub 3012 Oct. 8.
Seo et al., The Application of a Mulch Biofilm Barrier for Surfactant Enhanced Polycyclic Aromatic Hydrocarbon Bioremediation. Environ Poll. 2009;157:95-101.
Setlow et al., Role of Dipicolinic Acid in Resistance and Stability of Spores of Bacillus Subtilis with or without DNA-Protective Alpha/Beta-Type Small Acid-Soluble Proteins. J Bacteriol. Jun. 2006;188(11):3740-7.
Setlow, Spore Germination. Curr Opin Microbiol. 2003;6:550-56.
Setlow, Spores of Bacillus Subtilis: Their Resistance to and Killing by Radiation, Heat and Chemicals. J App Microbiol. 2006;101:514-25.
Sinclair et al., Microbial Community Composition and Diversity via 16s rRNA Gene Amplicons: Evaluating the Illumina Platform. Plos One. Feb. 3, 2015;10:e0116955, 18 page.
Smith et al., Correlation of Carbon Dioxide Abundance with Temperature in Clastic Hydrocarbon Reservoirs: Relationship to Inorganic Chemical Equilibrium. Marine Petroleum Geology. May 1989;6:129-35.
Smith et al., Prokaryotic Carbonic Anhydrases. FEMS Microbial Ecology. 2000;24(4):335-66.
Solomon et al., A Dynamic Metabolite Valve for the Control of Central Carbon Metabolism. Metabol Engin. 2012;124:661-71.
Sowden et al., Carbonylation of Methanol in Supercritical CO2 Catalysed by a Supported Rhodium Complex. Chem Commun. 1999:2511-12.
Spilimbergo et al., Non-Thermal Bacteria Inactivation with Dense CO2. Biotechnol Bioengin. Oct. 7, 2003;84:627-38.
Spilimbergo et al., Real-Time Monitoring of Cell Membrane Modification During Supercritical CO2 Pasteurization. J Supercrit Fluids. 2009;48:93-7.
SRES. Emissions Scenarios: A Special Report of Working Group III. Intergovernmental Panel on Climate Change. Cambridge, United Kingdom, 2000. 27 pages.
Steen et al., Metabolic Engineering of *Saccharomyces cerevisiae* for the Production of N-Butanol. Microbial Cell Factories. Dec. 3, 2008;7:36, 8 pages.
Stevens et al., Natural Analogs for Geologic Storage of CO2: An Integrated Global Research Program. First National Conference on Carbon Sequestration. U.S. Department of Energy, National Energy Technology Laboratory. Washington, D.C. 2001. 12 pages.
Stolz et al., *Sulfurospirillum barnesii* Sp. Nov. and *Sulfurospirillum arsenophilum* Sp. Nov., New Members of the Sulfurospirillum Clade of the Epsilon Proteobacteria. Int J Sys Evol Microbiol. 1999;49:1177-80.
Suess et al., Widespread Distribution of Rhizobium Radiobacter in Mediterranean Sediments. Dept Earth Sci. Cardiff University, Wales UK. ISSM 2005. 1 page.
Sugimura et al., Electrochemical Fixation of Carbon Dioxide in Oxoglutaric Acid Using an Enzyme as an Electrocatalyst. J Am Chem Soc. 1989;111:2361-62.
Sugimura et al., Electrochemical Fixation of Carbon Dioxide in Pyruvic Acid to Yield Malic Acid Using Malic Enzyme as an Electrocatalyst. J Electroanalyt Chem. 1990;299:241-7.
Sulzenbacher et al., Crystal Structure of *E. coli* Alcohol Dehydrogenase Yqhd: Evidence of a Covalently Modified Nadp Coenzyme. J Mol Biol. 2004;342:489-502.
Szulczewski et al., Lifetime of Carbon Capture and Storage as a Climate-Change Mitigation Technology. PNAS. Apr. 3, 2012;109(14):5185-9.
Takai et al., Cell Proliferation at 122 Degrees C and Isotopically Heavy Ch4 Production by a Hyperthermophilic Methanogen under High-Pressure Cultivation. PNAS. Aug. 5, 2008;105(31):10949-54.
Tan et al., Draft Genome Sequences of Campylobacterales (Epsilonproteobacteria) Obtained from Methanogenic Oil Sands Tailings Pond Metagenomes. Genome Announcements. Sep. 2014;2(5):e01034-14, 2 pages.
Timko et al., Partition Coefficients of Organic Solutes between Supercritical Carbon Dioxide and Water: Experimental Measurements and Empirical Correlations. J Chem Eng Data. 2004;49:768-78.
Timoteo et al., Desulfovibrio Vulgaris Bacterioferritin Uses H2O2 as a Co-Substrate for Iron Oxidation and Reveals Dps-Like DNA Protection and Binding Activities. Biochem J. 2012;446:125-33.
Turner et al., Investigating Deep Phylogenetic Relationships among Cyanobacteria and Plastids by Small Subunit rRNA Sequence Analysis. J Eukary Microbiol. 1999;46:327-38.
Ulmer et al., Effect of Compressed Gases on the High Pressure Inactivation of Lactobacillus Plantarum Tmw 1.460. Prog Biotechnol. 2002;19:317-24.
Van Ooij et al., Subcellular Localization of a Small Sporulation Protein in Bacillus Subtilis. J Bacteriol. Feb. 2003;185(4):1391-8.
Vane, Separation Technologies for the Recovery and Dehydration of Alcohols from Fermentation Broths. Biofuels Bioprod Bioref. Oct. 21, 2008;2:553-88. doi: 10.1002/bbb.
Vary et al., Bacillus Megaterium—from Simple Soil Bacterium to Industrial Protein Production Host. App Microbiol Biotechnol. 2007;76:957-67.
Vary, Germination of Bacillus Megaterium Spores after Various Extraction Procedures. J Bacteriol. Nov. 1973;116(2):797-802.
Vary, Prime Time for Bacillus Megaterium. Microbiol. 1994;140:1001-13.
Wang et al., Naïve Bayesian Classifier for Rapid Assignment of Rrna Sequences into the New Bacterial Taxonomy. App Environ Microbiol. Aug. 2007;73(16):5261-7.
Wei et al., Superdormant Spores of *bacillus* Species Germinate Normally with High Pressure, Peptidoglycan Fragments, and Bryostatin. J Bacteriol. Mar. 2010;192(5):1455-58.
West et al., Potential Impact of CO2 Storage on Subsurface Microbial Ecosystems and Implications for Groundwater Quality. Energy Procedia. 2011;4:3163-70.
White et al., Effective Terminal Sterilization Using Supercritical Carbon Dioxide. J Biotechnol. 2006;123:504-15.
Wieser et al., Carbon Dioxide Fixation by Reversible Pyrrole-2-Carboxylate Decarboxylase from Bacillus Megaterium Pyr2910. J Mol Catalysis B Enzymatic.1998;257:495-9.
Wimmer et al., Review on the Effects of Supercritical Carbon Dioxide on Enzyme Activity. Int J Syst Mol Sci. Jan. 19, 2010;11(1):233-53.
Xiong et al., Recent Advances in the Discovery and Development of Marine Microbial Natural Products. Marine Drugs. 2013;11:700-17.
Yanagawa et al., Metabolically Active Microbial Communities in Marine Sediment under High-CO2 and Low-pH Extremes. ISME J. 2012;7:555-67.
Yang et al., Effect of Carbon Source, C/N Ratio, Nitrate and Dissolved Oxygen Concentration on Nitrite and Ammonium Production from Denitrification Process by Pseudomonas Stutzeri D6. Biores Technol. 2012;104:65-72.
Yardley, *An Introduction to Metamorphic Petrology*. Longman Earth Sci Series. Prentice Hall. 1989. 131 pages.
Yoshida et al., Catalytic Production of Urethanes from Amines and Alkyl Halides in Supercritical Carbon Dioxide. Chem Commun. 2000:151-2.
Yu et al., Development of a Genetic System for the Deep-Sea Psychrophilic Bacterium *Pseudoalteromonas* Sp. Sm9913. Microbial Cell Fact. 2014;13:13, 9 pages.
Zamarreno et al., Carbonate Crystals Precipitated by Freshwater Bacteria and Their Use as a Limestone Consolidant. App Environ Microbiol. Sep. 2009;75(18):5981-90.
Zhang et al., Microbial Diversity in Long-Term Water-Flooded Oil Reservoirs with Different in Situ Temperatures in China. Sci Reports. 2012;2:1-10.
Zhang et al., Sterilization Using High-Pressure Carbon Dioxide. J Supercrit Fluids. 2006;38:354-72.
Zhuang et al., Incomplete Wood-Ljungdahl Pathway Facilitates One-Carbon Metabolism in Organohalide-Respiring Dehalococcoides Mccartyi. PNAS. 2014;111(17):6419-24.

* cited by examiner

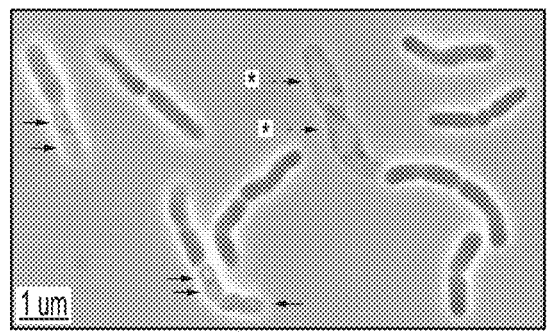 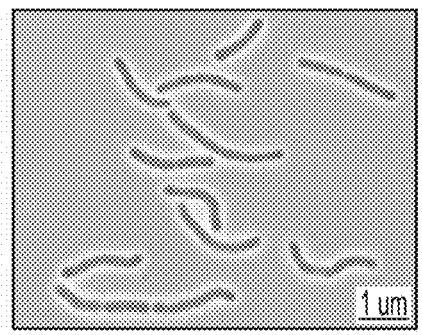
FIG. 9A  FIG. 9B
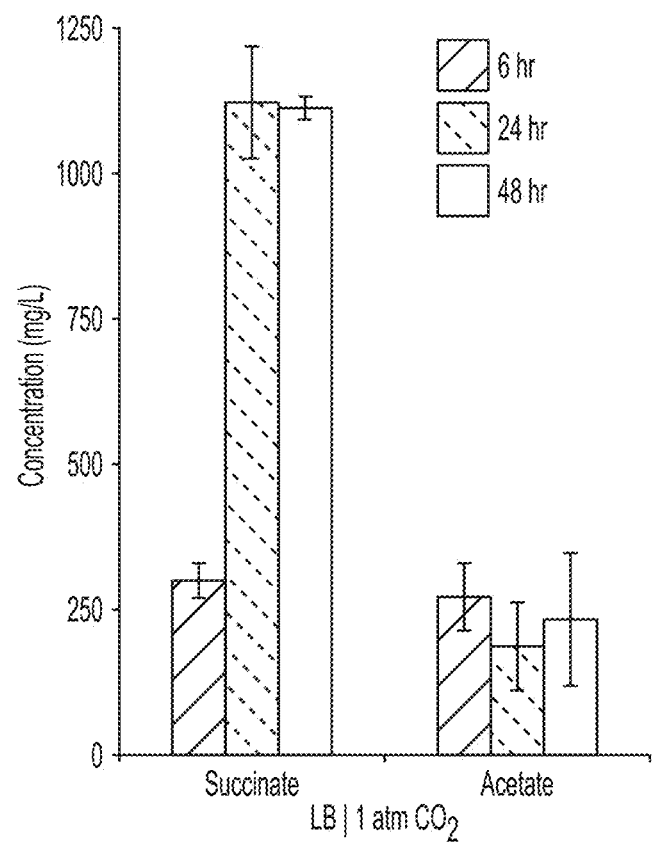
FIG. 10A

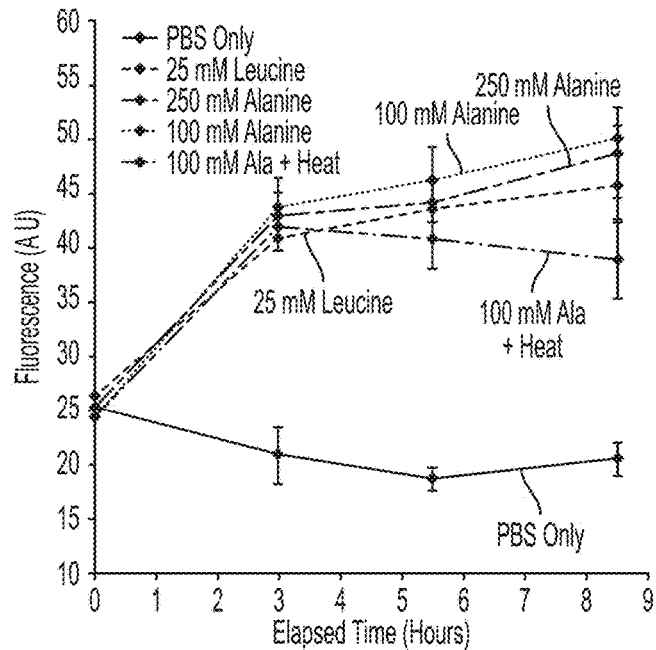
FIG. 12B
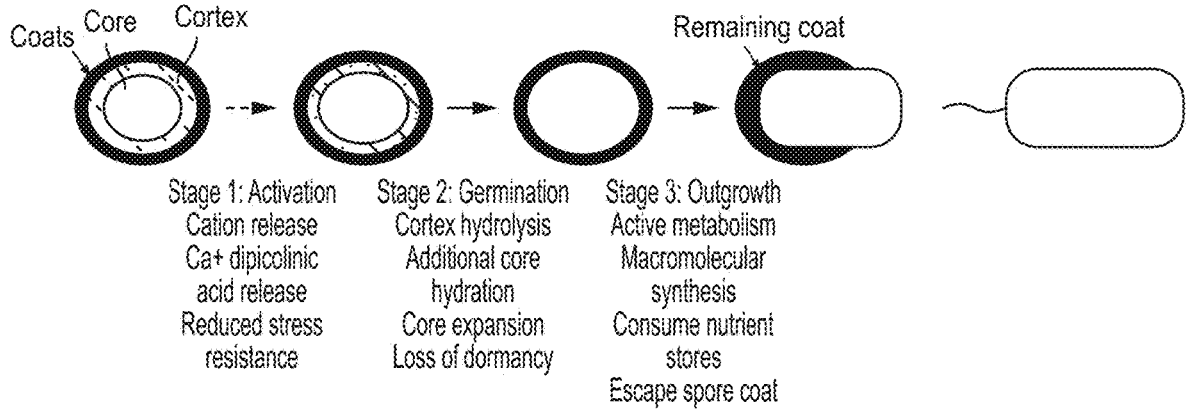
FIG. 13A
| Classification | FCM Fluorescence | DNA Strain Distribution | Physiological State |
|---|---|---|---|
| "Dormant" | Low | Edge-localized | Intact Spore |
| "Activated" | Medium | Center-localized | Stage 1-2 |
| "Germinated" | High | Whole cell | Stage 2-3 |
FIG. 13B

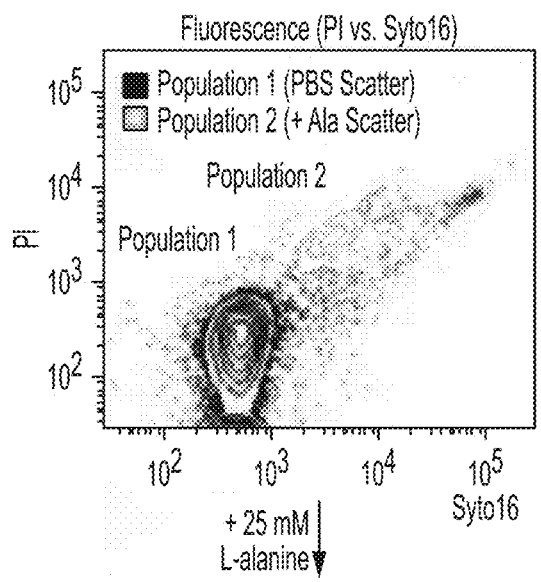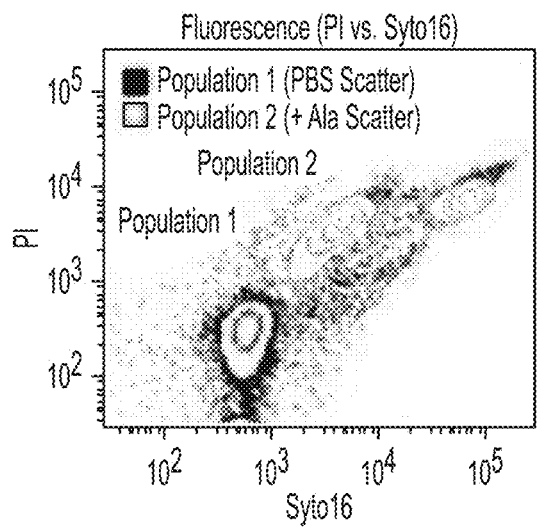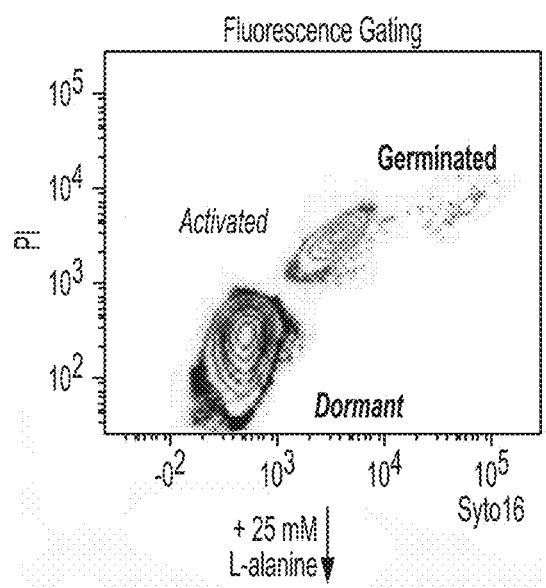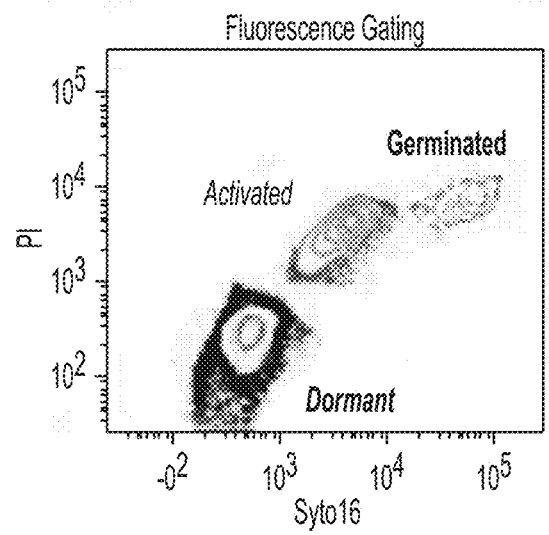
FIG. 14A	FIG. 14B

SEQUENCE LISTING

```
<160> NUMBER OF SEQ ID NOS: 22

<210> SEQ ID NO 1
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 1
gtgccagcmg ccgcggtaa                                             19

<210> SEQ ID NO 2
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 2
ggttaccttg ttacgactt                                             19

<210> SEQ ID NO 3
<211> LENGTH: 35
<212> TYPE: DNA
```

```
<213> ORGANISM: Artificial Sequence
<220> FEATURE:
<223> OTHER INFORMATION: Synthetic polynucleotide

<400> SEQUENCE: 3
gtccaaacta gtaccatgat tacggattca ctggc                                35

<210> SEQ ID NO 4
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 4
ccgccggcat gctcattatt tttgacacca gaccaactgg                            40

<210> SEQ ID NO 5
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 5
cggcggcacc tcgctaac                                                   18

<210> SEQ ID NO 6
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 6
ggtgcctcac tgattaagca ttgg                                            24

<210> SEQ ID NO 7
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 7
ccaatgctta atcagtgagg cacc                                            24

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
agatccacag gacgggtgtg                                                 20

<210> SEQ ID NO 9
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 9
cacacccgtc ctgtggatct gactctctag cttgaggcat c                         41
```

<210> SEQ ID NO 10
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 10
gttagcgagg tgccgccggg atcctaactc acattaattg cg                42

<210> SEQ ID NO 11
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 11
agcttagtcg acagggggaa atgtacaatg accatgatta cggattcact ggc     53

<210> SEQ ID NO 12
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 12
gtccaaacta gtatgtatac agtaggagat tacctattag accg              44

<210> SEQ ID NO 13
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 13
gaggagcatg cgagctcgga tcctcattat gatttatttt gttcagcaaa tagttaccc   59

<210> SEQ ID NO 14
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 14
gaggagggat cctcgacagg gggaaatgta caatgagcta cccggaaaag ttcg    54

<210> SEQ ID NO 15
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 15
ccgccggcat gcaatgcggc cgctcattag tcgctgaatt ctttatcgta accaacc    57

<210> SEQ ID NO 16
<211> LENGTH: 58
<212> TYPE: DNA
<213> ORGANISM: Artificial Sequence
<220> FEATURE:

<223> OTHER INFORMATION: Synthetic polynucleotide

<400> SEQUENCE: 16

```
taatgaggat cctcgacagg gggaaatgta caaatgaaca actttaatct gcacaccc      58
```

<210> SEQ ID NO 17
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 17

```
gcatgcaatg cggccgctca ttagcgggcg gcttcgtata tac                      43
```

<210> SEQ ID NO 18
<211> LENGTH: 1486
<212> TYPE: DNA
<213> ORGANISM: B. megaterium

<400> SEQUENCE: 18

```
gatgaacgct ggcggcgtgc ctaatacatg caagtcgagc gaactgatta gaagcttgct      60
tctatgacgt tagcggcgga cgggtgagta acacgtgggc aacctgcctg tgagactggg     120
ataacttcgg gaaaccgaag ctaataccgg ataggatctt ctccttcatg ggagatgatt     180
gaaagatggt ttcggctatc acttacagat gggcccgcgg tgcattagct agttggtgag     240
gtaacggctc accaaggcaa cgatgcatag ccgacctgag agggtgatcg ccacactgg      300
gactgagaca cggcccagac tcctacggga ggcagcagta gggaatcttc cgcaatggac     360
gaaagtctga cggagcaacg ccgcgtgagt gatgaaggct ttcgggtcgt aaaactctgt     420
tgttagggaa gaacaagtac gagagtaact gctcgtacct tgacggtacc taaccagaaa     480
gccacggcta actacgtgcc agcagccgcg gtaatacgta ggtggcaagc gttatccgga     540
attattgggc gtaaagcgcg cgcaggcggt tcttaagtc tgatgtgaaa gcccacggct      600
caaccgtgga gggtcattgg aaactgggga acttgagtgc agaagagaaa agcggaattc     660
cacgtgtagc ggtgaaatgc gtagagatgt ggaggaacac cagtggcgaa ggcggctttt     720
tggtctgtaa ctgacgctga ggcgcgaaag cgtggggagc aaacaggatt agatacctg     780
gtagtccacg ccgtaaacga tgagtgctaa gtgttagagg gtttccgccc tttagtgctg     840
cagctaacgc attaagcact ccgcctgggg agtacggtcg caagactgaa actcaaagga     900
attgacgggg gcccgcacaa gcggtggagc atgtggttta attcgaagca acgcgaagaa     960
ccttaccagg tcttgacatc ctctgacaac tctagagata gagcgttccc cttcggggga    1020
cagagtgaca ggtggtgcat ggttgtcgtc agctcgtgtc gtgagatgtt gggttaagtc    1080
ccgcaacgag cgcaacccctt gatcttagtt gccagcattt agttgggcac tctaaggtga    1140
ctgccggtga caaaccggag gaaggtgggg atgacgtcaa atcatcatgc cccttatgac    1200
ctgggctaca cacgtgctac aatggatggt acaaagggct gcaagaccgc gaggtcaagc    1260
caatcccata aaaccattct cagttcggat tgtaggctgc aactcgccta tatgaagctg    1320
gaatcgctag taatcgcgga tcagcatgcc gcggtgaata cgttcccggg ccttgtacac    1380
accgcccgtc acaccacgag agtttgtaac acccgaagtc ggtggagtaa ccgtaaggag    1440
ctagccgcct aaggtgggac agatgattgg ggtgaagtcg taacaa                   1486
```

<210> SEQ ID NO 19
<211> LENGTH: 1545

```
<212> TYPE: DNA
<213> ORGANISM: B. licheniformis

<400> SEQUENCE: 19
agagtttgat cctggctcag gacgaacgct ggcggcgtgc ctaatacatg caagtcgagc      60
ggaccgacgg gagcttgctc ccttaggtca gcggcggacg ggtgagtaac acgtgggtaa     120
cctgcctgta agactgggat aactccggga aaccggggct aataccggat gcttgattga     180
accgcatggt tcaatcataa aaggtggctt ttagctacca cttacagatg gacccgcggc     240
gcattagcta gttggtgagg taacggctca ccaaggcgac gatgcgtagc cgacctgaga     300
gggtgatcgg ccacactggg actgagacac ggcccagact cctacgggag gcagcagtag     360
ggaatcttcc gcaatggacg aaagtctgac ggagcaacgc cgcgtgagtg atgaaggttt     420
tcggatcgta aaactctgtt gttagggaag aacaagtacc gttcgaatag ggcggcacct     480
tgacggtacc taaccagaaa gccacggcta actacgtgcc agcagccgcg gtaatacgta     540
ggtggcaagc gttgtccgga attattgggc gtaaagcgcg cgcaggcggt ttcttaagtc     600
tgatgtgaaa gcccccggct caaccgggga gggtcattgg aaactgggga acttgagtgc     660
agaagaggag agtggaattc cacgtgtagc ggtgaaatgc gtagagatgt ggaggaacac     720
cagtggcgaa ggcgactctc tggtctgtaa ctgacgctga ggcgcgaaag cgtggggagc     780
gaacaggatt agataccctg gtagtccacg ccgtaaacga tgagtgctaa gtgttagagg     840
gtttccgccc tttagtgctg cagcaaacgc attaagcact ccgcctgggg agtacggtcg     900
caagactgaa actcaaagga attgacgggg cccgcacaa gcggtggagc atgtggttta     960
attcgaagca acgcgaagaa ccttaccagg tcttgacatc ctctgacaac cctagagata    1020
gggcttcccc ttcgggggca gagtgacagg tggtgcatgg ttgtcgtcag ctcgtgtcgt    1080
gagatgttgg gttaagtccc gcaacgagcg caacccttga tcttagttgc cagcattcag    1140
ttgggcactc taaggtgact gccggtgaca aaccggagga aggtggggat gacgtcaaat    1200
catcatgccc cttatgacct gggctacaca cgtgctacaa tgggcagaac aaagggcagc    1260
gaagccgcga ggctaagcca atcccacaaa tctgttctca gttcggatcg cagtctgcaa    1320
ctcgactgcg tgaagctgga atcgctagta atcgcggatc agcatgccgc ggtgaatacg    1380
ttcccgggcc ttgtacacac cgcccgtcac accacgagag tttgtaacac ccgaagtcgg    1440
tgaggtaacc ttttggagcc agccgccgaa ggtgggacag atgattgggg tgaagtcgta    1500
acaaggtagc cgtatcggaa ggtgcggctg gatcacctcc tttct                    1545

<210> SEQ ID NO 20
<211> LENGTH: 546
<212> TYPE: DNA
<213> ORGANISM: B. megaterium

<400> SEQUENCE: 20
atgagtcaac cagctgtagc caagcgctat gcactagctc tttttcaatt agcaacagaa      60
aaacagatga tcgatgaaat gcaagaccag ctacaaatcg ttgaagaggt gtttgctaaa     120
acacctgaat taatggatgt attaactcat ccaaaaatta caattgagcg aaaaaaacag     180
tttgtaagtg aggcatttgc tgaactttca ccaactgttc aacatacggt tcttctatta     240
ttagagcgtc accgcattca aattgttagc caaatggtac aagagtatcg tttcctagcg     300
aacgaagtac gtggcgtggc agatgcaact gtttattctg tcaaaccttt aagcgcagat     360
gagaaaagag caatctcgca atcatttgct tcaaaagttg gaaaacatac gttaaatatt     420
```

```
tcaaatgtag tagataaaag cctaatcggc ggcgtgaagc ttcgcattgg taatcgtatc    480
tatgatggca gcattagcag caaattagaa acgatccacc gaggacttct tgcacacaga    540
tcgtag                                                                546
```

<210> SEQ ID NO 21
<211> LENGTH: 960
<212> TYPE: DNA
<213> ORGANISM: B. megaterium

<400> SEQUENCE: 21

```
atggctcctg tgcgtcaagc tttaaaagat gcaggtcttt ctgcaagcga acttgataaa     60
gtaatcttag ttggtggttc aactcgtatc ccagcggtac aagatgcaat caaaaaagaa    120
actggtcaag atcctcataa aggtgtaaat cctgatgaag tagttgcact tggtgcagca    180
attcaaggtg gcgtgttaac tggtgatgta aaagacgttg tattactaga cgtaacgcct    240
ttatcactag gtatcgaaac aatgggtggc gtatttacaa agctaattga gcgtaatacg    300
acaattccaa caagtaaatc acaagtattc tcaacggctg cagatagcca aacagctgta    360
gatattcacg ttcttcaagg tgagcgccca atgtctgcag acaacaaaac gctaggacgt    420
ttccaattaa cagacattcc tcctgcacca cgcggagtac ctcaaatcga gtatcattc     480 gatattgata agaatggtat cgtaaacgtt cgtgcaaaag atttaggtac aaacaaagag    540
caggctatta caattaaatc ttcaactggt ttatcagatg acgaaatcga ccgcatggta    600
aaagaagcgg aagaaacgc agatgctgat aagcaacgta agaagaagt ggaactacgc      660 aacgaagcag atcaattagt gttcacaact gaaaaaacat aaaagatct tgaaggaaaa     720 gtagaagaag ctgaagtaac aaaagctaac gaagcaaaag atgctttaaa agctgcgatt    780
gaaaagaatg accttgaaga atcaaagcg aaaaagatg aacttcaaga atcgttcaa       840 gcgttaactg taaaattgta tgagcaagct caacaagctc agcaagcagg tgaacaaggc    900
gctcaaaatg atgatgttgt agatgcagag tttgaggaag taaacgacga caaaaaataa    960
```

<210> SEQ ID NO 22
<211> LENGTH: 1632
<212> TYPE: DNA
<213> ORGANISM: B. megaterium

<400> SEQUENCE: 22

```
atggcaaaag acattaaatt tagcgaagaa gcacgtcgcg caatgctacg tggtgtagat     60
acattggcaa atgctgtaaa agtaacgctt ggaccaaaag tcgtaacgt tgtattagaa     120 aagaaattcg gttcaccgct tattacaaat gatggtgtaa caattgcaaa agaaatcgaa    180
ttagaagacg catttgaaaa catgggtgct aaattagtag ccgaggttgc tagcaaaaca    240
aacgacgttg ctggtgacgg tacaactact gcaacagttt tagcgcaagc aatgatcaga    300
gaaggtctta aaacgtaac ggctggtgct aacccaatgg gtatccgtaa aggtatggaa      360
aaagcagtag ctgtagcggt tgaagaacta aaagcaatct ctaaaccaat tcaaggtaaa    420
gattcaattg ctcaagtagc ggctatctca gcagctgacg aagaagtagg tcaactaatc    480
gctgaagcaa tggagcgcgt tggtaacgac ggcgttatca cacttgaaga atcaaaaggt    540
ttcacaactg aattagaagt ggtagaaggt atgcagtttg accgtggata tgcatctcct    600
tacatggtaa ctgattcaga taaaatggaa gctgtattag atgatccata catcttaatc    660
acagacaaaa aaatcgttaa gattgaagaa atccttaccgg tattagagca agttgttcaa    720
caaggcaagc ctctattaat catcgctgaa gacgtagaag gcgaagcttt agcaacatta    780
```

```
gttgtgaaca aacttcgtgg tacatttaca gctgtagctg ttaaagctcc tggttttggt    840
gatcgtcgta aagcaatgct acaagacgtt gcgatcttaa caggcggaga agtaatcact    900
gaagagcttg gtcttgactt aaaaacagca ggcatcgatc aattaggtcg cgcttctaaa    960
attgttgtaa caaaagaaaa tacaacagtt gtaaacggtg caggaaacgc agaagatatc   1020
ctagcacgcg taaaccaaat caaagctcag cttgaagaaa caacttcaga gtttgaccgt   1080
gaaaaattac aagagcgctt agcaaaactt gctggtggcg tagctgtaat caaagttggt   1140
gcggcaactg aaactgagtt aaaagaacgt aaattacgta ttgaagatgc attaaactct   1200
acgcgtgctg cggttgaaga aggtatcgta gctggtggtg gtactgcatt agtaaatatc   1260
tataataaag tagcaagcat cgaagctgac ggtgacactg ctacaggtat caacatcgta   1320
ttacgtgcga ttgaagagcc tgtacgtcaa atcgctcaca atgctggttt agaaggatca   1380
gtaatcgttg agcgtctaaa aggcgaagca gttggaactg gattcaacgc tgcaactggc   1440
gagtgggtaa atatgctaga cactggtatc gttgacccaa caaaagtaac gcgttcagct   1500
cttcaaaatg cttcttctgt agcggctatg ttcttaacaa ctgaagcagt tgttgctgac   1560
aagccagaag aaggcggagc acctgcaatg cctgacatgg gcggcatggg tggaatgggc   1620
ggcatgatgt aa                                                      1632
```

MICROBIAL SYSTEM FOR BIOSYNTHESIS OF NATURAL AND ENGINEERED PRODUCTS COUPLED TO IN SITU EXTRACTION IN SUPERCRITICAL $CO_2$

RELATED APPLICATIONS

This application claims the benefit under 35 U.S.C. § 119(e) of U.S. provisional application No. 62/423,187, filed Nov. 16, 2016 and U.S. provisional application No. 62/333,415, filed May 9, 2016, each of which is incorporated by reference herein in its entirety.

GOVERNMENT SUPPORT

This invention was made with government support under Grant Nos. DE-SC0012555 and DE-FE0002128 awarded by the Department of Energy. The government has certain rights in the invention.

FIELD OF INVENTION

The invention relates to methods of producing a bioproduct involving culturing a cell in a multiphase reactor comprising a solvent phase comprising supercritical $CO_2$, near critical $CO_2$, or liquid $CO_2$.

BACKGROUND

Supercritical carbon dioxide ($scCO_2$) is generally regarded as a sterilizing agent of vegetative cells and a high-level disinfectant of most bacterial endospores (White et al., 2006; Ortuño et al., 2012, Mitchell et al., 2008, Zhang et al., 2006). When $scCO_2$ is introduced to a system, significant pH decreases (e.g., to pH~3 in unbuffered systems, pH~5-6 in buffered systems) occur on a timescale of several days (Kharaka et al., 2006). Because of these properties, $scCO_2$ has been studied within the context of sterilization for the food and drug industries.

SUMMARY OF THE INVENTION

Aspects of the present disclosure provide methods of producing a bioproduct, comprising culturing a cell in a multiphase reactor comprising an aqueous phase and a solvent phase, wherein the solvent phase comprises supercritical $CO_2$ ($scCO_2$), near critical $CO_2$, or liquid $CO_2$. In some embodiments, the cell is a viable cell. In some embodiments, the solvent phase comprises $scCO_2$. In some embodiments, the solvent phase comprises near critical $CO_2$. In some embodiments, the solvent phase comprises liquid $CO_2$. In some embodiments, the cell is a bacterial cell. In some embodiments, the bacterial cell is resistant to $scCO_2$. In some embodiments, the bacterial cell is a spore-forming bacterium belonging to the genus *Firmicutes*. In some embodiments, the bacterial cell is a *Bacillus* spp. In some embodiments, the bacterial cell is selected from the group consisting of *Bacillus cereus, Bacillus subterraneus, Bacillus amyloliquefaciens, Bacillus safensis, Bacillus lichenformis*, and *Bacillus megaterium*. In some embodiments, the bacterial cell is *Bacillus megaterium* SR7.

In some embodiments, the cell is in spore-form or has been acclimated to $scCO_2$. In some embodiments, the cell has been acclimated to $scCO_2$ by previous exposure to $scCO_2$.

In some embodiments, the bioproduct is selected from the group consisting of isobutantol, butanol, isopentanol, phenyl-ethyl-alcohol and 4-methyl-pentanol. In some embodiments, the cell is engineered to recombinantly express one or more genes. In some embodiments, the bioproduct is partitioned into $scCO_2$, near critical $CO_2$, or liquid $CO_2$. In some embodiments, the bioproduct is a hydrocarbon, oxygenated hydrocarbon, aldehyde, alcohol, fatty acid, or ketone. In some embodiments, the bioproduct is isobutanol and the cell is engineered to recombinantly express an isoketovalerate decarboxylase and an alcohol dehydrogenase. In some embodiments, the isoketovalerate decarboxylase is a *Lactococcus lactis* gene. In some embodiments, the alcohol dehydrogenase is an *E. coli* gene. In some embodiments, the bioproduct is 4-methyl-pentanol and the cell is engineered to recombinantly express one or more enzymes selected from the group consisting of an acetolactate synthase, a ketol-acid reductoisomerase, a dihydroxy-acid dehydratase, an alpha-ketoisovalerate decarboxylase, an aldehyde dehydrogenase, a propionyl-CoA transferase, a beta-keto-thiolase, a beta-keto-acyl-CoA reductase, an enoyl-CoA hydratase, a trans-enoyl-CoA reductase, a carboxylic acid reductase, a 4'-phosphopantenheinyl transferase, and an alcohol dehydrogenase.

In some embodiments, the bioproduct is isolated from the solvent phase. In some embodiments, the bioproduct is isolated from the aqueous phase. In some embodiments, the solvent phase further comprises less than or equal to about 3% inert helium. In some embodiments, the aqueous phase comprises a growth media. In some embodiments, the growth media comprises a spore germination inducer. In some embodiments, the spore germination inducer is D-alanine.

In some embodiments, the culturing comprises incubating the cell in the multiphase reactor for at least 5 hours. In some embodiments, the culturing comprises incubating the cell in the multiphase reaction at a temperature between 35° C.-40° C.

Other aspects provide a *Bacillus megaterium* cell that recombinantly expresses an isoketovalerate decarboxylase and an alcohol dehydrogenase. In some embodiments, the cell is a *Bacillus megaterium* SR7 cell.

Yet other aspects provide a reactor comprising (a) (i) supercritical $CO_2$ or a mixture of supercritical $CO_2$ and one or more other solvents, (ii) near critical $CO_2$ or a mixture of near critical $CO_2$ and one or more other solvents, or (iii) liquid $CO_2$ or a mixture of near critical $CO_2$ and one or more other solvents; and (b) at least one viable cell. In some embodiments, the viable cell is a bacterial cell. In some embodiments, the bacterial cell is resistant to $scCO_2$. In some embodiments, the bacterial cell is a spore-forming bacterium belonging to the genus *Firmicutes*. In some embodiments, the bacterial cell is a *Bacillus* spp. In some embodiments, the bacterial cell is selected from the group consisting of *Bacillus cereus, Bacillus subterraneus, Bacillus amyloliquefaciens, Bacillus safensis, Bacillus lichenformis*, and *Bacillus megaterium*. In some embodiments, the bacterial cell is *Bacillus megaterium* SR7.

In some embodiments, the viable cell is in spore-form or has been acclimated to $scCO_2$. In some embodiments, the viable cell has been acclimated to $scCO_2$ by previous exposure to $scCO_2$. In some embodiments, the viable cell is engineered to recombinantly express one or more genes.

In some embodiments, the reactor further comprises a bioproduct. In some embodiments, the bioproduct is partitioned into the $scCO_2$, near critical $CO_2$, or liquid $CO_2$. In some embodiments, the bioproduct is a hydrocarbon, oxygenated hydrocarbon, aldehyde, alcohol, fatty acid, or ketone. In some embodiments, the bioproduct is selected from the group consisting of isobutantol, butanol, isopentanol, phenyl-ethyl-alcohol and 4-methyl-pentanol. In some embodiments, the bioproduct is isobutanol and the viable cell is engineered to recombinantly express an isoketovalerate decarboxylase and an alcohol dehydrogenase. In some embodiments, the isoketovalerate decarboxylase is a *Lactococcus lactis* gene. In some embodiments, the alcohol dehydrogenase is an *E. coli* gene. In some embodiments, the bioproduct is 4-methyl-pentanol and the cell is engineered to recombinantly express. In some embodiments, the bioproduct is isolated from the $scCO_2$ phase.

In some embodiments, the reactor comprises one or more other solvent, wherein the one or more other solvent is inert helium. In some embodiments, the reactor further comprises a growth media. In some embodiments, the growth media comprises a spore germination inducer. In some embodiments, the spore germination inducer is D-alanine.

These and other aspects of the invention, as well as various embodiments thereof, will become more apparent in reference to the drawings and detailed description of the invention. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF THE DRAWINGS

The accompanying drawings are not intended to be drawn to scale. For purposes of clarity, not every component may be labeled in every drawing. In the drawings:

FIGS. 9A and 9B show phase contrast light microscopy of SR7 vegetative cultures. PHB-filled (bright cells, black arrow) and membrane-degraded SR7 cells (transparent, gray arrows with asterisk) in glucose-amended LB grown under 1 atm $CO_2$ (FIG. 9A). Cells grown in LB under 1 atm $CO_2$ without glucose accumulate observable, but smaller amounts of PHB granules, often distributed at the cellular poles (FIG. 9B).

FIGS. 10A and 10B show the concentration of *B. megaterium* SR7 fermentation products produced under 1 atm $CO_2$ in LB medium (FIG. 10A) and M9+ medium (FIG. 10B) as detected and measured by HPLC. The columns are, from left to right, samples obtained at 6 hours, 24 hours, and 48 hours.

FIGS. 12A and 12B show assays tracking the extent of population-level germination progress in PBS buffer by cell stain pattern by fluorescence microscopy (FIG. 12A) and culture bulk fluorescence (FIG. 12B).

FIGS. 13A and 13B show a schematic illustrating the physiological process of endospore germination (FIG. 13A) and the defining traits and hypothesized corresponding physiological state of three detected spore populations (FIG. 13B).

FIGS. 14A-14D show flow cytometry results. FIG. 14A shows fluorescence distribution of all counts previously gated by side/forward scatter gates. FIG. 14B shows a subset of those counts were then gated by GFP and PI fluorescence intensity (low/dormant; intermediate/activated; high/germinated. FIG. 14C shows the distribution and intensity of Syto16 fluorescence in Population 1 and FIG. 14D shows the same in Population 2. The top panel shows SR7 spores incubated in PBS and the bottom panel shows SR7 spores incubated in PBS amended with 25 mM L-alanine.

FIG. 26A shows production of isobutyraldehyde by SR7 pXyl $kivD_{L1}$ and in tandem with one of five alcohol dehydrogenase variants after 4 hours. FIG. 26B shows production of isobutanol by SR7 pXyl $kivD_{L1}$ and in tandem with one of five alcohol dehydrogenase variants after 24 hours. The columns in FIGS. 26A and 26B are, from left to right: KivD only, KivD $ADH6_{Sc}$, KivD $AdhA_{L1}$, KivD $AdhP_{Ec}$, KivD $YqhD_{Ec}$, KivD $AdhA_{Bm}$. FIG. 26C shows production of isobutanol and isopentanol using SR7 strains expressing a partial or full isobutanol pathway. For each strain, the left column represents the isobutanol titer and the right column represents the isopentanol titer. FIG. 26D shows production of isobutanol and isopentanol by a SR7 strain containing a redesigned full isobutanol pathway resulting in an increase in the conversion of isobutanol to isopentanol. For each bioproduct, the left column represents the titer when cultured in the presence of 10 g/L glucose, and the right column represents the titer when cultured in the presence of 25 g/L glucose.

FIG. 29A shows total titers and FIG. 29B shows filter count-normalized per cell metabolite productivity. Final cell concentrations for each sample are listed at the right. No metabolites were detected in media-only reactors and reactors without cell growth.

FIG. 38A shows a schematic for butanol extraction. FIG. 38B shows an energy consumption for butanol extraction using $scCO_2$.

DETAILED DESCRIPTION OF SOME EMBODIMENTS

Figure 1:
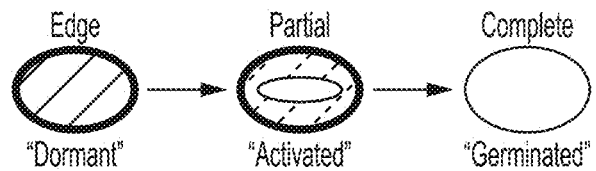
FIG. 1 shows the expected and observed DNA staining patterns of differentially germinated *Bacillus megaterium* (*B. megaterium*) SR7 spores.

Described herein are methods of producing bioproducts by culturing cells in a multiphase reactor in which the solvent phase comprises supercritical $CO_2$ ($scCO_2$), near critical $CO_2$, or liquid $CO_2$. Also provided herein are cells, including cells that have been genetically engineered to express heterologous enzymes and produce bioproducts, and reactors for use in the methods described herein. The invention is based, at least in part, on the identification and isolation of microorganisms that are resistant to $scCO_2$ and are capable of replicating and producing bioproducts when cultured in the presence of $scCO_2$. Although $scCO_2$ is frequently used as a solvent for compound extraction and in vitro biocatalysis, it is considered to be inaccessible for in vivo microbial bioproduct stripping due to lethal effects on microorganisms. Therefore, the methods described herein unexpectedly provide active bioproduct synthesis and extraction in a $scCO_2$-exposed multiphase reactor. As liquid $CO_2$ and near critical $CO_2$ have similar solvation strength as $scCO_2$, liquid $CO_2$, and near critical $CO_2$ may alternatively be used in the solvent phase.

In vivo bioproduct production using $scCO_2$ provides a number of benefits, including: reducing contamination in the reactor as $scCO_2$ is toxic to the majority of microorganisms; providing a high concentration reactant for $CO_2$ consuming reactions; relieving end product toxicity effects by in situ extraction (stripping); and alleviating the need for additional product dehydration due to the desiccating effects of $scCO_2$. Additionally, $scCO_2$ may be decanted from the culture, leaving the bioproducts at a high concentration.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations of thereof herein, is meant to encompass the items listed thereafter and equivalents thereof as well as additional items.

The methods described herein involve culturing a cell (or population of cells) in a multiphase reactor comprising an aqueous phase and a solvent phase, which comprises supercritical $CO_2$, near critical $CO_2$, or liquid $CO_2$. As used herein, the term "supercritical $CO_2$" or "$scCO_2$" refers to carbon dioxide ($CO_2$) that is maintained in a state above its critical temperature and critical pressure. For example, supercritical $CO_2$ may be maintained at a temperature of at least about 31° C. and a pressure of at least 72.8 atm.

The presence of $scCO_2$ may acidify the environment (culture) as well as introduce a range of potentially toxic stresses on microbial cells. Due to its predominantly non-polar solvent chemistry, $scCO_2$ penetrates bacterial cell walls and membranes, extracting fatty acids, lipids, and other intracellular materials that preferentially partition into the $scCO_2$ from the cytosol (Ulmer et al., 2002). Inside the cell, $scCO_2$ may decrease intracellular pH, disable enzymes, disrupt protein synthesis, and cause cellular desiccation, ultimately resulting in cell death (Spilimbergo and Bertucco, 2003; Kirk, 2011; Zhang et al., 2006).

As used herein, the term "near critical $CO_2$" refers to carbon dioxide ($CO_2$) that is maintained in a state that is substantially near the critical point (near the critical temperature and critical pressure).

As also used herein, the term "liquid $CO_2$" references to carbon dioxide ($CO_2$) that is maintained in the liquid state.

In some embodiments, the cells that are cultured under $scCO_2$, near critical $CO_2$, or liquid $CO_2$ headspace are viable cells, meaning the cells are metabolically active. In some embodiments, the cells are bacterial cells. In some embodiments the cells are resistant to $scCO_2$, near critical $CO_2$, or liquid $CO_2$. As used herein, a cell is considered to be "resistant" to $scCO_2$ if the cell experiences fewer deleterious effects upon exposure to $scCO_2$ than other cells. In some embodiments, a population of cells that is resistant to $scCO_2$ undergoes less cell death than cells in a population of cells that are not resistant to $scCO_2$. Alternatively or in addition, a cell that is resistant to $scCO_2$ may be described as being "tolerant" to $scCO_2$.

Cells that are resistant to $scCO_2$ may exhibit any of a number of characteristics that may provide for the resistance to $scCO_2$ and/or may employ any adaptive mechanism to defend against the lethal effects of $scCO_2$. For example, the rigidity of gram-positive cell walls afforded by dense layers of peptidoglycan (comprising up to 90% of the thickness) may confer enhanced tolerance to exposure by reducing the rate of $scCO_2$ penetration into the cell (Oulé et al., 2010). Examples of adaptive mechanisms used by cells in the presence of $scCO_2$ to maintain viability include the dense matrix of extrapolymeric substances (EPS) composed of carboxylic acids, polysaccharides, amino acids, and other components that are commonly found in biofilms, thought to limit $scCO_2$ cellular envelope penetration through chemical interaction with $CO_2$ (Mitchell et al., 2008; Braissant et al., 2003); modifications of microbial membrane structure (e.g., branching and chain length, fatty acid saturation) which may enable a cell to calibrate its membrane fluidity and permeability in response to solvent, environmental and nutrient conditions (Spilimbergo et al., 2009; Isenschmid et al., 1995; Mitchell et al., 2008; Spilimbergo and Bertucco, 2003; Klein et al., 1999; Mangelsdorf et al., 2009; Kieft et al., 1994; Mukhopadhyay et al., 2006); and expression of alternative transcription factors which trigger the general stress response, acid stress response, and sporulation cascade, each of which induces physiological adaptations to offset $scCO_2$-related stresses (Ogasawara et al., 2012; Liao et al., 2011; Martin-Galiano et al., 2001; Richard and Foster, 2004; Foster, 1999; Gaidenko and Price, 1998).

Peet et al., (2015) investigated the extent to which $scCO_2$-resistant *Bacillus* strains alter their protein expression and cell wall and membrane compositions in response to culturing under headspaces of 1 and 100 atm of $CO_2$ and $N_2$. Changes in the proteomic profiles of cells when exposed to $scCO_2$ may indicate that $scCO_2$ acclimation can be induced or enhanced, for example, by acclimating a cell to $scCO_2$ prior to inoculation of a culture (media) or reactor comprising $scCO_2$. In some embodiments, a cell, such as a cell in the vegetative state or a cell in spore form, may be acclimated to $scCO_2$ by exposing the cell to $scCO_2$ for a short period prior to inoculating the culture or reactor.

As described herein, the inventors have surprisingly identified bacterial strains that are resistant or tolerant to $scCO_2$. In some embodiments, $scCO_2$ resistant cells are provided that are capable of growth in supercritical $CO_2$. In some embodiments, the cell is a bacterial cells, such as a bacterial cell belonging to the genus *Firmicutes*. In some embodiments the bacterial cell is capable of forming spores. In some embodiments, the cell belongs to the genus *Bacillus*. In some embodiments, the bacterial cell is a *Bacillus cereus*, *Bacillus subterranesu*, *Bacillus amyloliquefaciens*, *Bacillus safensis*, or a *Bacillus megaterium* cell, such as *Bacillus megaterium* strain SR7. In some embodiments, the supercritical-$CO_2$ tolerant strain has a bacterial 16S rRNA gene sequence that has at least 99.5% sequence identity with the 16S rRNA of *B. megaterium* SR7, *B. megaterium* DSM319, or *B. licheniformis* MR4. The identity may be higher or lower than this percent identity, such as about 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9% identity.

```
The 16S rRNA gene sequence of B. megaterium SR7 is provided by SEQ ID NO: 18:
gatgaacgctggcggcgtgcctaatacatgcaagtcgagcgaactgattagaagcttgcttctatgacgttagcggcggacgggtgagtaa
cacgtgggcaacctgcctgtgagactgggataacttcgggaaaccgaagctaataccggataggatcttctccttcatgggagatgattga
aagatggtttcggctatcacttacagatgggcccgcggtgcattagctagttggtgaggtaacggctcaccaaggcaacgatgcatagccg
acctgagagggtgatcggccacactgggactgagacacggcccagactcctacgggaggcagcagtagggaatcttccgcaatggacgaaa
gtctgacggagcaacgccgcgtgagtgatgaaggctttcgggtcgtaaaactctgttgttagggaagaacaagtacgagagtaactgctcg
taccttgacggtacctaaccagaaagccacggctaactacgtgccagcagccgcggtaatacgtaggtggcaagcgttatccggaattatt
gggcgtaaagcgcgcgcaggcggtttccttaagtctgatgtgaaagcccacggctcaaccgtggagggtcattggaaactggggaacttgag
tgcagaagagaaaagcggaattccacgtgtagcggtgaaatgcgtagagatgtggaggaacaccagtggcgaaggcggcttttggtctgt
aactgacgctgaggcgcgaaagcgtggggagcaaacaggattagataccctggtagtccacgccgtaaacgatgagtgctaagtgttagag
```

-continued
```
ggtttccgcccctttagtgctgcagctaacgcattaagcactccgcctggggagtacggtcgcaagactgaaactcaaaggaattgacgggg
gcccgcacaagcggtggagcatgtggtttaattcgaagcaacgcgaagaaccttaccaggtcttgacatcctctgacaactctagagatag
agcgttcccccttcgggggacagagtgacaggtggtgcatggttgtcgtcagctcgtgtcgtaagatgttgggttaagtcccgcaacgagcg
caaccccttgatcttagttgccagcatttagttgggcactctaaggtgactgccggtgacaaaccggaggaaggtggggatgacgtcaaatc
atcatgccccttatgacctgggctacacacgtgctacaatggatggtacaaagggctgcaagaccgcgaggtcaagccaatcccataaaac
cattctcagttcggattgtaggctgcaactcgcctatatgaagctggaatcgctagtaatcgcggatcagcatgccgcggtgaatacgttc
ccgggccttgtacacaccgcccgtcacacacgagagtttgtaacacccgaagtcggtggagtaaccgtaaggagctagccgcctaaggtg
ggacagatgattgggtgaagtcgtaacaa
```

The 16S rRNA gene sequence of B. licheniformis MR4 is provided by SEQ ID NO: 19:
```
agagtttgatcctggctcaggaacgaacgctggcggcgtgcctaatacatgcaagtcgagcggaccgacgggagcttgctcccttaggtca
gcggcggacgggtgagtaacacgtgggtaacctgcctgtaagactgggataactccgggaaaccggggctaataccggatgcttgattgaa
ccgcatggttcaatcataaaaggtggcttttagctaccacttacagatggacccgcggcgcattagctagttggtgaggtaacggctcacc
aaggcgacgatgcgtagccgacctgagagggtgatcggccacactgggactgagacacggcccagactcctacggggaggcagcagtaggga
atcttccgcaatggacgaaagtctgacggagcaacgccgcgtgagtgatgaaggttttcggatcgtaaaactctgttgttagggaagaaca
agtaccgttcgaatagggcggcaccttgacggtacctaaccagaaagccacggctaactacgtgccaactacgtgccagcagccgcggta
atacgtaggtffcaagcgttgtccggaattattgggcgtaaagcgcgcgcaggcggtttcttaagtctgatgtgaagccccggctcaaccg
gggagggtcattggaaactggggaacttgagtgcagaagaggagagtggaattccacgtgtagcggtgaaatgcgtagagatgtggaggaa
caccagtggcgaaggcgactctctggtctgtaactgacgctgaggcgcgaaagcgtggggagcgaacaggattagataccctggtagtccac
gccgtaaacgatgagtgctaagtgttagagggtttccgcccttttagtgctgcagcaaacgcattaagcactccgcctggggagtacggtcg
caagactgaaactcaaaggaattgacggggcccgcaagcggtggagcatgtggtttaattcgaagcaacgcgaagaaccttaccaggtct
tgacatcctctgacaaccctagagataggcttcccccttcgggggcagagtgacaggtggtgcatggttgtcgtcagctcgtgtcgtgaga
tgttgggttaagtcccgcaagcagcgcaaccccttgatcttagttagttgccagcattcagttgggcactctaaggtgactgccggtgacaa
accg
```

In general, *B. megaterium* SR7 may be distinguished from other industrial *B. megaterium* strains by analyzing the nucleotide sequence of any of a number of genes that differ between the strains. For example, *B. megaterium* SR7 may be distinguished from *B. megaterium* QM B1551 and DSM319 by analyzing the nucleotide sequence of atpD, dnaK, and/or groEL.

In some embodiments, the supercritical-$CO_2$ tolerant strain has a atpD gene having at least 99.5% identity to SEQ ID NO: 20. In some embodiments, the supercritical-$CO_2$ tolerant strain has a dnaK gene having at least 99.5% identity to SEQ ID NO: 21. In some embodiments, the supercritical-$CO_2$ tolerant strain has a groEL gene having at least 99.5% identity to SEQ ID NO: 22. The identity may be The nucleotide sequence of atpD of B. megaterium SR7 is provided by SEQ ID NO: 20.
(SEQ ID NO: 20)
```
atgagtcaaccagctgtagccaagcgctatgcactagctcttttcaattagcaacagaaaaacagatgatcgatgaaatgcaagaccagcta
caaatcgttgaagaggtgtttgctaaaacacctgaattaatggatgtattaactcatccaaaaattacaattgagcgaaaaaaacagtttgta
agtgaggcatttgctgaacttttcaccaactgttcaacatacggttcttctattattagagcgtcaccgcattcaaattgttagccaaatggta
caagagtatcgtttcctagcgaacgaagtacgtggcgtggcagatgcaactgtttattctgtcaaaccttttaagcgcagatgagaaaagagca
atctcgcaatcatttgcttcaaaagttggaaaacatacgttaaatatttcaaatgtagtagataaaagcctaatcggcggcgtgaagcttcgc
attggtaatcgtatctatgatggcagcattagcagcaaattagaaacgatccaccgaggacttcttgcacacagatcgtag
```

The nucleotide sequence of dnaK of B. megaterium SR7 is provided by SEQ ID NO: 21.
(SEQ ID NO: 21)
```
atggctcctgtgcgtcaagcttttaaaagatgcaggtctttctgcaagcgaacttgataaagtaatcttagttggtggttcaactcgtatccca
gcggtacaagatgcaatcaaaaaagaaactggtcaagatcctcataaaggtgtaaatcctgatgaagtagttgcacttggtgcagcaattcaa
ggtggcgtgttaactggtgatgtaaaagacgttgtattactagacgtaacgcctttatcactaggtatcgaaacaatgggtggcgtatttaca
aagctaattgagcgtaatacgacaattccaacaagtaaatcacaagtattctcaacggctgcagatagccaaacagctgtagatattcacgtt
cttcaaggtgagcgcccaatgtctgcagacaacaaaacgctaggacgtttccaattaacagacattcctcctgcaccacgcggagtacctcaa
atcgaagtatcattcgatattgataagaatggtatcgtaaacgttcgtgcaaaagatttaggtacaaacaaagacaggctattacaattaaa
tcttcaactggtttatcagatgacgaaatcgaccgcatggtaaaagaagcggaagaaaacgcagatgctgataagcaacgtaaagaagaagtg
gaactacgcaacgaagcagatcaattagtgttcacaactgaaaaaacattaaaagatcttgaaggaaaagtagaagaagctgaagtaacaaaa
gctaacgaagcaaaagatgctttaaaagctgcgattgaaaagaatgaccttgaagaaatcaaagcgaaaaaagatgaacttcaagaaatcgtt
caagcgttaactgtaaaattgtatgagcaagctcaacaagctcagcaagcaggtgaacaaggcgctcaaaatgatgatgttgtagatgcagag
tttgaggaagtaaacgacgacaaaaaataa
```

The nucleotide sequence of groEL of B. megaterium SR7 is provided by SEQ ID NO: 22.
(SEQ ID NO: 22)
```
atggcaaaagacattaaatttagcgaagaagcacgtcgcgcaatgctacgtggtgtagatacattggcaaatgctgtaaaagtaacgcttgga
ccaaaaggtcgtaacgttgtattagaaaagaaattcggttcaccgcttattacaaatgatggtgtaacaattgcaaaagaaatcgaattagaa
gacgcatttgaaaacatgggtgctaaattagtagccgaggttgcaaaacaaacgacgttgctggtgacagtacaactactgcaacagttttag
cgcaagcaatgateagagaaggtcttaaaaacgtaacggctggtgctaacccaatgggtatccgtaaaggtatggaaaaagcagtagctgta
cggttgaagaactaaaagcaatctctaaaccaattcaaggtaaagattcaattgctcaagtagcggctatctcagcagctgacgaagaagtag
gtcaactaatcgctgaagcaatggagcgcgttggtaacgacggcgttatcacacttgaagaatcaaaaggtttcacaactgaattagaagtgg
tagaaggtatgcagtttgaccgtggatatgcatctccttacatggtaactgattcagataaaatggaagctgtattagatgatccatacatct
taatcacagacaaaaaaatcgttaagattgaagaaatataccggtattatlatIcaagttattcaacaaggcaagcctctattaatcatcact
gaagacatagaaggegaaactttagcaacattagttgtgaacaaacttcgtggtcatttacagctgtagctgttaaagctcctggttttgat
gatcgtcgtaaagcaatgctacaagacgttgcgatcttaacaggcggagaagtaatcactgaagagcttggtcttgacttaaaaacagcaggc
atcgatcaattaggtcgcgatctaaaattgttgtaacaaaagaaaatacaacagitgtaaacggtgcaggaaacgcagaagatatcctagcac
gcgtaaaccaaatcaaagctcagcttgaagaaacaacttcagagtttgaccatgaaaaattacaagagcgcttagcaaaacttgctggtggcg
tagctgtaatcaaagttggtgcggcaactgaaacttgagttgaagcttaatacgtattgaagatgcattaaactctacgcgtutgcggt
tgaagaaggtatcgtagctggtggtggtactgcattagtaaatatctataataaagtagcaagcatcgaagctgacggtgacactgctacagg
tatcaacatcgtattacgtgegattgaagagctgtacgtcaaatcgctcacaatgctggtttagaaggatcagtaatcgttgagcgtctaaa
aggcgaagcagttggantggattcaacgctgcaactggcgagtgggtaaatatgetagacactggtatcgttgacccaacaaaagtaacgcgt
tcagctcttcaaaatgcttettctgtaacgactatgttcttaacaactgaagcagttgttactgacaagccagaagaaggcggagcacctgca
atgcctgacatgggeggcatgggtggaatggcggcatgatgtaa
``` higher or lower than this percent identity, such as about 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9% identity.

The supercritical-$CO_2$ tolerant strain in one preferred embodiment is *B. megaterium* strain SR7. A strain deposit has been submitted to the American Tissue Culture Collection (ATCC) for this strain. In another embodiment, the supercritical-$CO_2$ tolerant strain is *B. megaterium* strain DSM319 (Vary et al. *Appl. Microbiol. Biotechnol.* (2007) 76(5): 957-67; genome RefSeq number is NC_041403.1). In some embodiments, the sc$CO_2$ resistant cell is capable of growth at a pressure of greater than about 71 atm, such as about 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130 atm or more.

In some embodiments, the supercritical $CO_2$ resistant microbial strain is capable of growth below an acidity of about pH 4.6, such as below about pH 4.5, pH 4.4, pH 4.3, pH 4.2, pH 4.1, pH 4.0, pH 3.9, pH 3.8, pH 3.7, pH 3.6, pH 3.5, pH 3.4. pH 3.3, pH 3.2, pH 3.1, pH 3.0, pH 2.9, pH 2.8, pH 2.7, pH 2.6, pH 2.5, pH 2.4, pH 2.3, pH 2.2, pH 2.1, pH 2.0, or lower.

Supercritical $CO_2$ resistant cells can in some embodiments be identified by the following non-limiting characteristics and/or methods. In some embodiments, a supercritical $CO_2$ tolerant microbial strain is a microbial strain in which cell survival is maintained for at least 6 hours under supercritical $CO_2$ conditions as measured by membrane integrity probing. Membrane integrity probing can be performed, for example, by contacting the strain (e.g., cells of the strain) with a dye that is excluded by live cells and that can cross the cell membrane and/or cell wall in cells that are not alive. Methods and dyes used for membrane integrity probing are known in the art. Total cell counts can be compared to counts of cells that exclude dye to determine if the microbial strain has cells surviving under supercritical $CO_2$ conditions and therefore is a supercritical $CO_2$ tolerant microbial strain. In some embodiments, a sc$CO_2$ resistant cell or strain is one that has more than 0.1% live cells after 6 hours under a supercritical $CO_2$ headspace, preferably more than 0.5%, 1%, 2%, 5%, 10%, 15%, 20%, 25%, 30%, or more live cells after 6 hours under supercritical $CO_2$ conditions such as a supercritical $CO_2$ headspace.

In some embodiments, a sc$CO_2$ resistant cell is a microbial strain that demonstrates cell growth under continued exposure to sc$CO_2$ environments as measured by change over time of total cell count. Methods to determine change over time of total cell count are known to the person of skill in the art, and include such methods as epifluorescent DNA staining, membrane integrity probing and/or a method to quantify biomass. Samples of the culture can be taken at predetermined times or intervals and the samples analyzed for the characteristics described above. For example, samples can be taken each day for two or more days, such as at any two of 1, 2, 3, 4, 5, 6 7, 8, 9, 10, 11, 12, 13, or 14 days after inoculation of the culture. A comparison of the values of total cell count on the two or more days can be made to determine if the microbial strain demonstrates cell growth under continued exposure to supercritical $CO_2$ and thus is a sc$CO_2$ resistant cell. In some embodiments, the supercritical $CO_2$ tolerant microbial strains has a doubling time of about 1.0, 1.1, 1.2, 1.3, 1.4, 1.5, 1.6, 1.7, 1.8, 1.9, or 2.0 days, such as from 1.2 to 1.8 days, or 1.4 to 1.6 days.

Aspects of the present disclosure provide methods for producing a bioproduct. As used herein, a "bioproduct" refers to any molecule that may be produced by a cell associated with the invention and may be collected or recovered from the culture. In some embodiments, the bioproduct comprises a carbon chain that contains 3, 4, 5, 6, or 7 carbon molecules. In some embodiments, the bioproduct has properties that allow the bioproduct to partition into the sc$CO_2$, near critical $CO_2$, or liquid $CO_2$. In some embodiments, the bioproduct has hydrophobic characteristics. In some embodiments, the bioproduct is a fuel product. In some embodiments, the bioproduct is a non-fuel product. In some embodiments, the bioproduct is a hydrocarbon. In some embodiments, the bioproduct is an oxygenated hydrocarbon. In some embodiments, the bioproduct is a carboxylic acid. In some embodiments, the bioproduct is an alcohol, such as a primary alcohol, a secondary alcohol, or a tertiary alcohol. In some embodiments, the bioproduct is an aldehyde. In some embodiments, the bioproduct is a fatty acid. In some embodiments, the bioproduct is a ketone.

In some embodiments, the bioproduct is a natural product. As used herein, a "natural product" refers to any bioproduct that is produced by the cell and does not require recombinant expression of an enzyme that is not naturally expressed in the cell. In some embodiments, the cell has been genetically modified to produce enhanced titers of the natural product. Examples of natural products include, without limitation, ethanol, succinate, lactate, and acetate. In some embodiments, the cell has not been genetically modified and produces a natural product.

Also encompassed by the term bioproduct are heterologous molecules, for example molecules that are not natural products of the cells. In some embodiments, the bioproduct is a high value molecule, for example a biofuel. In some embodiments, the bioproduct is a substrate that may be used to produce a high value molecule. In some embodiments, the bioproduct is an alcohol, such as a short or medium chain alcohol. In some embodiments, the bioproduct is an aldehyde. Non-limiting examples of bioproducts that may be produced using the cells and methods described herein are 1-propanol, 1-butanol, 1-pentanol, 1-hexanol, 1-methylethanol (isopropanol), 2-methyl-propanol (isobutanol), 3-methyl-butanol (isopentanol), 4-methyl-pentanol (isohexanol), 2-phenylethanol, acetaldehyde, 1-butanal, 1-pentanal, 1-hexanal, 2-methyl-propanol (isobutanal), 3-methylbutanal (isopentanal), 4-methyl-pentanal (isohexanal), and 2-phenylethanal.

In some embodiments, the cell has been genetically engineered to express one or more heterologous enzymes. The terms "heterologous enzyme" or "heterologous polypeptide" refer to any enzyme or polypeptide that is expressed recombinantly the host cell. For example, a host cell may be genetically engineered to express an enzyme or polypeptide involved in a biosynthetic pathway that is not present in the host cell. In some embodiments, a host cell may be genetically engineered to express an enzyme or polypeptide that has one or more desired properties (e.g., activity level, specificity, etc). In some embodiments, the one or more heterologous enzymes or heterologous polypeptides are obtained from another organism. For example, in some embodiments, the cell is a bacterial cell and the heterologous enzyme or heterologous polypeptide is a yeast enzyme or protein. In some embodiments, the one or more heterologous enzyme or heterologous polypeptide are obtained from another species. For example, in some embodiments, the cell is a strain belonging to *Bacillus megaterium* and the heterologous enzyme or heterologous polypeptide are obtained from another bacterial species, for example *E. coli*. As will be appreciated by one of ordinary skill in the art, any of the heterologous enzymes described herein may be obtained from any source known in the art.

In some embodiments, the bioproduct is 1-propanol. In some embodiments, production of 1-propanol may involve expressing a threonine synthesis and/or an aldehyde-alcohol dehydrogenase, such as an aldehyde-alcohol dehydrogenase from *Clostridium acetobutylicum*.

In some embodiments, the bioproduct is 1-butanol. In some embodiments, production of 1-butanol may involve expressing a beta-keto-thiolase, an enoyl-CoA hydratase, a 3-hydroxybutyryl-CoA dehydrogenase, a Trans-enoyl-CoA reductase, and/or an Aldehyde-alcohol dehydrogenase. In some embodiments, the beta-keto-thiolase may be from *E. coli*. In some embodiments, the enoyl-CoA hydratase may be from *Clostridium acetobutylicum*. In some embodiments, the 3-hydroxybutyryl-CoA dehydrogenase may be from *Clostridium acetobutylicum*. In some embodiments, the trans-enoyl-CoA reductase may be from *T. denticola*. In some embodiments, the aldehyde-alcohol dehydrogenase may be from *Clostridium acetobutylicum*.

In some embodiments, the bioproduct is 1-pentanol. In some embodiments, production of 1-pentanol may involve expressing a threonine synthesase, a beta-keto-thiolase, an enoyl-CoA hydratase, a 3-hydroxybutyryl-CoA dehydrogenase, trans-enoyl-CoA reductase, and/or an aldehyde-alcohol dehydrogenase. In some embodiments, beta-keto-thiolase may be from *C. necator*. In some embodiments, the enoyl-CoA hydratase may be from *Clostridium acetobutylicum*. In some embodiments, the 3-hydroxybutyryl-CoA dehydrogenase may be from *Clostridium acetobutylicum*. In some embodiments, the trans-enoyl-CoA reductase may be from *T. denticola*. In some embodiments, the aldehyde-alcohol dehydrogenase may be from *Clostridium acetobutylicum*.

In some embodiments, the bioproduct is 1-hexanol. In some embodiments, production of 1-hexanol may involve expressing a beta-keto-thiolase, Beta-keto-acyl-CoA reducatase, an enoyl-CoA hydratase, a trans-enoyl-CoA reductase, and/or an aldehyde-alcohol dehydrogenase. In some embodiments, beta-keto-thiolase may be from *C. necator*. In some embodiments, the beta-keto-acyl-CoA reducatase may be from *C. necator*. In some embodiments, the enoyl-CoA hydratase may be from *C. necator*. In some embodiments, the trans-enoyl-CoA reductase may be from *T. denticola*. In some embodiments, the aldehyde-alcohol dehydrogenase may be from *S. cerevisiae*.

In some embodiments, the bioproduct is 1-methyl-ethanol. In some embodiments, production of 1-methyl-ethanol may involve expressing a beta-keto-thiolase, an acetoacetyl-CoA transferase, an acetoacetate decarboxylase, and/or an aldehyde-alcohol dehydrogenase. In some embodiments, the beta-keto-thiolase is from *C. necator*. In some embodiments, the acetoacetyl-CoA transferase is from *C. necator*. In some embodiments, the acetoacetate decarboxylase is from *C. necator*. In some embodiments, the aldehyde-alcohol dehydrogenase is from *Clostridium acetobutylicum*.

In some embodiments, the bioproduct is 2-methyl-propanol. In some embodiments, production of 2-methyl-propanol involves expressing an acetolactate synthase, a ketol-acid reductoisomerase, a dihydroxy-acid dehydratase, an alpha-ketoisovalerate decarboxylase and/or an alcohol dehydrogenase. In some embodiments, the ketol-acid reductoisomerase is from *E. coli*. In some embodiments, the dihydroxy-acid dehydratase is from *E. coli*. In some embodiments, the alpha-ketoisovalerate decarboxylase is from *E. coli*. In some embodiments, the alcohol dehydrogenase is from *E. coli*.

In some embodiments, the bioproduct is 3-methyl-butanol. In some embodiments, production of 3-methyl-butanol involves expressing an alpha-ketoisovalerate decarboxylase and/or an alcohol dehydrogenase. In some embodiments, the alpha-ketoisovalerate decarboxylase is from *L. lactis*. In some embodiments, the alcohol dehydrogenase from *E. coli*.

In some embodiments, the bioproduct is 4-methyl-pentanol. In some embodiments, production of 4-methyl-pentanol involves expressing an acetolactate synthase, a ketol-acid reductoisomerase, a dihydroxy-acid dehydratase, an alpha-ketoisovalerate decarboxylase, an aldehyde dehydrogenase, a propionyl-CoA transferase, a beta-keto-thiolase, a beta-keto-acyl-CoA reducatase, an enoyl-CoA hydratase, a trans-enoyl-CoA reductase, a carboxylic acid reductase, a 4'-phosphopantenheinyl transferase, and/or an alcohol dehydrogenase. In some embodiments, the acetolactate synthase is from *B. subtilis*. In some embodiments, the ketol-acid reductoisomerase is from *E. coli*. In some embodiments, the dihydroxy-acid dehydratase is from *E. coli*. In some embodiments, the alpha-ketoisovalerate decarboxylase is from *L. lactis*. In some embodiments, the aldehyde dehydrogenase is from *F. johnsonaie*. In some embodiments, the propionyl-CoA transferase is from *C. propionicum*. In some embodiments, the beta-keto-thiolase is from *C. necator*. In some embodiments, the beta-keto-acyl-CoA reducatase is from *C. necator*. In some embodiments, the enoyl-CoA hydratase is from *C. necator*. In some embodiments, the trans-enoyl-CoA reductase is from *T. denticola*. In some embodiments, the carboxylic acid reductase is from *N. iowensis*. In some embodiments, the 4'-phosphopantenheinyl transferase is from *B. subtilis*. In some embodiments, the alcohol dehydrogenase is from *Leifsonia*. sp strain S749.

In some embodiments, the bioproduct is 2-phenylethanol. In some embodiments, production of 2-phenylethanol involves expressing alpha-ketoisovalerate decarboxylase and/or an alcohol dehydrogenase. In some embodiments, the alpha-ketoisovalerate decarboxylase is from *L. lactis*. In some embodiments, the alcohol dehydrogenase is from *E. coli*.

In some embodiments, the bioproduct is acetaldehyde. In some embodiments, production of Acetaldehyde involves expressing an acetaldehyde dehydrogenase, such as an acetaldehyde dehydrogenase from *E. coli*.

In some embodiments, the bioproduct is 1-butanal. In some embodiments, production of 1-butanal involves expressing a beta-keto-thiolase, an enoyl-CoA hydratase, 3-hydroxybutyryl-CoA dehydrogenase, a trans-enoyl-CoA reductase, a thioesterase, a carboxylic acid reductase, and/or a 4'-phosphopantenheinyl transferase. In some embodiments, the beta-keto-thiolase is from *E. coli*. In some embodiments, the enoyl-CoA hydratase is from *Clostridium acetobutylicum*. In some embodiments, the 3-hydroxybutyryl-CoA dehydrogenase is from *Clostridium acetobutylicum*. In some embodiments, the trans-enoyl-CoA reductase is from *T. denticola*. In some embodiments, the thioesterase is from *E. coli*. In some embodiments, the carboxylic acid reductase is from *N. iowensis*. In some embodiments, the 4'-phosphopantenheinyl transferase is from *B. subtilis*.

In some embodiments, the bioproduct is 1-pentanal. In some embodiments, the production of 1-pentanal involves expressing a threonine synthesis, a beta-keto-thiolase, an enoyl-CoA hydratase, a 3-hydroxybutyryl-CoA dehydrogenase, a trans-enoyl-CoA reductase, a thioesterase, a carboxylic acid reductase, and/or a 4'-phosphopantenheinyl transferase. In some embodiments, the beta-keto-thiolase is from *C. necator*. In some embodiments, the enoyl-CoA hydratase is from *Clostridium acetobutylicum*. In some embodiments, the 3-hydroxybutyryl-CoA dehydrogenase is from *Clostridium acetobutylicum*. In some embodiments, the trans-enoyl-CoA reductase is from *T. denticola*. In some embodiments, the thioesterase is from *E. coli*. In some embodiments, the carboxylic acid reductase is from *N. iowensis*. In some embodiments, the 4'-phosphopantenheinyl transferase is from *B. subtilis*.

In some embodiments, the bioproduct is 1-hexanal. In some embodiments, the production of 1-hexanal involves expressing a beta-keto-thiolase, a beta-keto-acyl-CoA redu-catase, an enoyl-CoA hydratase, a trans-enoyl-CoA reductase, a thioesterase, a carboxylic acid reductase, and/or a 4'-phosphopantenheinyl transferase. In some embodiments, the beta-keto-thiolase is from *C. necator*. In some embodiments, the beta-keto-acyl-CoA reducatase is from *C. necator*. In some embodiments, the enoyl-CoA hydratase is from *C. necator*. In some embodiments, the trans-enoyl-CoA reductase is from *T. denticola*. In some embodiments, the thioesterase is from *E. coli*. In some embodiments, the carboxylic acid reductase is from *N. iowensis*. In some embodiments, the 4'-phosphopantenheinyl transferase is from *B. subtilis*.

In some embodiments, the bioproduct is 2-methyl-propanal. In some embodiments, the production of 2-methyl-propanal involves expressing an acetolactate synthase, a ketol-acid reductoisomerase, a dihydroxy-acid dehydratase, and/or an alpha-ketoisovalerate decarboxylase. In some embodiments, the acetolactate synthase is from *B. subtilis*. In some embodiments, the ketol-acid reductoisomerase is from *E. coli*. In some embodiments, the dihydroxy-acid dehydratase is from *E. coli*. In some embodiments, the alpha-ketoisovalerate decarboxylase is from *L. lactis*.

In some embodiments, the bioproduct is 3-methyl-butanal. In some embodiments, the production of 3-methyl-butanal involves expressing an alpha-ketoisovalerate decarboxylase, such as an alpha-ketoisovalerate decarboxylase from *L. lactis*.

In some embodiments, the bioproduct is 4-methyl-pentanal. In some embodiments, the production of 4-methyl-pentanal involves expressing an acetolactate synthase, a ketol-acid reductoisomerase, a dihydroxy-acid dehydratase, an alpha-ketoisovalerate decarboxylase, an aldehyde dehydrogenase, a propionyl-CoA transferase, a beta-keto-thiolase, a beta-keto-acyl-CoA reducatase, an enoyl-CoA hydratase, a trans-enoyl-CoA reductase, a carboxylic acid reductase and/or 4'-phosphopantenheinyl transferase from *B. subtilis*. In some embodiments, the acetolactate synthase is from *B. subtilis*. In some embodiments, the ketol-acid reductoisomerase is from *E. coli*. In some embodiments, the dihydroxy-acid dehydratase is from *E. coli*. In some embodiments, the alpha-ketoisovalerate decarboxylase is from *L. lactis*. In some embodiments, the aldehyde dehydrogenase is from *F. johnsonaie*. In some embodiments, the propionyl-CoA transferase is from *C. propionicum*. In some embodiments, the beta-keto-thiolase is from *C. necator*. In some embodiments, the beta-keto-acyl-CoA reducatase is from *C. necator*. In some embodiments, the enoyl-CoA hydratase is from *C. necator*. In some embodiments, the trans-enoyl-CoA reductase is from *T. denticola*. In some embodiments, the carboxylic acid reductase is from *N. iowensis*. In some embodiments, the 4'-phosphopantenheinyl transferase is from *B. subtilis*.

In some embodiments, the bioproduct is 2-phenylethanal. In some embodiments, the production of 2-phenylethanal involves expressing an alpha-ketoisovalerate decarboxylase, such as an alpha-ketoisovalerate decarboxylase from *L. lactis*.

In some embodiments, the bioproduct is isobutanol. In some embodiments, the production of isobutanol involves expressing an isoketovalerate decarboxylase and an alcohol dehydrogenase. In some embodiments, the isoketovalerate decarboxylase is from *L. lactis*. In some embodiments, the alcohol dehydrogenase is from *E. coli*.

According to aspects of the invention, cells that recombinantly express one or more genes associated with the invention, and the use of such cells in bioproducts, are provided. It should be appreciated that the genes associated with the invention can be obtained from a variety of sources. For example, homologous genes for use in methods associated with the invention can be obtained from other species and can be identified by homology searches, for example through a protein BLAST search, available at the National Center for Biotechnology Information (NCBI) internet site 10 (www.ncbi.nlm.nih.gov). In some embodiments, genes associated with the invention are synthetic. Any means of obtaining a gene encoding the enzymes associated with the invention are compatible with the instant invention. For example, genes and/or operons associated with the invention can be cloned, such as by PCR amplification and/or restriction digestion, from DNA from any source of DNA which contains the given gene. In some embodiments, a gene and/or operon associated with the invention is synthetic. Any means of obtaining a gene and/or operon associated with the invention is compatible with the instant invention.

In general, homologs and alleles typically will share at least 75% nucleotide identity and/or at least 90% amino acid identity to the sequences of nucleic acids and polypeptides, respectively, in some instances will share at least 90% nucleotide identity and/or at least 95% amino acid identity and in still other instances will share at least 95% nucleotide identity and/or at least 99% amino acid identity. The homology can be calculated using various, publicly available software tools developed by NCBI (Bethesda, Md.) that can be obtained through the NCBI internet site. Exemplary tools include the BLAST software, also available at the NCBI internet site (www.ncbi.nlm.nih.gov). Pairwise and ClustalW alignments (BLOSUM30 matrixsetting) as well as Kyte-Doolittle hydropathic analysis can be obtained using the MacVector sequence analysis software (Oxford Molecular Group). Watson-Crick complements of the foregoing nucleic acids also are embraced by the invention.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. The invention also embraces codon optimization to suit optimal codon usage of a host cell.

In some embodiments, modification of a gene before it is recombinantly expressed in a cell involves codon optimization for expression in a bacterial, yeast, or plant cell. Codon usages for a variety of organisms can be accessed in the Codon Usage Database (www.kazusa.or.jp/codon/). Codon optimization, including identification of optimal codons for a variety of organisms, and methods for achieving codon optimization, are familiar to one of ordinary skill in the art, and can be achieved using standard methods. It should be appreciated that any of the nucleic acids and/or polypeptides described herein can be codon-optimized and expressed recombinantly in a codon-optimized form. In some embodiments, modifying a gene before it is recombinantly expressed in a cell involves making one or more mutations in the gene before it is recombinantly expressed in a cell. For example, a mutation can involve a substitution or deletion of a single nucleotide or multiple nucleotides. In some embodiments, a mutation of one or more nucleotides in a gene will result in a mutation in the protein produced from the gene, such as a substitution or deletion of one or more amino acids.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as enzymatic activity. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (e.g., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also encompasses variants of polypeptides. As used herein, a "variant" of a polypeptide is a polypeptide which contains one or more modifications to the primary amino acid sequence of the polypeptide. Modifications which create a variant can be made to a polypeptide 1) to reduce or eliminate an activity of a polypeptide; 2) to enhance a property of a polypeptide; 3) to provide a novel activity or property to a polypeptide, such as addition of an antigenic epitope or addition of a detectable moiety; or 4) to provide equivalent or better binding between molecules (e.g., an enzymatic substrate). Modifications to a polypeptide are typically made to the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the amino acid sequence. One of skill in the art will be familiar with methods for predicting the effect on protein conformation of a change in protein sequence, and can thus "design" a variant of a polypeptide according to known methods. One example of such a method is described by Dahiyat and Mayo (1997) *Science* 278:82-87.

In general, variants include polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encode a polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the oncoding sequences of a gene or cDNA clone to enhance expression of the polypeptide. The activity of variant polypeptides can be tested by cloning the gene encoding the variant polypeptide into a bacterial or mammalian expression vector, introducing the vector into an appropriate host cell, expressing the variant polypeptide, and testing for a functional capability of the polypeptides as disclosed herein.

The skilled artisan will also realize that conservative amino acid substitutions may be made in polypeptides to provide functionally equivalent variants of the foregoing polypeptides, i.e., the variants retain the functional capabilities of the polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g., *Molecular Cloning: A Laboratory Manual*, J. Sambrook, et al., eds., Fourth Edition, Cold Spring Harbor Laboratory Press, Cold Spring Harbor, N.Y., 2012, or Current Protocols in Molecular Biology, F. M. Ausubel, et al., eds., John Wiley & Sons, Inc., New York. Exemplary functionally equivalent variants of polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will not be replaced, or alternatively, will be replaced by conservative amino acid substitutions. Preferably, 1, 2, 3, 4, 5, 6, 7, 8, 9, 10, 11, 12, 13, 14, 15, 16, 17, 18, 19, 20 residues can be changed when preparing variant polypeptides. It is generally preferred that the fewest number of substitutions is made. Thus, one method for generating variant polypeptides is to substitute all other amino 20 acids for a particular single amino acid, then assay activity of the variant, then repeat the process with one or more of the polypeptides having the best activity.

Conservative amino-acid substitutions in the amino acid sequence of a polypeptide to produce functionally equivalent variants of the polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. 82: 488-492, 1985), or by chemical synthesis of a gene encoding a polypeptide.

In some embodiments "rational design" is involved in constructing specific mutations in proteins such as enzymes. As used herein, "rational design" refers to incorporating knowledge of the enzyme, or related enzymes, such as its three dimensional structure, its active site(s), its substrate(s) and/or the interaction between the enzyme and substrate, into the design of the specific mutation. Based on a rational design approach, mutations can be created in an enzyme which can then be screened for increased production of a bioproduct relative to control levels or levels of the bioproduct produced using enzymes that do not contain the mutation(s). In some embodiments, mutations can be rationally designed based on homology modeling. As used herein, "homology modeling" refers to the process of constructing an atomic resolution model of one protein from its amino acid sequence and a three-dimensional structure of a related homologous protein.

In some embodiments, random mutations can be made in a gene, such as a gene encoding for an enzyme, and these mutations can be screened for increased production of a bioproduct relative to control levels or levels of the bioproduct produced using enzymes that do not contain the mutation(s). For example, screening for mutations in components of a biosynthetic pathway that lead to enhanced production of a desired bioproduct may be conducted through a random mutagenesis screen, or through screening of known mutations. In some embodiments, shotgun cloning of genomic fragments could be used to identify genomic regions that lead to an increase in production of a desired compound, through screening cells or organisms that have these fragments for increased production of the compound. In some cases one or more mutations may be combined in the same cell or organism.

In some embodiments, production of a desired compound (e.g., any of the bioproducts described herein) in a cell can be increased through manipulation of enzymes that act in the same pathway as the enzymes associated with the invention. For example, in some embodiments it may be advantageous to increase expression of an enzyme or other factor that acts upstream of a target enzyme such as an enzyme associated with the invention. This could be achieved by over-expressing the upstream factor using any standard method.

Optimization of protein expression can also be achieved through selection of appropriate promoters and ribosome binding sites. In some embodiments, this may include the selection of high-copy number plasmids, or low or medium-copy number plasmids. The step of transcription termination can also be targeted for regulation of gene expression, through the introduction or elimination of structures such as stem-loops. Further aspects of the invention relate to screening for bacterial cells or strains that exhibit optimized production of a desired compound (e.g., any of the bioproducts described herein).

As described above, methods associated with the invention involve generating cells that recombinantly express one or more genes of a synthetic pathway. Production of a desired compound for culturing such cells can be measured and compared to another cell. The cell can be further modified by increasing or decreasing expression of one or more genes or recombinantly expressing one or more additional genes. Production of a desired compound for culturing such cells can be measured again, leading to the identification of an improved cell.

In some embodiments, methods associated with the invention involve generating cells that express or overexpress one or more genes involved in the biosynthesis of a bioproduct.

The invention also encompasses nucleic acids that encode for any of the polypeptides described herein, libraries that contain any of the nucleic acids and/or polypeptides described herein, and compositions that contain any of the nucleic acids and/or polypeptides described herein. In some embodiments, one or more of the genes associated with the invention is expressed in a recombinant expression vector. As used herein, a "vector" may be any of a number of nucleic acids into which a desired sequence or sequences may be inserted, for example by restriction and ligation, for transport between different genetic environments or for expression in a host cell. Vectors are typically composed of DNA, although RNA vectors are also available. Vectors include, but are not limited to: plasmids, fosmids, phagemids, virus genomes and artificial chromosomes.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation, respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Fourth Edition, Cold Spring Harbor Laboratory Press, 2012. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes associated with the invention, for production of a bioproducts, such as those described herein, is demonstrated in the Examples section.

A nucleic acid molecule that encodes an enzyme associated with the invention can be introduced into a cell or cells using methods and techniques that are standard in the art. For example, nucleic acid molecules can be introduced by standard protocols such as transformation including chemical transformation and electroporation, conjugation, transduction, particle bombardment, etc. In some embodiments, the nucleic acid molecules encoding an enzyme may be introduced into a cell using transformation. In some embodiments, the method of introducing a nucleic into a cell may involve generating protoplasts, for example by subjecting the cells to a cell wall-disrupting agent, e.g., lysozyme, thereby generating a protoplast. In some embodiments, the protoplast is subsequently subjected to osmotic shock to incorporate the nucleic acid. In some embodiments, the cells are recovered, for example in high sucrose media, following incorporation of the nucleic acid. In some embodiments, the transformation further involves L-malic acid. Expressing the nucleic acid molecule encoding the enzymes of the claimed invention also may be accomplished by integrating the nucleic acid molecule into the genome.

In some embodiments one or more genes associated with the invention is expressed recombinantly in a bacterial cell. Bacterial cells according to the invention can be cultured in an aqueous phase comprising a growth media, such as any of the growth media described herein. As would be understood by one of ordinary skill in the art, routine optimization would allow for use of a variety of types of media. As described in the Examples, a non-limiting example of an optimized growth media was determined for culturing cells of the instant invention (e.g., *Bacillus megaterium*). In some embodiments, the growth media comprises a base media, such as LB or M9 media. In some embodiments, the growth media may be supplemented with additional components, such as yeast extract, trace metals, and/or glucose. Additional non-limiting examples of supplemental components include antibiotics, xylose or IPTG for gene induction, spore germination inducers, and/or ATCC Trace Mineral Supplement.

In some embodiments, the cells of the instant invention are provided in spore-form. In some embodiments, a spore germination inducer may be added to the growth media to induce germination of the cells and initiate production of a desired bioproduct. As will be appreciated by one of ordinary skill in the art, cells in spore form may be induced to germinate by any of a variety of inducers. The inducer used to stimulate spore germination may depend on any of a number of factors, such as the type of cell. In some embodiments, the spore germination inducer is physical treatment of the cells, such as by heat pretreatment. In some embodiments, the spore germination inducer is a nutrient or a portion of a bacterial cell wall (e.g., portion of peptidoglycan). In some embodiments, the spore germination inducer is D-alanine. In some embodiments, the spore germination inducer is leucine.

Similarly, other aspects of the growth media and growth conditions of the cells of the invention may be optimized through routine experimentation. For example, pH and temperature are non-limiting examples of factors which can be optimized. In some embodiments, methods described herein may involve incubating the cells (e.g., in multiphase reactors) at a temperature that allows metabolic activity of the cell and production of the desired bioproduct. In some embodiments, the methods involve incubating the cells at a temperature between about 10° C.-50° C. In some embodiments, the methods involve incubating the cells at a temperature about 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or about 50° C. In some embodiments, the methods involve incubating the cells at a temperature between about 35° C.-40° C. In some embodiments, the methods involve incubating the cells at a temperature about 35° C., 35.5° C., 36° C., 36.5° C., 37° C., 37.5° C., 38° C., 38.5° C., 39° C., 39.5° C., or about 40° C.

In some embodiments, the methods involve incubating the cells under conditions in which the density of $CO_2$ is greater than 0.1 g cm$^3$. In some embodiments, the methods involve incubating the cells under conditions in which the density of $CO_2$ is greater than 0.1 g cm$^3$, 0.2 g cm$^3$, 0.3 g cm$^3$, 0.4 g cm$^3$, 0.5 g cm$^3$, 0.6 g cm$^3$, 0.7 g cm$^3$, 0.8 g cm$^3$, 0.9 g cm$^3$, 1.0 g cm$^3$, 1.1 g cm$^3$, 1.2 g cm$^3$, or higher.

In some embodiments, factors such as choice of media, media supplements, and temperature can influence production levels of the desired compound (e.g., bioproducts described herein). In some embodiments the concentration and amount of a supplemental component may be optimized. In some embodiments, how often the media is supplemented with one or more supplemental components, and the amount of time that the media is cultured before collecting the bioproduct, is optimized. In some embodiments, the growth media (containing the cell of the instant invention) is cultured for at least 0.5, 1, 2, 3, 4, 5, 6, 7, 8, 9, 10, 12, 24, or 48 hours prior to collecting the bioproduct.

Chemical ions catalyzed by recombinant microorganisms are becoming more commonly used to replace syntheses of various chemicals, including in industrial scale reactors. Due to the presence of more complicated reaction mixtures (e.g., culture media, cells, reactants and products), downstream processing to isolate products can be difficult, particularly in processes requiring phase separation. Supercritical $CO_2$, near critical $CO_2$, or liquid $CO_2$ may be useful for both phase separation and product purification, such as by extraction of the culture medium, leading to more efficient, simple and cost effective processing.

In some embodiments, the bioproduct, once produced by the cultured cell, partitions to the aqueous phase of the multiphase reactor. In some embodiments, the bioproduct can be recovered (e.g., isolated) from the aqueous phase of the multiphase reactor. In some embodiments, the bioproduct, once produced by the cultured cell, partitions to the solvent phase (phase containing sc$CO_2$) of the multiphase reactor. In some embodiments, the bioproduct can be recovered (e.g., isolated) from the solvent phase of the multiphase reactor.

In some embodiments, the bioproduct is soluble or insoluble in the reaction mixture and may be recovered or collected from the appropriate phase of the reactor by any method known in the art, for example by filtration, pumping the fluid from the reaction vessel, or by venting the carbon dioxide from the reaction vessel for a soluble product.

According to aspects of the invention, bioproducts are produced through culturing cells, including cells that recombinantly express genes associated with the invention, under conditions involving a solvent phase comprising supercritical $CO_2$, near critical $CO_2$, or liquid $CO_2$. In some embodiments, the titer of the bioproduct is at least 10 mg L$^{-1}$. For example, the titer of the bioproduct can be at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900 or more than 900 mg L$^{-1}$ including any intermediate values.

In some embodiments, the titer of the bioproduct is at least 1 g L$^{-1}$. For example, the total titer of the bioproduct can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more than 50 g L$^{-1}$ including any intermediate values.

In some embodiments, the titer of the bioproduct is less than 10 mg L$^{-1}$. In some embodiments, the titer of the bioproduct is at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 15 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8 or 9.9 mg L$^{-1}$.

Any of the cells described herein may be cultured in a multiphase reactor. As used herein, a multiphase reactor refers to a reactor, such as a bioreactor, that comprises at least two distinct phases. In some embodiments, the multiphase reactor comprises at least an aqueous phase and a solvent phase. In some embodiments, the solvent comprises supercritical $CO_2$ (sc$CO_2$). In some embodiments, the solvent phase comprises sc$CO_2$ and one or more other solvents. In some embodiments, the solvent phase comprises sc$CO_2$ and inert helium. In some embodiments, the solvent comprises near critical $CO_2$. In some embodiments, the solvent phase comprises near critical $CO_2$ and one or more other solvents. In some embodiments, the solvent phase comprises near critical $CO_2$ and inert helium. In some embodiments, the solvent comprises liquid $CO_2$. In some embodiments, the solvent phase comprises liquid $CO_2$ and one or more other solvents. In some embodiments, the solvent phase comprises liquid $CO_2$ and inert helium. In some embodiments, the one or more other solvents, such as inert helium, are present in the solvent phase at less than or equal to about 3%. For example, the solvent phase may contain about 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or about 0.1% inert helium.

In some embodiments, the aqueous phase comprises the growth media and a cell or population of cells.

Also within the scope of the present invention are reactors comprising sc$CO_2$, near critical $CO_2$, or liquid $CO_2$ and at least one viable cell. In some embodiments, the reactor is a multiphase reactor comprising at least two distinct phases. In some embodiments, the reactor comprises a mixture of sc$CO_2$ and one or more other solvents, and at least one viable cell. In some embodiments, the reactor comprises a mixture of near critical $CO_2$ and one or more other solvents, and at least one viable cell. In some embodiments, the reactor comprises a mixture of liquid $CO_2$ and one or more other solvents, and at least one viable cell. As described herein, in some embodiments, the one or more other solvents comprise inert helium. In some embodiments, the sc$CO_2$, near critical $CO_2$, or liquid $CO_2$ and the viable cell of the reactor are located in different phases within the reactor.

In some embodiments, the reactor or multiphase reactor includes one or more pressurizable culture vessels for culturing microbes in fluid communication with a supply of $CO_2$ (e.g., supercritical $CO_2$, near critical $CO_2$, or liquid $CO_2$). The reactor may permit regulation of $CO_2$ pressure, permitting the user to increase or decrease $CO_2$ pressure as needed. In some embodiments, the reactor also permits changing the pressure conditions inside the one or more pressurizable culture vessels without interrupting the cultivation of microbes inside the one or more pressurizable culture vessels.

The cells can be grown under batch conditions or continuous flow conditions. The general parameters of batch and continuous processes are well known in the art. In one embodiment of a batch process, after a suitable time for production of one or more metabolites by the cells, the culture process (e.g., fermentation) is stopped by releasing the pressure in the bioreactor and collecting the $CO_2$ (e.g., supercritical $CO_2$, near critical $CO_2$, or liquid $CO_2$) mixture of supercritical $CO_2$ and one or more other solvents from the bioreactor. In one embodiment of a continuous process, the bioreactor is a pressurized continuous flow chemostat, and preferably a portion of the growth media is removed from the continuous flow chemostat. In some embodiments, the portion of the growth media that is removed is replaced with an amount of fresh growth media. Similarly, portions of the supercritical $CO_2$ or the mixture of supercritical $CO_2$ and one or more other solvents can be removed from the bioreactor (e.g., chemostat) in a continuous flow process. In some embodiments, the portion of the supercritical $CO_2$ or the mixture of supercritical $CO_2$ and one or more other solvents that is removed is replaced with an amount of fresh (i.e., unreacted) $CO_2$ (e.g., supercritical $CO_2$, near critical $CO_2$, or liquid $CO_2$) or a mixture of $CO_2$ (e.g., supercritical $CO_2$, near critical $CO_2$, or liquid $CO_2$) and one or more other solvents.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference.

EXAMPLES

Example 1: Development and Characterization of a scCO$_2$ Resistant *Bacillus megaterium* Strain To isolate and identify microorganisms that are able to grow in biphasic scCO$_2$-water reactors, fluid samples were collected from the deep subsurface McElmo Dome CO$_2$ field in Colorado, where scCO$_2$ had accumulated over 40-70 million years. Metagenomic analysis of formation fluids at this site suggested existence of an anaerobic microbial ecosystem. This work contributes to the establishment of a new technology for microbial bioproduction by enabling a bacterial strain capable of bioproduct generation to access the unique properties of sustainable solvent supercritical carbon dioxide.

Methods
Subsurface Fluid Sample Collection and Storage

Formation water samples from the McElmo Dome CO$_2$ field were used as inocula for microbial strain isolation through scCO$_2$-exposed enrichment culture and passaging. Sample fluids were sourced from the deep subsurface, where CO$_2$ is trapped at depths of 1800 to 2600 m within the 100 m thick dolomitic Leadville Formation (Allis et al., 2001; Gilfillan et al., 2009) and exists as a supercritical fluid at a temperature and pressure of approximately 65° C. and 135 atm (Allis et al., 2001). Sampled fluids from each of ten CO$_2$ production wells (operated by KinderMorgan CO$_2$) were collected from fluid-gas separators that were decanted and filled 15 hours prior to sample collection. At each separator, one liter of degassed fluid was collected in an acid-washed bottle (Nalgene; Rochester, N.Y.) and placed immediately on ice for use as enrichment culture inocula. Fluids were shipped on ice and stored at 4° C.

Supercritical CO$_2$-Exposed Enrichment Passaging Culturing Media and Vessels

Media for enrichment culture and passaging of McElmo Dome samples was a modified version of MS media (Colwell et al., 1997) with supplements targeting diverse metabolic groups as described in Peet et al., 2015. Media consisted of (in g/l) 0.5 yeast extract, 0.5 tryptic peptone, 10.0 NaCl, 1.0 NH$_4$Cl, 1.0 MgCl$_2$.6H$_2$O, 0.4 K$_2$HPO$_4$, 0.4 CaCl$_2$, 0.0025 EDTA, 0.00025 CoCl$_2$.6H$_2$O, 0.0005 MnCl$_2$.4H$_2$O, 0.0005 FeSO$_4$.7H$_2$O, 0.0005 ZnCl$_2$, 0.0002 AlCl$_3$.6H$_2$O, 0.00015 Na$_2$WoO$_4$.2H$_2$O, 0.0001 NiSO$_4$.6H$_2$O, 0.00005H$_2$SeO$_3$, 0.00005H$_3$BO$_3$, and 0.00005 NaMoO$_4$.2H$_2$O. MS medium supplements (g/l) consisted of 0.5 glucose (MS-FM); or 1.3 MnO$_2$, 2.14 Fe(OH)$_3$, and 1.64 sodium acetate (MS-MR); or 0.87 K$_2$SO$_4$, 0.83 FeSO$_4$, 0.82 sodium acetate (MS-SR). Following enrichment culturing and three passages using MS medium, Luria-Bertani Broth (LB) (Difco™; Becton, Dickinson, and Company; Franklin Lakes, N.J.) was included as an additional growth media for scCO$_2$ culturing. Phosphate buffered LB (P-LB) is amended with 50 mM K$_2$HPO$_4$. During all rounds of culturing, CO$_2$-incubated media was amended with 0.25 g/l of reducing agent Na$_2$S (at 0.25 g/l) and 0.001 g/l of the redox indicator resazurin. A summary of all media utilized during enrichment passaging and subsequent culturing is presented in Table 1.

High-pressure culturing vessels were constructed of % inch 316 stainless steel tubing for a 10 ml total capacity, and fitted with quarter turn plug valves (Swagelok (Solon, Ohio) or Hylok (Houston, Tex.)). Between uses, all vessel components were cleaned and soaked for at least two hours with 10% bleach and detergent, then autoclaved prior to assembly. All tubing in the pressurization manifold was filled before use with 10% bleach for 30 minutes, flushed with MilliQ-H2O, rinsed with 70% ethanol for 20 minutes, and dried with CO$_2$ gas. Prior to reactor loading, culture media was added to 100 ml serum bottles and degassed with a stream of 100%/o CO$_2$ for 30 minutes. Vessels were then filled to ½ capacity (5 ml) with inocula and degassed media, after which the headspace was pressurized with extraction grade CO$_2$ gas at a rate of 2-3 atm min-1 until reaching a final pressure of 100 atm. Since the CO$_2$ tank used for reactor pressurization contained a helium (He) cushion (in order to reach elevated pressures) the gas tank mixture contained 97-99% CO$_2$. Unless stated otherwise, after pressurization, reactors were incubated in a 37° C. warm room (to reach supercritical conditions) with shaking at 100 rpm to increase the extent of inocula and media mixing.

As described previously (Peet et al., 2015) prior to depressurization, culturing vessels were connected via 316 stainless steel tubing and fittings to a pressure gauge (Hunter) to measure the final vessel pressure. All reported vessel incubation data maintained pressures above the CO$_2$ critical point (>72.9 atm) when mixed with ≤3% inert Helium at 37° C. (Roth, 1998). Reactors were depressurized at a rate of 3-5 atm min-1 over approximately 30 min, at which point the vessels were transferred to the anaerobic chamber for sub-sampling, glycerol stock preparation and passaging.

TABLE 1

Summary of microbial culturing media

| Use | Name | Base | Supplements | Base Reference |
|---|---|---|---|---|
| Enrichment Passaging | MS-MR MS-SR MS-FM | MS: Yeast Extract, Trypticase Peptone, Salts | [a]Metals (Mn, Fe) + Acetate [b]Sulfates + Acetate 0.5 g/L Glucose | Colwell et al., 1997 |
| Pure Culture | P-LB P-LBA P-LBL P-LBAL M9+ M9A+ | LB: Yeast Extract Tryptone, NaCl M9: Phosphates, Salts | 50 mM Phosphate (Dibasic) 50 mM Phosphate (Dibasic) + 100 mM L-alanine 50 mM Phosphate (Dibasic) + 10 mM L-leucine 50 mM Phosphate (Dibasic) + 100 mM L-alanine + 10 mM L-leucine M9 + [c]0.1 X trace metals + 50 mM YE + 0.4% Glucose M9 + [c]0.1 X trace metals + 50 mM YE + 0.4% Glucose + 100 mM L-alanine | BD Difco ™ thelabrat.com* |

*www.thelabrat.com/plotocols/m9minimal.shtml
[a]1.30 g/1 MnO$_2$, 2.14 g/1 Fe(OH)$_3$, 1.64 g/1 Na-Acetate
[b]0.87 g/1 K$_2$SO$_4$, 0.83 g/1 FeSO$_4$•7H$_2$O, 0.82 g/1 Na-Acetate
[c]0.1 X trace metals solution (Boone, 1989); see methods Enumeration of Cell Density In order to quantify biomass of $CO_2$ cultures, 0.5-1.0 ml samples were treated with Syto 9 stain (Life Technologies), left in a dark room for 15 minutes to allow the stain to adhere to nucleic acids, collected on 0.22 um polycarbonate filters (Whatman® Nucleopore™; GE Healthcare Bio-sciences; Pittsburgh, Pa.) by vacuum pump, and washed twice with phosphate buffered saline (PBS) to remove excess stain. Each filter was mounted on glass slides for visualization by epifluorescent microscopy (Zeis Axioscope; Oberkochen, Germany) with immersion oil dropped below and above the filters, after which a cover slip was applied. Filters were stored at 4° C. in the dark until use. Cell densities were extrapolated by multiplying individual cell counts in a 10×10 microscope eyepiece grid by a dilution factor (if <1.0 ml of sample was filtered), and then multiplied by $3.46 \times 10^4$, because a 10×10 grid at 1000× magnification corresponds to $1/(3.46 \times 10^4)$ of a 25 mm filter. Final cell densities represented the mean values of cell counts in 15-20 separate 10×10 grids/sample. The limit of detection was considered to be one half of a cell per 15 grids, which corresponds to 1150 cells/ml. Fluorescent images were captured on a Nikon D 100 camera using the NKRemote live-imaging software. Cell density calculations and morphological observations were conducted for inocula prior to pressurization as well as after incubation in order to determine the extent to which growth had occurred. CFU plating was performed using LB Agar with order of magnitude dilutions in autoclaved PBS buffer prior to plating with cell-free negative controls. Plates were dried, inverted and incubated overnight at 37° C. prior to colony counting.

Enrichment Cultures and Serial Passaging

Fluids from four of the sampled wells (HB-5/Well 2, HE-1/Well 4, HF-3/Well 5, YB-4/Well 7) were selected as inocula for enrichment culturing under $scCO_2$ because they appeared to harbor elevated cell density by fluorescent microscopy. 100 ml of fluids from the four respective wells were filtered onto 5 mm, 0.2 μm pore size, polycarbonate filters (Nucleopore; GE Healthcare Bio-sciences; Pittsburgh, Pa.) in order to concentrate microbial content. The filters were then placed inside an anaerobic chamber (Coy Lab Products; Grass Lake, Mich.) containing 95% $CO_2$/5% $H_2$. Using sterilized tweezers, filters were then placed inside 10 ml 316 stainless steel pressure reactors with 1 ml of formation fluid from the same well used to concentrate biomass on the filter. The filters and formation fluids were then amended with 4 ml of growth media. After the initial round of growth using filter-concentrated biomass inoculum, cultures were inspected by epifluorescence microscopy to identify biomass accumulation. Cultures that showed growth relative to inocula based on cell counts were serially passaged by dilution in freshly degassed growth media to achieve initial concentrations of approximately $10^4$ cells/ml. The McElmo Dome enrichment culture (M1) was incubated for 46 days, while subsequent passages were incubated for 19 days (M2), 33 days (M3), and 35 days (M4).

Strain Isolation and $scCO_2$ Growth Verification

Samples from the final round of passaging (M4) were plated on LB agar and incubated overnight at 37° C. under aerobic conditions at ambient pressure. Single colonies with unique morphologies were used to inoculate liquid LB. DNA extraction from overnight grown cultures was performed using the Qiagen Blood and Tissue DNA extraction kit protocol for gram-positive cells (Qiagen; Hilden, Germany). Resulting DNA was used as template for 16S rRNA PCR using universal Bacterial primers 515F (3'-GTGCCAGCMGCCGCGGTAA-5' (SEQ ID NO: 1)) and 1492R (3'-GGTTACCTTGTTACGACTT-5' (SEQ ID NO: 2); Turner et al., 1999). PCR mixtures (20 μl per reaction) included 1× Phusion High Fidelity Polymerase buffer, 0.4 uM of each primer (Integrated DNA Technologies (IDT); Coralville, Iowa), 0.4 uM deoxynucleotide mixture and 1 U Phusion Polymerase (New England Biolabs; Ipswich, Mass.). Thermal cycling conditions consisted of an initial 5 minutes at 95° C. followed by 30 cycles of denaturation at 95° C. for 30 sec, annealing at 55° C. for 30 sec, and extension at 72° C. for 90 sec; followed by a final extension time of 7 min. Every PCR reaction included negative and positive controls (Peet et al., 2015). PCR products were then purified using Exo-SAP IT (Affymetrix; Santa Clara, Calif.) and submitted for Sanger sequencing (Genewiz, Cambridge, Mass.). Returned sequences were processed in CLC Genomics Workbench (Version 7; Qiagen Bioinformatics), including primer removal and universal sequence trimming to 918 bp for all isolates. Sequence alignment and tree building of isolates and reference sequences consisting of *Bacillus*, closely related taxa, and an *E. coli* outgroup using a 914 bp alignment was also conducted in CLC Genomics Workbench. Tree building used a bootstrapped (100×) neighbor-joining method, which was visualized in FigTree v 1.4.2. 16S rRNA reference sequences were downloaded from GenBank (NCBI) or generated in Peet et al., (2015; e.g., *Bacillis* sp. OT1, *Bacillus* sp MIT0214).

Because *Bacillus* spp. spores were previously demonstrated to be able to germinate and grow under 1 atm $CO_2$ and $scCO_2$ headspace conditions (Peet et al., 2015), spores of all *Bacillus* spp. strains isolated from McElmo Dome fluids were prepared using the protocol described in Kim and Goepfert (1974). Briefly, colonies streaked from glycerol stocks were used to inoculate overnight cultures in LB medium that were incubated under aerobic conditions at 37° C. while shaking at 100 rpm. Dense, stationary-phase cultures were then diluted 1:50 into 100 ml of Modified G Medium, which is composed of (in g/l): yeast extract 2.0, $CaCl_2.2H_2O$, 0.025, $K_2HPO_4$ 0.5, $MgSO_4.7H_2O$ 0.2, $MnSO_4.4H_2O$ 0.05, $ZnSO_4.7H_2O$ 0.005, $CuSO_4.5H_2O$ 0.005, $FeSO_4.7H_2O$ 0.0005, $(NH_4)_2SO_4$ 2.0, adjusted to pH 7.1 after autoclaving. Modified G Medium-inoculated cells were incubated at 37° C. for 72 hours to induce sporulation, then centrifuged for 10 minutes at 10,000×g. The pellet was resuspended and centrifuged 5 times in autoclaved wash buffer containing 0.058 g/l $NaH_2PO_4.H_2O$ and 0.155 g/l $Na_2HPO_4.7H_2O$ with 0.01% (v/v) Tween® 20 to prevent clumping. Spores were stored in wash buffer at 4° C. until use and periodically assayed for continued viability after extended storage by LB agar colony plating.

Growth of *B. megaterium* SR7 (and other isolates) under $scCO_2$ was validated by triplicate incubation for 28-42 days inoculated in pure culture from spores loaded at ~1×10$^4$ spores/ml using multiple media (Table 1). Cultures were scored for growth by filter counts, as previously described.

Isolate *B. megaterium* Strain SR7 Genomics

Understanding the genomic landscape of strain SR7 provides useful insight into endogenous physiological and metabolic capacities and will aid future development of SR7 as a strain for bioengineered product generation for in situ $scCO_2$ extraction. SR7 genomic DNA was extracted from a 10 ml overnight aerobic LB culture using the Qiagen Blood & Tissue Kit, following the Gram-positive bacteria protocol. Eluted DNA was submitted to the MIT BioMicro Center for sequencing using PacBio SMRT technology (Pacific Biosciences; Menlo Park, Calif. Following sequencing, the PacBio assembler software was used to assemble SR7 contigs, which were then compared to the genome of closely related strain *B. megaterium* QM B1551 (Eppinger et al., 2011) using the online tools nucmer and "double act" (hpa-bioinfotools.org.uk/pise/double_act.html), the latter of which cuts the query and reference DNA into smaller pieces to create an inter-genome Blastn comparison file that can be viewed in the Artemis Comparison Tool (ACT; Carver et al., 2005). Based on the ACT comparison, the putative SR7 chromosome (longest contig) was adjusted to start at the beginning of gene dnaA in agreement with the reference genome. The closed chromosome was then plotted by DNA Plotter (sanger.ac.uk/resources/software/dnaplotter) and submitted to RAST (Aziz et al., 2008) for gene prediction and functional annotation. Remaining contigs, potentially indicative of endogenous plasmid based on sequenced *B. megaterium* strains, were also submitted to RAST for annotation. Shared and unique RAST-annotated genes between SR7 and *B. megaterium* reference genomes QM B1551, DSM319 (Eppinger et al., 2011), and WSH-002 (Liu et al., 2011) were determined using online tool Venny 2.1. Inter-strain sequence comparisons were conducted using the Average Nucleotide Identity (ANI) calculator (enve-omics.ce.gatech.edu/ani).

Physiological Characterization of *B. megaterium* Strain SR7

To help guide optimization of growth conditions for strain SR7, physiological tests were conducted under aerobic conditions. To determine tolerance for pH, salinity and bicarbonate, high throughput culturing was done in 96 well plates and scored for growth by $OD_{600}$ using a microplate reader (BioTek Synergy 2; BioTek; Winooski, Vt.). 200 uL LB solutions/well were inoculated in triplicate with 10$^4$ spores/ml (based on SR7 spore stock filter counts) and incubated on a plate rocker at 37° C. with unamended positive and cell-free negative LB controls. Tests for pH tolerance (pH 2-10) were conducted in LB medium amended with HCl or NaOH. The effect of salinity and bicarbonate on growth was determined by adding NaCl (1-10%) and $NaHCO_3$ (0.1-0.5M), respectively, to LB media. Optimal SR7 growth temperature was tested by inoculating 10$^4$ spores/ml in 5 ml of LB in triplicate at temperatures of 9-55° C. Cultures and cell-free negative controls were incubated without shaking, with subsamples taken for periodic $OD_{600}$ measurements. SR7 antibiotic sensitivity was determined by supplementing 5 ml LB with ampicillin (5-50 µg/ml), chloramphenicol (3.5-35 µg/ml), kanamycin (5-50 µg/ml), spectinomycin (10-100 µg/ml), streptomycin (10-100 µg/ml), or tetracycline (1.5-15 µg/ml). 5 mL cultures inoculated with 10$^4$ spores/ml were incubated in a spinning rack at 100 rpm for 24 hours at 37° C. and assayed for growth by comparing $OD_{600}$ measurements to unamended positive and cell-free negative LB controls.

Biolog GenIII Microplates 96 well plates (Biolog; Hayward, Calif.)(unamended and with a trace metals solution amendment (Boone et al., 1989)) were used to determine SR7 growth substrates and to test growth sensitivities relative to a positive control. Plates were inoculated with 2-4 SR7 colonies grown overnight on solid BUG media (Biolog) such that starting $OD_{490}$ transmission was 90-94%. Plates were incubated at 37° C. on a plate shaker at 200 rpm and assayed for growth using NADH-dependent colorimetric changes measured by $OD_{490}$ on a microplate reader (BioTek Synergy 2; BioTek; Winooski, Vt.). Total growth was quantified by integrating the area under the curve of $OD_{490}$ values over the course of the incubation, and categorized as: "−" displays an area less than the negative control, "+" is greater than the negative control, but less than half of the maximum value, and "+++" is between "+" and the maximum value.

Process Improvements for *B. megaterium* SR7 Growth Under 1 Atm $CO_2$ and $scCO_2$ After initial physiological characterization assays, subsequent culturing improvements sought to establish consistent, replicable growth of SR7 under $scCO_2$ by conducting experiments under 1 atm $CO_2$ as a proxy for pressurized conditions (e.g., Peet et al., 2015). In order to improve spore germination frequencies, the effects of chemical inducers and mixing regimes (e.g., culture volume and shake speed) were examined, as the literature has shown certain compounds (e.g., amino acids, $KNO_3$, peptidoglycan, Ca-dipicolinic acid, and others; Ghosh and Setlow, 2009) and conditional treatments (temperature, pressure; Wei et al., 2010) increase *Bacillus* spore germination rates. Experiments testing the role of mixing speed and modified culture media on rates of vegetative outgrowth were conducted under 1 atm $CO_2$ with $CO_2$-degassed media or buffer in 100 ml serum vials with clamped rubber stoppers.

Evaluating the Effect of Spore Germination Inducers

The effect of shake speed on spore germination was assayed by inoculating 5 ml LB medium with *B. megaterium* SR7 spores at a starting concentration of 10$^5$ spores/ml. Singleton cultures were subjected to shake speeds of 150, 250, and 350 rpm and scored for growth by $OD_{600}$ and LB agar colony plating.

The ability to induce spore germination based on literature precedent was tested by inoculating triplicate 10 ml cultures of SR7 spores at $OD_{600}$ 0.01 in LB amended with 100 mM L-alanine, LB subjected to a heat activation (65° C. for 15 minutes) upon inoculation, or unamended LB as a control. Growth was scored by $OD_{600}$ and LB agar CFU plate counts. In addition, subsamples were heat-killed by exposure to 80° C. for 10 minutes (Setlow, 2006) prior to plating, to ascertain remaining spore concentrations, as heat exposure is lethal to vegetative cells.

The role of candidate germination inducers was subsequently investigated in PBS buffer rather than growth medium to decouple the germination process from outgrowth. *B. megaterium* SR7 spores were loaded in triplicate 10 ml PBS amended with 100-250 mM L-alanine, 100 mM L-alanine with heat treatment, 25 mM L-leucine, or an unamended PBS control. The extent of germination was measured by fluorescence microscopy staining patterns (e.g., the degree of cell membrane penetration by DNA stain), bulk fluorescence, $OD_{600}$, and flow cytometry (FCM). A total of 100-300 cells per filter were counted and categorized as either "dormant" or "germinated" if the spore stain was localized to the cell membrane or diffused within the interior of the cell, respectively (Cronin and Wilkinson, 2007). Cells displaying an intermediate degree of stain dispersal ("activated") were categorized as germinated (FIG. 1).

Sub-sample bulk fluorescence (Syto9®) was measured by microplate reader (BioTek Synergy 2; 485/20 excitation, 528/20 emission) and $OD_{600}$ was measured by microplate reader. OD should decrease in germinated cells (the index of refraction decreases due to hydration upon spore coat degradation) while bulk fluorescence should increase as the nucleic acid stain progressively penetrates and permeates the cell (Magge et al., 2009). To test for germination after a delayed inducer spike rather than at the moment of inoculation, *B. megaterium* SR7 spores loaded at $OD_{600}$ 0.01 were incubated overnight in 30 ml of PBS, passaged into PBS amended with L-alanine (25-250 mM) or L-leucine (10-25 mM) and then assayed for germination by bulk fluorescence and $OD_{600}$ during incubation.

FCM was employed as a high-throughput germination assay based on Baier et al., (2010). Triplicate cultures of *B. megaterium* SR7 spores loaded at $OD_{600}$ 0.01 were incubated overnight in PBS and PBS amended with 2.5-250 mM L-alanine, along with cell-free PBS controls. Prior to loading on the flow cytometer (BD FACS Canto II HTS-1; Becton Dickinson; Franklin Lakes, N.J.) cultures were diluted 1/50 in PBS and stained with Syto16® and propidium iodide (PI) in the dark for at least 30 minutes prior to analysis. After spore and media-only samples were used to set forward scatter, side-scatter, Syto16 and PI gates, sample data was collected and analyzed using FACSDIVA™ software (BD Biosciences; Franklin Lakes, N.Y.).

Testing the Effect of Mixing on Vegetative Growth

After testing for the potential to induce germination in *B. megaterium* SR7, bacterial growth rates were evaluated in order to increase metabolic activity for eventual bioproduct pathway expression. Experiments testing the role of shake speed on vegetative growth rate were inoculated with passaged cells of spore-loaded overnight cultures grown under 1 atm $CO_2$. Triplicate 25 ml LB cultures of vegetative cells loaded at $OD_{600}$ 0.01 were subjected to shake speeds of 150, 250, and 350 rpm, with growth assayed by $OD_{600}$ and LB agar colony plating.

Minimal Media Development to Improve Growth

Development of a minimal medium enables individual chemical components to be tuned in order to establish optimized growth from a sole carbon source under 1 atm $CO_2$. Initial attempts to generate *B. megaterium* SR7 growth in triplicate cultures tested various amendments to M9 base medium (thelabrat.com; Table 1), including 0.4% glucose or 0.4% xylose amendments as sole carbon sources, with or without trace metals solution (Boone et al., 1989). The 1× concentration trace metals solution consisted of (in g/l): 0.005 $Na_2$(EDTA), 0.0002 $NiSO_4.6H_2O$, 0.0005 $CoCl_2.6H_2O$, 0.0001$H_2FeO_3$, 0.001 $FeSO_4.7H_2O$, 0.0001$H_3BO_3$, 0.001 $ZnCl_2$, 0.0001 $NaMoO_4.2H_2O$, 0.0004 $AlCl_3.6H_2O$, 0.001 $MnCl_2.4H_2O$, 0.0003 $Na_2NO_4.2H_2O$, 0.0002 $CaCl_2$. To further boost growth, triplicate cultures of M9+0.4% glucose were amended with dilute LB (0.001-0.01×) or yeast extract (YE; 0.001-0.01×) as de facto vitamin and co-factor solutions, and/or $NaNO_3$ (5 mM) as an alternative electron acceptor. All M9 incubations were scored for growth by $OD_{600}$ and designated as robust above $OD_{600}$>0.600, low level between 0.2-0.6, and no growth below 0.2. Passaged vegetative cultures were also assayed in duplicate for growth (by $OD_{600}$) amended with a range (0.1×, 0.25×, 1×) of trace metals solutions in M9+0.4% glucose+0.01×YE media, including in the presence and absence of 5 mM $NaNO_3$.

Growth curves under optimized shaking conditions were generated to establish baseline metabolic characteristics of strain *B. megaterium* SR7. Vegetative SR7 cells were passaged in quadruplicate at $OD_{600}$ 0.01 in minimal or LB media and assayed for growth by $OD_{600}$, LB agar colony plating, and glucose consumption (for minimal medium cultures only) measured on the YSI 2900 with 2814 glucose starter kit. Doubling times were calculated using a log-linear fit of CFU and $OD_{600}$ data points during exponential growth.

Analysis of *B. megaterium* SR7 Fermentation Products Under 1 Atm $CO_2$ and sc$CO_2$ Following optimization of growth conditions under 1 atm $CO_2$ and sc$CO_2$, identification of fermentation products would establish potential target pathways for redirecting carbon flux and would demonstrate the ability to generate extracellular natural products. Metabolite identification and quantification was conducted by high performance liquid chromatography (HPLC). Triplicate cultures of *B. megaterium* SR7 vegetative cells inoculated in M9+ or LB at $OD_{600}$ 0.01 were scored for growth by $OD_{600}$. 500 ul of supernatant from each spun down sample (5 mins at 21,000×g) was loaded on the HPLC (Agilent 1100 series; Agilent Technologies; Santa Clara, Calif.) for analysis. Compound separation was achieved using an Aminex HPX-87H anion exchange column; Bio-Rad Laboratories, Hercules, Calif.) according to the protocol established by Buday et al. (1990) using 5 mM $H_2SO_4$ as the mobile phase. Analyte concentrations were established using standard curves for fermentative substrates and products, including glucose, succinate, lactate, formate, acetate, and ethanol. Though retention times were known for pyruvate, malic acid, propionate, 2-3 butanediol, butyrate, propanol, crotonate, butyraldehyde, valerate, butanol, and pentanol, standard curves were not generated because no apparent peaks were detected for these compounds.

Evaluating SR7 sc$CO_2$ Growth Using 1 Atm $CO_2$-Optimized Conditions

SR7 growth outcomes were investigated under sc$CO_2$ headspace (90-100 atm; 37° C.) while shaking at 250 rpm. SR7 spores were inoculated at starting concentrations of ~3×10⁴ spores/ml (unless otherwise specified) in either 50 mM $K_2HPO_4$-buffered LB (P-LB) or M9+ media (Table 1). Experiments assaying the effect of germination induction included 100 mM L-alanine and 10 mM L-leucine media amendments and heat treatment upon reactor pressurization (70° C. for 10 minutes). Incubations were conducted in 316 stainless steel vessels and gradually pressurized to supercritical conditions using a $CO_2$/He cylinder, as previously described. SR7 germination was verified by the identification of vegetative cell morphologies using fluorescence microscopy of Syto9-stained cultures. Growth was defined by an increase of at least 10-fold growth in cell counts relative to $t_0$.

In order to ascertain whether L-alanine, L-leucine, and heat treatment induce germination under $scCO_2$ headspace, three replicate experiments were conducted comparing growth for SR7 spores when loaded in media P-LB, P-LBL, P-LBAL, or P-LBA±heat treatment (Table 1; Table 2). Reactors were depressurized and scored for germination and growth by fluorescence microscopy, as previously described.

Cell densities of P-LB and L-PBA incubations from the three experiments (Table 3; Incubations A-C) were subjected to statistical analysis to establish the significance of 100 mM L-alanine on spore growth outcomes. A non-parametric Wilcoxon/Kruskal-Wallis Test was performed on the dataset (JMP® Pro v.12; SAS Cary, N.C.) where growth outcome (growth/no growth) and cell density fold change (relative to $t_0$) were dependent variables and incubation time and inducer presence/absence (±100 mM L-alanine) were independent variables.

TABLE 2

Incubation conditions assaying chemical germination induction and heat treatment effects on SR7 growth under $scCO_2$

| Incubation | Duration | Media | # Columns |
|---|---|---|---|
| A | 18 days | P-LB | 7 |
| | | P-LBA | 7 |
| | | P-LBA (+Heat) | 6 |
| | | P-LBL | 7 |
| | | P-LBAL | 7 |
| | | Neg Ctrl | 4 |
| B | 20 days | P-LB | 7 |
| | | P-LBA | 7 |
| | | P-LBL | 6 |
| | | P-LBAL | 6 |
| | | Neg Ctrl | 4 |
| C | 18 days | P-LB | 6 |
| | | P-LBA | 5 |
| | | Neg Ctrl | 4 |

TABLE 3

L-alanine-amended $scCO_2$ incubations in P-LBA and M9A+

| Media | Duration | # Cultures | # Neg Ctrl |
|---|---|---|---|
| P-LBA | 18 days | 7 | 4 |
| | 20 days | 7 | 4 |
| | 18 days | 5 | 4 |
| | Total | 19 | 12 |
| M9A+ | 18 days | 18 | 6 |
| | 20 days | 7 | 4 |
| | Total | 25 | 10 |

Growth was compared for spore-inoculated cultures in L-alanine-amended M9+(M9A+; Table 1) and P-LBA to determine whether either medium facilitates superior growth under $scCO_2$ when controlling for the presence of L-alanine. Buffering capacity was comparable for both media based on similar phosphate content. A summary of the M9A+ vs. P-LBA incubations is provided in Table 4. A non-parametric Wilcoxon/Kruskal-Wallis Test (JMP® Pro v. 12) was run on the P-LBA and M9A+ datasets, where growth outcome (growth/no growth) and cell density fold change (relative to starting concentrations) were the dependent variables and incubation time and inducer presence/absence (±100 mM L-alanine) were the independent variables.

To establish whether increasing starting spore concentrations and incubation time improves the likelihood of growth, replicate cultures in M9A+ loaded with four starting spore concentrations ($5\times10^5$, $5\times10^3$, $5\times10^1$, $5\times10^{-1}$ cells/ml) were run over an 18-day time course. Samples were prepared for cell counts by fluorescence microscopy according to previously described protocols. Because reactors inoculated with $5\times10^1$ and $5\times10^{-1}$ cells/ml are below the limit of detection by direct counts, their concentrations are recorded as one half the detection limit ($1.15\times10^3$ cells/ml, as previously discussed). M9A+ time course data was combined with prior M9A+$scCO_2$ results to develop a logistic regression model (JMP Pro® v. 12) for growth frequency where outcome (growth/no growth) was the dependent variable, and inocula concentration and incubation time were independent variables.

Results

Isolation of $scCO_2$-Tolerant Strains from McElmo Dome Fluids

Enrichment cultivation and serial passaging of McElmo Dome formation fluids with microbial growth media in high-pressure reactors under supercritical $CO_2$ headspace enabled the isolation of six different microbial strains, all of which are taxonomically classified within the *Bacillus* genus. Cultures were assayed for growth after the enrichment (M1=45 days) and each of three subsequent passages (M2=19 days, M3=33 days, M4=35 days) by epifluorescence microscopy methods (Table 4). Cell density from enrichment cultures was regularly observed to be greater than $10^5$ cells/ml. The second (M2) and third (M3) round of culturing winnowed down the number of reactors demonstrating growth, with passaging of most media-inocula combinations discontinued due to lack of growth (or in some cases loss of pressure in reactors). The media-inocula combinations that were incubated during the fourth round (M4) of culturing showed maximum biomass accumulations of at least $7\times10^5$ cells/ml (Table 6), including Well 2+MS-MR media ($7.4\times10^5$ cells/ml), Well 4+MS-MR ($1.2\times10^8$ cells/ml), Well 7+MS-MR ($3.1\times10^7$ cells/ml), and Well 7+MS-SR ($6.9\times10^6$ cells/ml).

TABLE 4

Enrichment passaging diversity, biomass, and isolate strain summary

| | Passage | | | | |
|---|---|---|---|---|---|
| | M1 | M2 | M3 | M4 | |
| | Duration (d) | | | | |
| | 45 | 19 | 33 | 35 | Isolate Strain(s) |
| WELL 2/HB-5 | | | | | |
| MS-FM | +++ | ++ | n.d. | n.d. | No Isolate |
| MS-MR | +++ | ++ | +++ | ++ | MR2 |
| MS-SR | +++ | ++ | + | n.d. | No Isolate |
| WELL 4/HE-1 | | | | | |
| MS-FM | ++ | n.d. | n.d. | n.d. | FM4 |
| MS-MR | +++ | + | +++ | +++ | MR4 |
| MS-SR | +++ | + | − | n.d. | No Isolate |
| WELL 5/HF-3 | | | | | |
| MS-MR | +++ | + | + | n.d. | No Isolate |

TABLE 4-continued

Enrichment passaging diversity, biomass, and isolate strain summary

| | Passage | | | | |
|---|---|---|---|---|---|
| | M1 | M2 | M3 | M4 | |
| | Duration (d) | | | | |
| | 45 | 19 | 33 | 35 | Isolate Strain(s) |
| WELL 7/YB-4 | | | | | |
| MS-FM | +++ | + | n.d. | n.d. | No Isolate |
| MS-MR | +++ | + | +++ | +++ | MR7C    MR7R |
| MS-SR | +++ | +++ | +++ | +++ | SR7 |

Biomass Concentration (direct filter counts)
− cells below detection limit (<1.2E3 cells/ml)
+ biomass observed at <5E4 cells/ml
++ biomass observed at 5E4 to 1E6 cells/ml
+++ biomass observed at >1E6 cells/ml
n.d. no data After the fourth passage (M4), individual strains were isolated by plating on LB agar. Colonies with unique morphologies were identified by 16S rRNA gene sequencing and taxonomic annotation (Table 5). In most cases (except Well 7+MS-MR, which enabled isolation of two strains of the same species), a single dominant strain was able to be isolated from specific combinations of media and inocula. One additional strain was isolated by LB agar colony culturing after M1 in MS+FM media with Well 4 fluids. 16S rRNA Blastn annotations of isolated strains are presented in Table 5. A 16S rRNA phylogenetic tree of McElmo Dome $CO_2$-passaged isolates and several closely related Bacilli is presented in FIG. 2.

in <6 months). Growth of *B. megaterium* SR7 and other strains was validated by triplicate incubation of spore stocks for 28-42 days using multiple media (Table 1). Growth was defined as demonstrating at least one order of magnitude increase in cell density relative to starting concentration (~$10^4$ spores/ml; Table 6).

TABLE 6

Summary of results from strain isolate $scCO_2$ incubations in pure culture

| Incubation | Duration | Strain | Media | Growth | Max cells/mL |
|---|---|---|---|---|---|
| P1 | 33 days | *B. megaterium* SR7 | SR | 1/2 | $1.0 \times 10^8$ |
| | | *B. licheniformis* MR4 | MR | 3/3 | $1.2 \times 10^8$ |
| | | *B. safensis* MR7C | MR | 1/3 | $8.1 \times 10^7$ |
| | | *B. safensis* MR7R | MR | 1/3 | $4.9 \times 10^7$ |
| | | *B. safensis* MR2 | MR | 1/2 | $8.8 \times 10^6$ |
| | | *B. safensis* FM4 | FM | 2/3 | $3.5 \times 10^7$ |
| P2 | 28 days | *B. megaterium* SR7 | SR | 1/3 | $2.0 \times 10^7$ |
| | | | LB | 3/3 | $6.8 \times 10^7$ |
| | | *B. licheniformis* MR4 | MR | 1/3 | $1.8 \times 10^6$ |
| | | | LB | 1/3 | $2.3 \times 10^7$ |
| | | *B. safensis* MR7C | MR | 1/3 | $1.5 \times 10^8$ |
| | | | LB | 1/3 | $4.4 \times 10^6$ |
| P3 | 42 days | *B. megaterium* SRT | LB | 3/3 | $3.5 \times 10^7$ |
| | | *B. safensis* MR2 | MR | 0/2 | $3.2 \times 10^4$ |
| | | | LB | 0/2 | $1.8 \times 10^4$ |
| | | *B. safensis* MR7R | MR | 1/3 | $1.9 \times 10^6$ |
| | | | LB | 1/3 | $6.3 \times 10^6$ |
| | | *B. safensis* FM4 | MR | 3/3 | $6.1 \times 10^7$ |
| | | | LB | 3/3 | $1.2 \times 10^7$ |

Based on the results from the original four rounds of enrichment passaging (M1-M4) and subsequent pure culture $scCO_2$ incubation trials from spore stocks (P1-P3), strain *B.*

TABLE 5

Summary of passaged isolate morphologies and taxonomic annotations

| Well Inocula | Passage Media | Colony Morphology | 16S rRNA Blastn Top Hit | Blastn ID % | Designated Strain Name |
|---|---|---|---|---|---|
| 2 | MS-MR | Circular, entire, umbonate, dull, cream, opaque | *Bacillus safensis* | 99 | *B. safensis* MR2 |
| 4 | MS-MR | Circular, filamentous, flat, dull, nonpigemented, translucent | *Bacillus licheniformis* | 99 | *B. licheniformis* MR4 |
| 4 | MS-FM | Circular, entire, umbonate, dull, cream, opaque | *Bacillus safensis* | 99 | *B. safensis* FM4 |
| 7 | MS-MR | Circular, entire, umbonate, dull, cream, opaque | *Bacillus safensis* | 100 | *B. safensis* MR7C |
| 7 | MS-MR | Circular, undulate, umbonate, dull, cream, opaque | *Bacillus safensis* | 99 | *B. safensis* MR7R |
| 7 | MS-SR | Circular, entire, convex, dull, white, opaque | *Bacillus megaterium* | 109 | *B. megaterium* SR7 |

Figure 2:
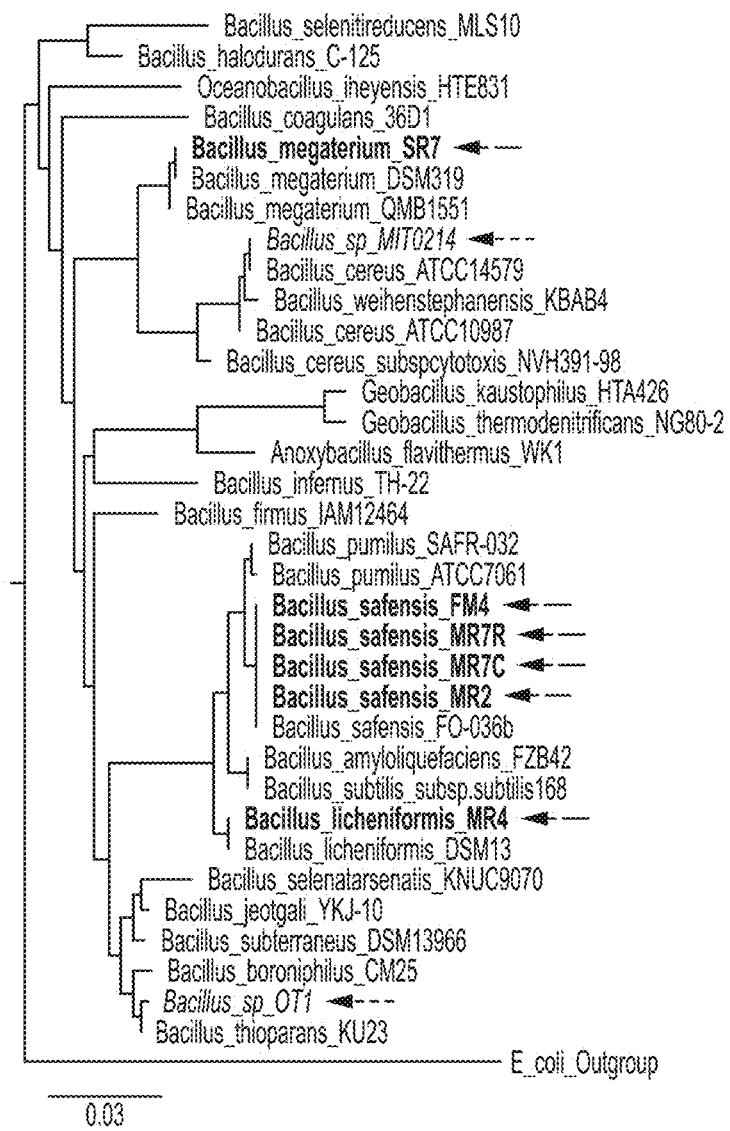
FIG. 2 shows a 16S rRNA phylogenetic tree of McElmo Dome isolates, isolates, and additional closely related Bacilli.

Because enrichment passaging led to the isolation of several strains demonstrating spore-like morphologies and annotated as spore-forming taxa, isolated strains were prepared as spores for long-term storage. Previous work by Peet et al., (2015) demonstrated that spores loaded into replicate reactors under an $scCO_2$ headspace (e.g., *Bacillus* sp. OT1, *Bacillus* sp. MIT0214; FIG. 2) grew with frequencies dependent on incubation time and starting spore concentrations, while vegetative cells were unable to survive $scCO_2$ exposure. Spore preparations of *B. megaterium* SR7 and *B. licheniformis* MR4 maintained consistent viability over long periods (>2 years) in spore prep wash buffer at 4° C., though all *B. safensis* strains demonstrated markedly lower survival (decrease of CFUs/ml by at least four orders of magnitude

*megaterium* SR7 generated the most consistently robust growth, especially in LB media (6/6 combined growth in P2-P3). Thus, strain *B. megaterium* SR7 was selected for physiological, metabolic and genomic investigation with the intent of optimizing growth under $scCO_2$. Isolates *B. licheniformis* MR4 and *B. safensis* FM4 also demonstrated strong growth during enrichment passaging and in pure culture.

Isolate SR7 Genomics

The genome of *B. megaterium* SR7 was sequenced to determine its metabolic capacity and enable the development of genetic manipulation tools for bioproduct pathway engineering. PacBio sequencing (Pacific Biosciences; Menlo Park, Calif.) and assembly resulted in six contigs (DNA fragments) from *B. megaterium* SR7 (Table 7).

TABLE 7

SR7 Summary of PacBio genome sequencing/assembly and RAST annotation statistics

| Contig | DNA Type | Length | % Bases Called | Coverage | ORFs | Plasmid-Association | Sporulation/Germination |
|---|---|---|---|---|---|---|---|
| 1 | Chromosome | 5449642 | 100.0 | 40.7 | 5,696 | 3 | 194 |
| 2 | Plasmid p1 | 21958 | 99.9 | 57.0 | 35 | 11 | 6 |
| 3 | Plasmid p2 | 17283 | 100.0 | 50.5 | 19 | 4 | 2 |
| 4 | Plasmid p3 | 9202 | 79.2 | 20.8 | 13 | 3 | 1 |
| 5 | Plasmid p4 | 7873 | 92.5 | 6.7 | 8 | 3 | 1 |
| 6 | Plasmid p5 | 2921 | 52.2 | 0.5 | 4 | 2 | 1 |

Figure 3:
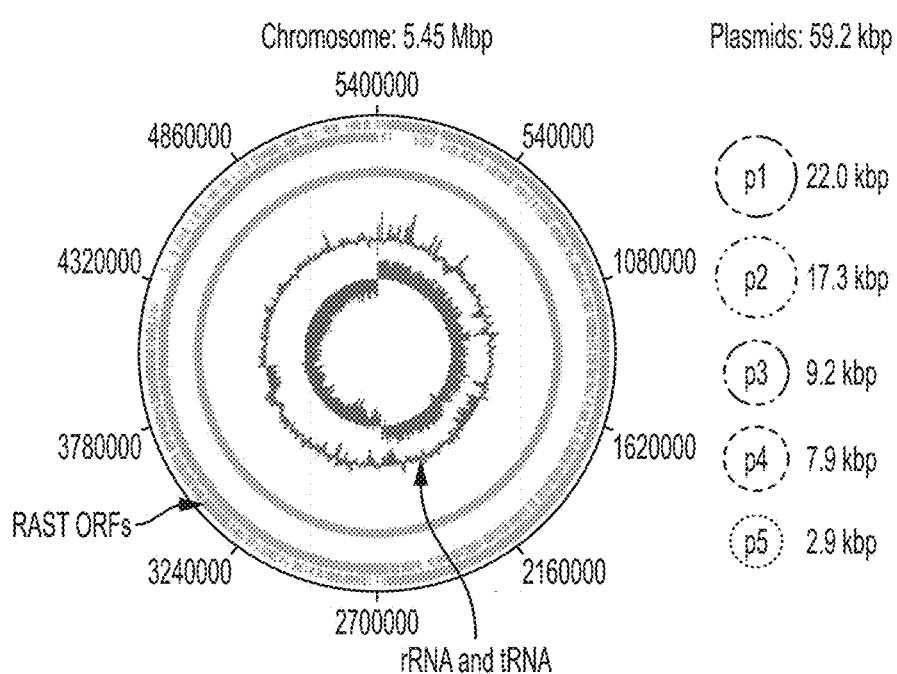
FIG. 3 shows a schematic of the *B. megaterium* SR7 5.51 Mbp genome, including the closed 5.45 Mbp chromosome. Concentric circles (outside in) are RAST ORFs, rRNA and tRNA, GC content, and GC skew. Asymmetry in GC skew indicates proper chromosome assembly. Circles at the right represent five putative plasmids native to SR7.

The largest contig is 5,449,642 bp with 40.7× coverage and 39% GC content, while the other five contigs are between 2.9 kb and 22.0 kb (Table 7). Comparison of SR7 contigs with reference B. megaterium strain QM_B1551 showed nearly 1:1 synteny of the largest SR7 contig and the main chromosome of QM B1551, as well as similarity between the smaller SR7 contigs and QM B1551 plasmids. After synteny-based adjustments enabled the SR7 chromosome to be closed (FIG. 3), it was submitted to RAST for functional annotation along with the five smaller contigs. RAST chromosome analysis called 5,696 coding ORFs, with 13 complete rRNA operons with 5S, 16S and 23S rRNA genes and one extra 5S rRNA gene.

Genomic annotations of carbon metabolism in B. megaterium SR7 include genes associated with glycolysis, the Entner-Doudoroff Pathway, TCA Cycle, Pentose Phosphate Pathway, Glyoxylate Bypass, and acetogenesis from pyruvate. Annotation of the SR7 chromosome also reveals the genomic potential for broad fermentative reactions, including utilization of glucose, fructose, mannose, and xylose, and the production of butyrate, lactate, butanol, acetate, 2,3-butanediol, and ethanol.

No genes associated with direct carbon fixation pathways were detected in the genome (e.g., Calvin Cycle, Wood-Ljungdahl Pathway, rTCA cycle, etc.). However, the annotation of carbonic anhydrase, which facilitates conversion of $CO_2$ to bicarbonate (Smith and Ferry, 2000), carbamoyl-phosphate synthase, which incorporates bicarbonate for pyrimidine and arginine biosynthesis (Arioli et al., 2009), and phosphoenolpyruvate carboxylase, which catalyzes the irreversible addition of bicarbonate to phosphoenolpyruvate, indicates the capacity for SR7 to utilize and assimilate $CO_2$ species, potentially as a mechanism for aiding in high $pCO_2$ exposure survival (Santillan et al., 2015, Arioli et al., 2009). The presence of carboxylase may prove useful for future engineering of $CO_2$-consuming metabolic pathways as a sustainable substrate in addition to solvent under $scCO_2$ conditions, especially in light of the previous demonstration of B. megaterium carboxylase activity under $scCO_2$ (Matsuda et al., 2001).

Annotated inorganic redox metabolism-associated genes may ultimately prove useful by informing growth media amendments or elucidating the capacity for SR7 to grow on alternative substrates, including treated wastewater, e.g., by denitrification (Yang et al., 2012), reducing the need for expensive carbohydrate substrates. B. megaterium SR7 genes of this nature include assimilatory sulfite reductase (NAPDH-dependent), sulfite oxidase, assimilatory nitrate reductase, dissimilatory nitrite reductase (nirBD), nitric oxide reductase denitrification genes (norQD), and an arsenate reductase detoxification gene (arsC). Physiological annotations of the B. megaterium SR7 chromosome that hold potential utility as components of a microbial bioproduction system include a full suite of sporulation genes, siderophore assembly and uptake, flagellar motility, the twin-arginine translocation (TAT) system, and PHB metabolism, the last of which indicates a capacity for redirecting flux toward concentrated storage of excess carbon. The endogenous TAT secretion system, may be useful for developing the ability to secrete specific products in the event that bioproduction focuses on the generation of proteins or enzymes.

Because the five smaller contigs failed to thoroughly annotate via RAST (i.e., a majority of hypothetical genes), RAST-called ORFs were submitted to Blastx for amino acid level annotation. All five contigs are annotated as containing plasmid replication, recombination, and mobility genes, as well as genes previously identified on other Bacillus spp. plasmids, and sporulation-related genes, content consistent with previously characterized B. megaterium plasmids (Eppinger et al., 2011). As a result, the five putative plasmids native to B. megaterium SR7 are designated (in order of decreasing size) plasmids p1 through p5, the RAST statistics and Blastx annotations for which are listed in Table 7. In comparison to the five putative plasmids in strain SR7 (59.2 kb total), seven (426 kb total) and three plasmids (91.3 kb total) were previously detected in strains QM B1551 and WSH-002, respectively, providing precedent for extra-chromosomal gene content in B. megaterium.

The B. megaterium SR7 genome size (5.51 Mbp) is slightly larger than several previously sequenced B. megaterium strains, including QM B1551 (5.1 Mbp) and DSM319 (5.1 Mbp), and approximately 33% larger than strain WSH-002 (4.14 Mbp). B. megaterium isolate SR7 and industrial strains QMB1551 and DSM319 share 96-97% average nucleotide identity (ANI). A comparison of shared gene content based on RAST annotations of B. megaterium SR7 and the three B. megaterium type strains reveal that approximately 12% of the SR7 genome consists of gene content not observed in three fully sequenced B. megaterium strains. However, the number of ORFs called by RAST appears to underestimate the number of gene calls in the original sequencing studies associated with each strain (e.g., DSM319 RAST=2,898 ORFs, Eppinger et al. (2011)=5,272 ORFs; QM B1551 RAST=2,915 ORFs, Eppinger et al., (2011)=5,284 ORFs; WSH-002 RAST=2,872 ORFs, Liu et al. (2011)=5,269 ORFs). According to the RAST re-annotation of these submitted genomes, genes unique to SR7 include a gas vesicle structural protein (gvpA), genes associated with biotin synthesis/regulation (bioHR), a carboxysome structural gene (ccmM), a cell wall teichoic acid glycosylation gene (gtcA), several phage annotations, and chromosome/plasmid partitioning genes (parAB).

Physiological Characterization of SR7 Under Ambient Conditions

Strain B. megaterium SR7 was subjected to chemical and temperature characterization experiments under an ambient atmosphere to establish conditional growth ranges and optima of facultative aerobic growth. The results of these assays are presented in Table 8. pH growth experiments revealed the fastest growth between pH 6-7 with an extended lag phase of 76 hours for pH 4 and 10, and no growth after 123 hours at pH 2 and pH 12. LB and Biolog salinity assays revealed diminished growth of SR7 above 10 g/l NaCl. Increasing bicarbonate above 100 mM also led to decreased growth. SR7 growth is supported between 23° C. and 45° C., with growth not observed after 73 hours at 9° C. and 55° C. Sensitivity to all tested antibiotics (with intermediate sensitivity to spectinomycin; Table 9) may be exploited for aspects of biotechnology development methods, including selective markers for transformations. Biolog assays (Biolog, Inc; Hayward, Calif.) revealed SR7 growth was also inhibited by D-serine and Niaproof 4, which are known to inhibit cell wall synthesis and emulsify lipid membranes, respectively.

TABLE 8

Summary of viable SR7 growth in LB media over chemical and temperature ranges under aerobic conditions

| Condition | Range | Optimal |
|---|---|---|
| pH$^a$ | 4-10 | 6-7 |
| [NaCl] (g/L)$^b$ | 0-100 | 0-10 |
| NaHCO$_3$ (mM)$^c$ | 0-300 | 0-100 |
| Temperature (° C.)$^d$ | 23-45 | 37 |

Assayed ranges and durations:
$^a$pH: 2, 4, 6, 7, 8, 10, 12 over 123 h
$^b$Salinity: 0, 5, 10, 50, 80, 100 g/L over 36 h
$^c$Bicarbonate: 0, 100, 300, 500 mM over 36 h
$^d$Temperature: 9, 23, 27, 30, 37, 45, 55° C. over 73 h

TABLE 9

B. megaterium SR7 antibiotic sensitivity assay summary

| Antibiotic | $^a$ug/mL | $^b$% Control | Assay | $^c$Sensitivity |
|---|---|---|---|---|
| Spectinomycin | 100 | 47% | LB | S/R |
| Nalidixic Acid | — | 14% | Biolog | S |
| Tetracycline | 1.5 | 11% | LB | S |
| Minocycline | — | 11% | Biolog | S |
| Lincomycin | — | 11% | Biolog | S |
| Rifamycin SV | — | 11% | Biolog | S |
| Aztreonam | — | 10% | Biolog | S |
| Vancomycin | — | 10% | Biolog | S |
| Streptomycin | 10 | 10% | LB | S |
| $^d$D-Serine | — | 10% | Biolog | S |
| Fusidic Acid | — | 9% | Biolog | S |
| dNiaproof 4 | — | 9% | Biolog | S |
| Chloramphenicol | 35 | 9% | LB | S |
| Kanamycin | 5 | 9% | LB | S |
| Troleandomycin | — | 9% | Biolog | S |
| Ampicilin | 50 | 8% | LB | S |

$^a$Biolog does not publish antibiotic concentrations
$^b$(OD$_{600}$ AB/OD$_{600}$ Control)*100 in LB, average n = 2 (OD$_{490}$ AB/OD$_{490}$ Control)*100 for Biolog, average n = 2
$^c$S = sensitive, R = resistant
$^d$Non-antibiotic treatment Biolog assays also established which potential sole carbon sources may be useful in future B. megaterium SR7 culturing and allowed comparison between B. megaterium SR7 and closely related B. megaterium strains DSM319 and QM B1551. While all three strains demonstrated robust growth on TCA Cycle intermediates citric acid and L-malic acid, DSM319 and QM B1551 both grew on L-lactic acid and L-glutamic acid, while SR7 did not (Table 10).

TABLE 10

B. megaterium SR7 and alternative B. megaterium strains categorized by robust (+++), marginal (+) or no (−) growth on Biolog sole carbon sources (no metals added). Only carbon sources enabling at least one strain to demonstrate robust growth are listed

| Carbon Substrate | SR7 | DSM319 | QM B1551 |
|---|---|---|---|
| Citric Acid | +++ | +++ | +++ |
| L-Malic Acid | +++ | +++ | +++ |
| L-Lactic Acid | + | +++ | +++ |
| L-Glutamic Acid | + | +++ | +++ |
| α-D-Glucose | + | +++ | + |
| Dextrin | + | +++ | + |
| D-Mannitol | + | +++ | + |
| D-Gluconic Acid | + | +++ | + |
| L-Aspartic Acid | + | +++ | + |
| N-Acetyl-D-Glucosamine | + | +++ | + |
| L-Histidine | + | +++ | + |
| Bromo-Succinic Acid | + | +++ | + |
| D-Maltose | − | +++ | + |
| Sucrose | − | +++ | + |
| β-Hydroxy-D,L-Butyric Acid | + | + | +++ |
| D-Saccharic Acid | − | − | +++ |

B. megaterium SR7 growth was markedly increased upon addition of trace metals solution to Biolog media (Table 11), including on substrates D-raffinose, α-D-glucose, γ-aminobutyric acid, myo-inositol, L-arginine, D-gluconic Acid, citric acid, N-acetyl-D-glucosamine, L-glutamic acid, D-turanose, and L-pyroglutamic acid. Malic acid appears to have facilitated robust growth only in the absence of metals. B. megaterium SR7 was able to grow on several carbon sources in the presence of metals that strains B. megaterium DSM319 and QM B1551 grew on without amendment (e.g., L-glutamic acid, α-D-glucose, sucrose, N-acetyl-D-glucosamine, etc.), which suggests that metal-bearing co-factors specific to B. megaterium SR7 catabolism may require elevated metals concentrations to properly function. Initially, B. megaterium SR7 demonstrated robust growth on 2/71 Biolog substrates, improving to 12/71 upon addition of metals. These 12 substrates have thus been identified as potential sole carbon sources for metals-amended defined media.

TABLE 11

B. megaterium SR7 robust (+++), marginal (+) and no (−) growth in unamended (I & II) and trace metals-amended carbon source Biolog plates. Maximum growth for each plate trial is noted by an asterisk. All substrates (and negative control) listed.

| Carbon Substrate | I | II | +Metals | Carbon Substrate | I | II | +Metals |
|---|---|---|---|---|---|---|---|
| Citric Acid | +++ | +++* | +++ | D-Trehalose | − | + | + |
| α-D-Glucose | + | + | +++ | β-Methyl-D-Glucoside | − | + | + |
| L-Arginine | + | + | +++ | | | | |

TABLE 11-continued

*B. megaterium* SR7 robust (+++), marginal (+) and no (−) growth in unamended (I & II) and trace metals-amended carbon source Biolog plates. Maximum growth for each plate trial is noted by an asterisk. All substrates (and negative control) listed.

| Carbon Substrate | I | II | +Metals | Carbon Substrate | I | II | +Metals |
|---|---|---|---|---|---|---|---|
| D-Gluconic Acid | + | + | +++ | Sucrose | − | + | + |
| L-Aspartic Acid | + | + | +++ | Inosine | − | + | + |
| N-Acetyl-D-Glucosamine | + | + | +++* | D-Sorbitol | + | − | + |
|  |  |  |  | 3-Methyl Glucose | − | − | + |
| L-Glutamic Acid | + | + | +++ | D-Glucuronic Acid | + | + | − |
| D-Turanose | + | + | +++ | Acetic Acid | + | + | − |
| L-Pyroglutamic Acid | + | + | +++ | L-Serine | + | + | − |
| D-Raffinose | − | + | +++ | Tween 40 | − | + | − |
| Y-Amino-Butryric Acid | − | + | +++ | D-Galacturonic Acid | − | + | − |
|  |  |  |  | L-Galactonic Acid Lactone | − | + | − |
| myo-Inositol | − | + | +++ |  |  |  |  |
| L-Malic Acid | +++* | +++ | + | Acetoacetic Acid | − | + | − |
| Gelatin | + | + | + | Mucic Acid | − | + | − |
| Pectin | + | + | + | Propionic Acid | − | + | − |
| Dextrin | + | + | + | Quinic Acid | − | + | − |
| α-D-Lactose | + | + | + | D-Saccharic Acid | − | + | − |
| D-Mannitol | + | + | + | D-Fructose-6-PO4 | + | − | − |
| Methyl Pyruvate | + | + | + | N-Acetyl-D-Galactosamine | + | − | − |
| D-Melibiose | + | + | + |  |  |  |  |
| D-Fructose | + | + | + | Formic Acid | + | − | − |
| D-Arabitol | + | + | + | Negative Control | − | − | − |
| L-Alanine | + | + | + | p-Hydroxy-Phenylacetic Acid | − | − | − |
| D-Lactic Acid Methyl Ester | + | + | + |  |  |  |  |
|  |  |  |  | D-Mannose | − | − | − |
| D-Galactose | + | + | + | Glycyl-L-Proline | − | − | − |
| L-Lactic Acid | + | + | + | α-Hydroxy-Butyric Acid | − | − | − |
| β-Hydroxy-D,L-Butyric Acid | + | + | + |  |  |  |  |
|  |  |  |  | α-Keto-Butyric Acid | − | − | − |
| D-Cellobiose | + | + | + | D-Fucose | − | − | − |
| D-Salicin | + | + | + | D-Glucose-6-PO4 | − | − | − |
| Glycerol | + | + | + | Glucuronamide | − | − | − |
| Gentiobiose | + | + | + | N-Acetyl-β-D-Mannosamine | − | − | − |
| α-Keto-Glutaric Acid | + | + | + |  |  |  |  |
| L-Histidine | + | + | + | L-Fucose | − | − | − |
| Stachyose | + | + | + | D-Malic Acid | − | − | − |
| Bromo-Succinic Acid | + | + | + | L-Rhamnose | − | − | − |
| D-Maltose | − | + | + | D-Aspartic Acid | − | − | − |
|  |  |  |  | N-Acetyl Neuraminic Acid | − | − | − |
|  |  |  |  | D-Serine | − | − | − |

*B. megaterium* SR7 Activity Under 1 Atm $CO_2$

As described in the Methods, culturing experiments under 1 atm $CO_2$ were used as a proxy for $scCO_2$ conditions. Modeling using the ideal gas law indicates that for rich media, predicted dissolved $CO_2$ concentrations for ambient air, 1 atm $CO_2$, and $scCO_2$ are $1.2 \times 10^{-5}$ M, $2.6 \times 10^{-2}$ M and 2.7 M, respectively (Peet et al., 2015). Therefore, exposure of SR7 cultures to intermediate dissolved $CO_2$ content and pH conditions at 1 atm $CO_2$ may inform beneficial process improvements for enhanced growth under $scCO_2$.

Growth Dynamics and Process Engineering

Figure 4A:
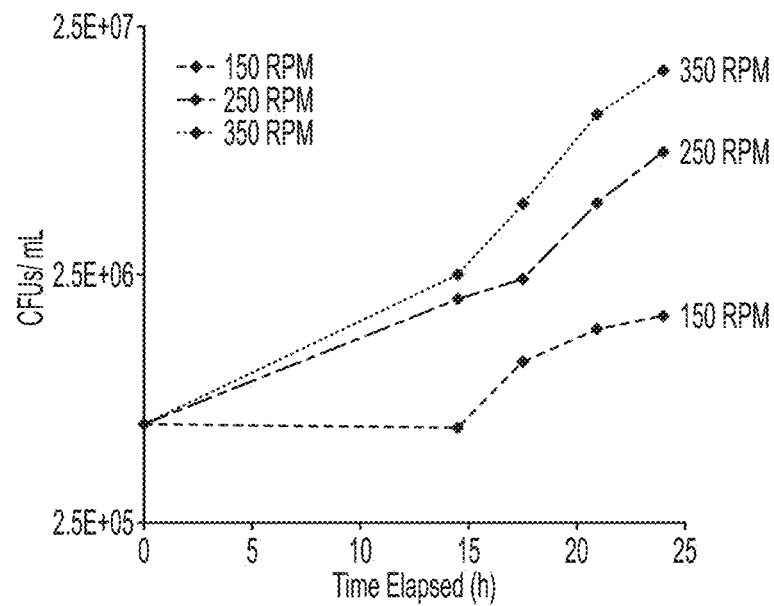
FIGS. 4A and 4B show the effect of mixing rates on *B. megaterium* SR7 spore germination in LB under 1 atm $CO_2$ as measured by CFU/mL (FIG. 4A) and OD600 (FIG. 4B).
Figure 4B:
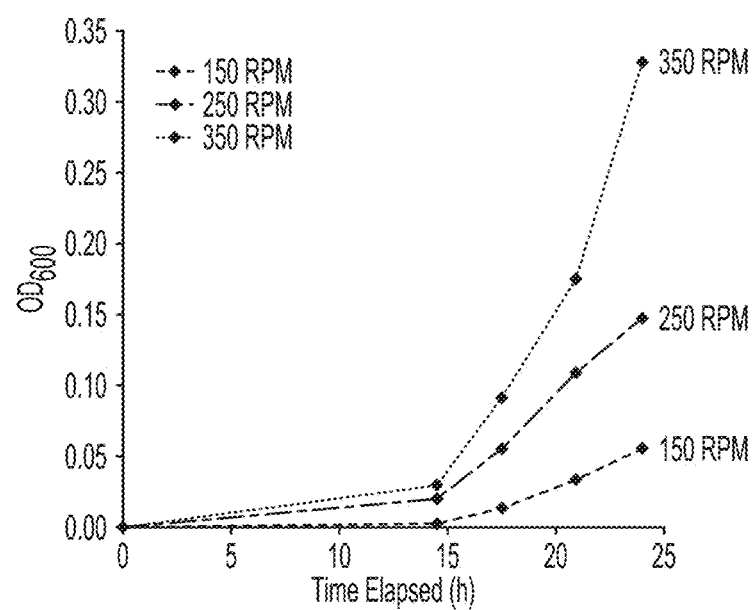
Figure 5A:
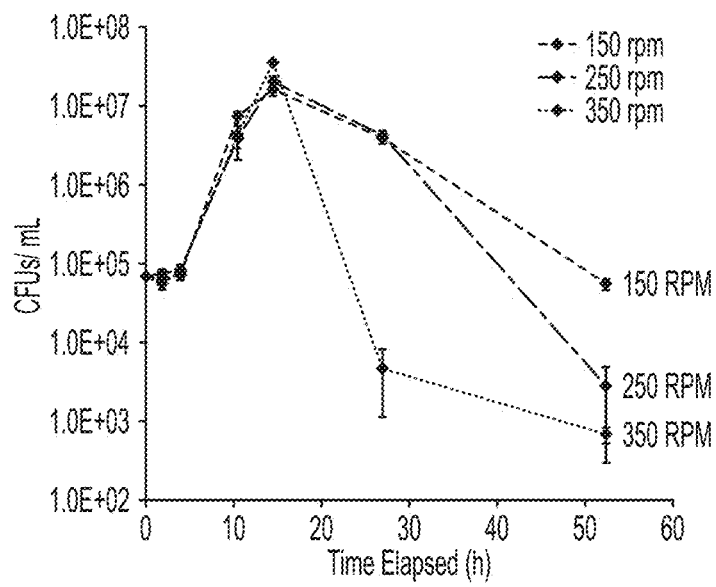
FIGS. 5A and 5B show the effect of mixing rates on passaged *B. megaterium* SR7 vegetative growth in LB under 1 atm $CO_2$ as measured by CFU/mL (FIG. 5A) and OD600 (FIG. 5B).
Figure 5B:
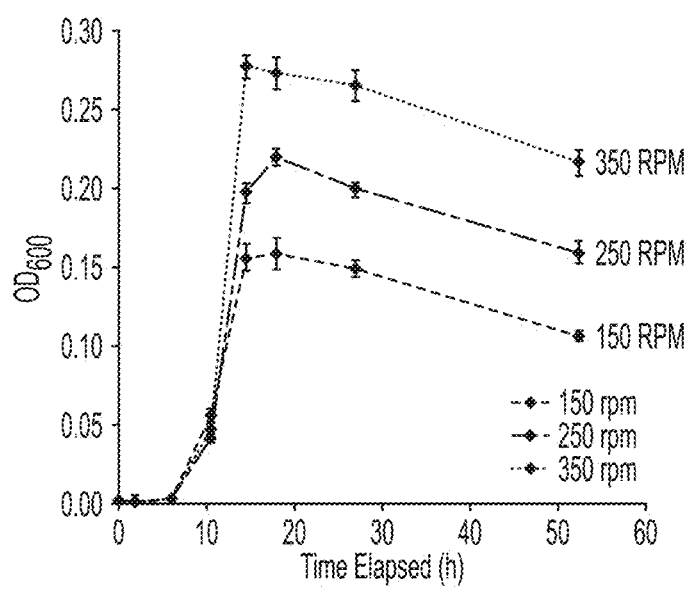

Assays conducted at 1 atm $CO_2$ showed that increased shake speed led to faster cell growth in spore-inoculated cultures (FIG. 4) and also facilitated more rapid growth of passaged vegetative cells (FIGS. 5A and 5B).

Increased shake speeds also enabled higher biomass accumulation, as the maximum OD600 reached by 150 and 250 rpm samples were 57% and 79% the OD600 maximum for 350 rpm, while maximum CFU counts reached by 150 rpm ($1.5 \times 10^7$ CFUs/ml) and 250 rpm ($1.8 \times 10^7$ CFUs/ml) samples were 43% and 51% of the maximum count for 350 rpm ($3.5 \times 10^7$ CFUs/ml), respectively (FIGS. 5A and 5B). However, it appears that cultures that reach maximum biomass accumulation due to increased mixing rates also may reach stationary phase and crash more quickly, a result often associated with end product toxicity in fermenting cultures (FIG. 5A). Therefore, due to the accelerated growth rate of *B. megaterium* SR7 at 250 RPM and the ability to sustain high biomass without experiencing a precipitous drop in CFU counts (as with 350 rpm), a shake speed of 250 RPM was utilized for all subsequent incubation experiments.

Minimal Medium Formulation (M9+)

Figure 6A:
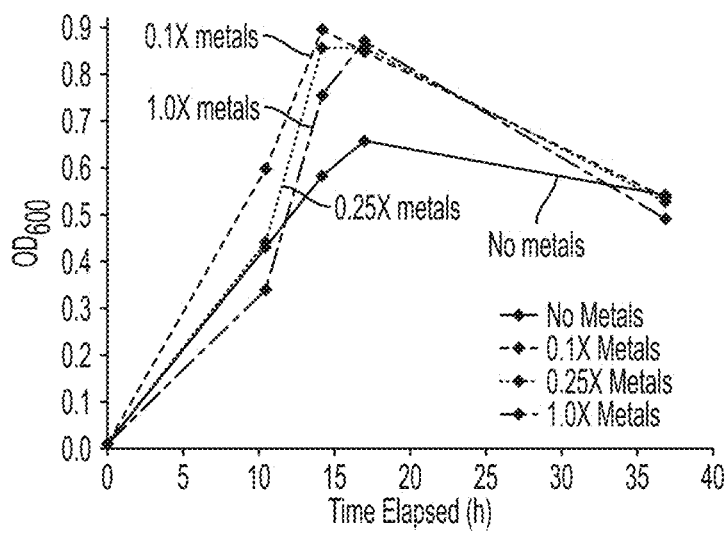
FIGS. 6A and 6B show *B. megaterium* SR7 growth under 1 atm $CO_2$ at 37° C. as a function of trace metals solution concentration (FIG. 6A) and in the presence (filled diamonds) and absence (open diamonds) of trace metals in M9 media types and unamended LB (black filled triangles) (FIG. 6B).
Figure 6B:
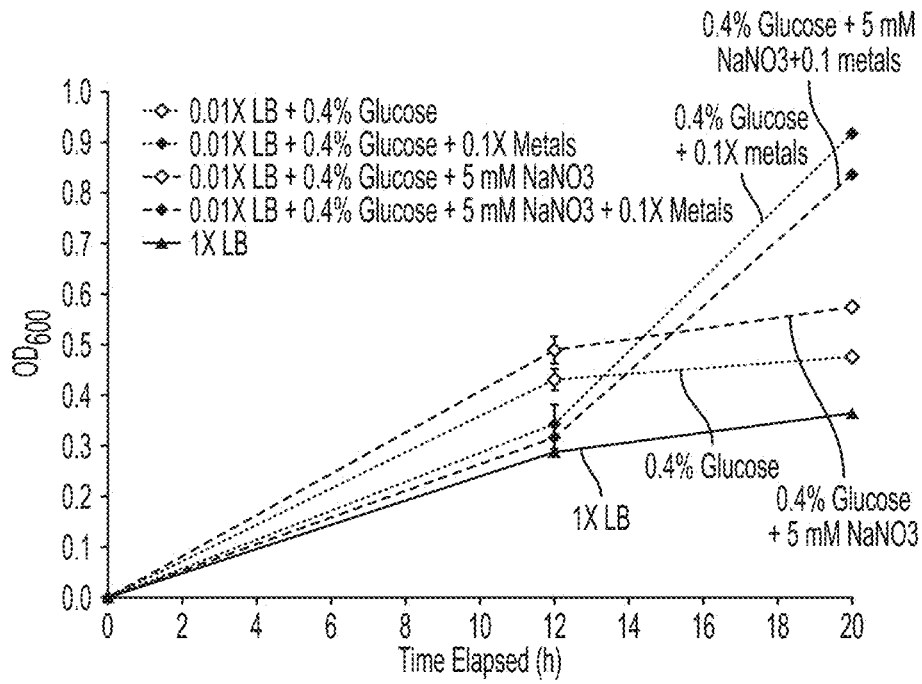

Development of a minimal growth medium enables examination of microbial physiology, determination of nutritional growth requirements, and holds potential to reveal the metabolic pathways through which carbon flux occurs during growth under various conditions. Initial attempts to grow *B. megaterium* SR7 in M9 base medium under 1 atm $CO_2$ with 0.4% glucose or 0.4% xylose as sole carbon source in the presence and absence of a trace metals solution were unsuccessful (Table 12). Subsequent growth assays revealed that both a de facto vitamin/co-factor supplement (e.g., dilute LB/YE at concentrations insufficient to independently support observable growth) and trace metals solution in glucose-amended media enabled robust growth (Table 12; FIGS. 6A and 6B). The use of NO3- as a potential alternative electron acceptor did not demonstrate any pronounced effects on growth rates or biomass accumulation, despite genomic evidence for potential nitrate/nitrite reduction capacity. Due to potential conflicts between xylose-induced biomass accumulation and heterologous gene expression, media development proceeded with glucose as sole carbon source. Since substituting out 0.01× LB for 0.01×YE (e.g., 1× is the concentration of YE present in LB, 5 g/l; 0.01×YE=50 mg/l) generated similar outcomes, media development proceeded with YE due to its more defined nature.

TABLE 12

M9 supplemented growth outcomes under 1 atm $CO_2$

| M9 Amendments | Growth |
|---|---|
| 0.4% Glucose | − |
| 0.4% Xylose | − |
| 0.4% Glucose + 1 X Metals | − |
| 0.4% Xylose + 1 X Metals | − |
| 0.001 X LB | − |
| 0.01 X LB | − |
| 0.001 X YE | − |
| 0.01 X YE | − |
| 0.001 X LB + 0.4% Glucose | + |
| 0.01 X LB + 0.4% Glucose | + |
| 0.01 X YE + 0.4% Glucose | + |
| 0.01 X YE + 0.4% Glucose + 5 mM $NaNO_3$ | + |
| 0.001 X LB + 0.4% Glucose + 5 mM Na $NO_3$ | + |
| 0.01 X LB + 0.4% Glucose + 5 mM $NaNO_3$ | + |
| 0.001 X LB + 0.4% Glucose + 0.1 X Metals | +++ |
| 0.01 X LB + 0.4% Glucose + 0.1 X Metals | +++ |
| 0.01 X YE + 0.4% Glucose + 0.1 X Metals | +++ |
| 0.01 X YE + 0.4% Glucose + 0.25 X Metals | +++ |
| 0.01 X YE + 0.4% Glucose + 1 X Metals | +++ |
| 0.01 X LB + 0.4% Glucose + 5 mM $NaNO_3$ + 0.1 X Metals | +++ |
| 0.01 X YE + 0.4% Glucose + 5 mM $NaNO_3$ + 0.1 X Metals | +++ |
| LB/Yeast Extract (YE) Dilutions | |
| 0.01 X LB = 100 mg/L tryptone, 50 mg/L YE, 100 mg/L NaCl | |
| 0.001 X LB = 10 mg/L tryptone, mg/L YE, 10 mg/L NaCl | |
| 0.01 X YE = 50 mg/L | |
| 0.001 X YE = 5 mg/L | |

0.1× trace metals solution proved the most effective concentration for enabling rapid growth of passaged vegetative cultures. Although 1 atm $CO_2$ passaged cultures in M9+0.4% glucose+0.01×YE amended with 0.25× and 1.0× trace metals achieved the same maximum OD600 as 0.1× metals-amended cultures, lower OD600 values at intermediate time points suggested diminished growth rates relative to 0.1× metals (FIG. 6A). Further investigation revealed that while cultures in the presence and absence of 0.1× trace metals reach intermediate OD600 values at approximately the same rate, metals-amended cultures continue to grow while non-amended cultures appear to enter stationary phase (FIG. 6B). The effect of trace metals on accelerated anaerobic growth has previously been observed in (David et al., 2010), who suggested that bacteria require metal co-factors to improve growth outcomes.

Figure 7A:
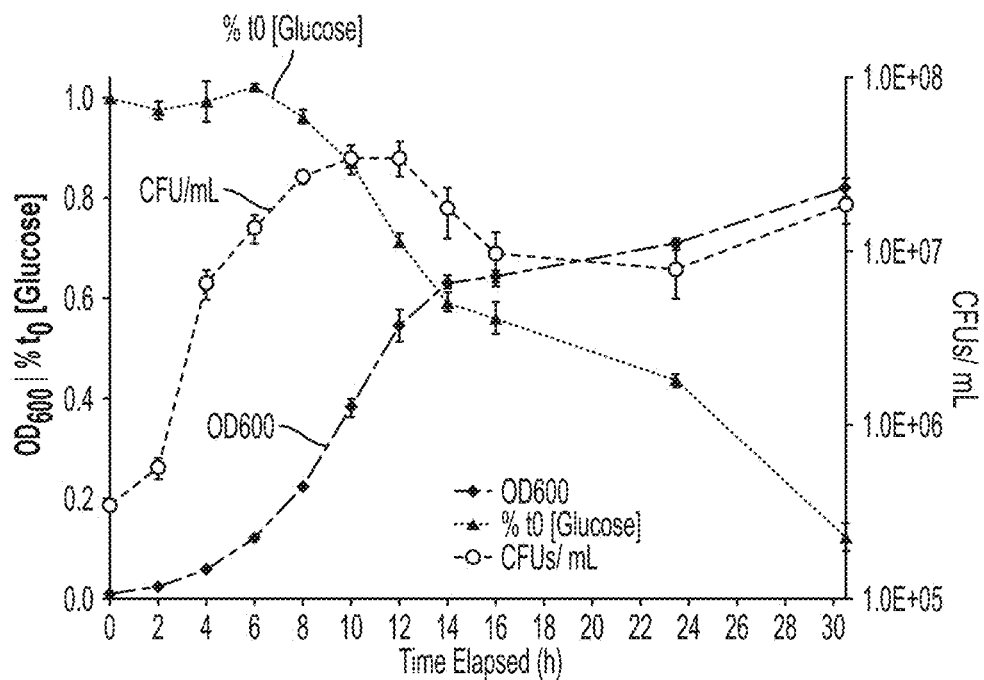
FIGS. 7A and 7B show *B. megaterium* SR7 growth dynamics under 1 atm $CO_2$, 37° C., 250 rpm and glucose consumption in M9+ media (FIG. 7A) and LB (FIG. 7B).
Figure 7B:
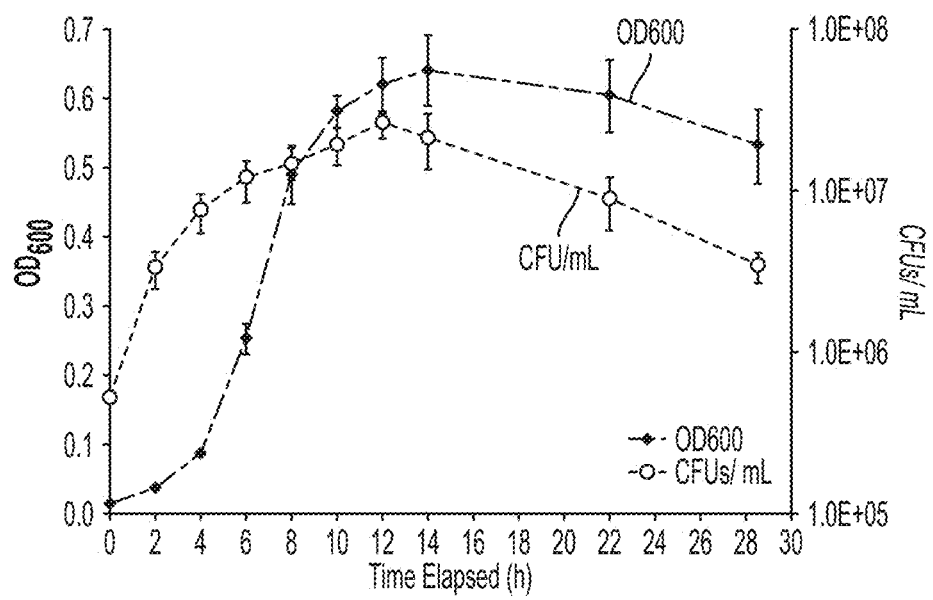

The final combination of M9+0.01×YE+0.1× metals+ 0.4% glucose is designated "M9+" medium, and was used as the base semi-defined minimal medium for all subsequent sole carbon source experiments. After establishing M9+ medium components, 1 atm $CO_2$ growth curves conducted in both M9+ and LB media revealed SR7 anaerobic doubling times based on OD600 of 1.93±0.1 h and 2.07±0.1 h, respectively (FIGS. 7A and 7B). $OD_{600}$ values and glucose consumption for M9+ media incubations appear to indicate log phase growth, then a brief stationary phase, followed by steady increases in OD and glucose consumption (though a decrease in CFUs).

Figure 8A:
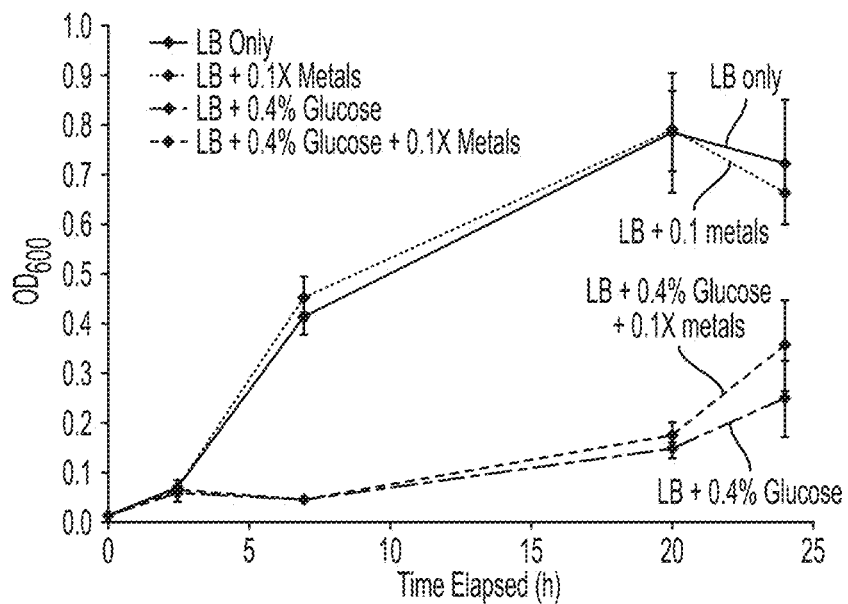
FIGS. 8A and 8B show *B. megaterium* SR7 cultures in LB under 1 atm $CO_2$, 37° C., 250 rpm show a lag phase when glucose-amended, as measured by OD600 (FIG. 8A) and incomplete glucose consumption after 24 hours (FIG. 8B).
Figure 8B:
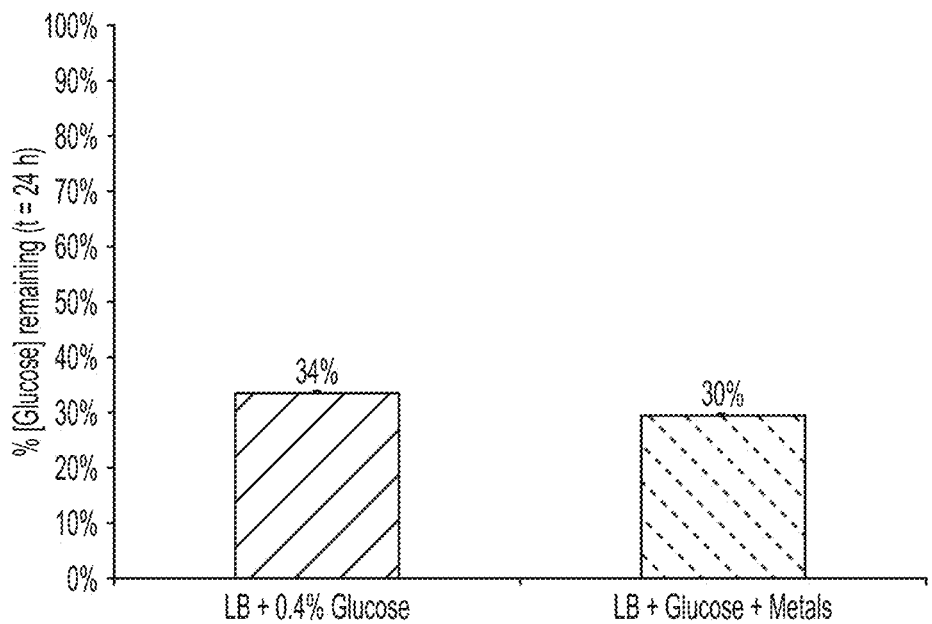

Despite positive growth on glucose as a sole carbon source in M9+ defined medium, B. megaterium SR7 showed a reduced growth rate under the same culturing conditions in LB supplemented with 0.4% glucose, including both with and without metals solution, as demonstrated by an extended lag (FIG. 8A). Similar results were generated under aerobic conditions (data not shown). Incomplete glucose consumption after 24 hours (30-34% glucose remaining; FIG. 8B) further indicates that LB-amended glucose is not fully utilized either due to growth on an alternative substrate (e.g., dilute YE or tryptone), or because glucose consumption during growth in LB medium is generating a toxic concentration of metabolites. Evidence from aerobic cultures demonstrate that after 2-3 hours, B. megaterium SR7 accumulates and maintains ~0.6 g/l acetate, while LB only cultures accumulate 0.4-0.5 g/l acetate after 5 hours, at which point it is consumed as a substrate (data not shown). These results suggest a potential mechanism for growth inhibition by glucose-associated end product toxicity as well as glucose repression of acetate re-assimilation. Inspection by phase contrast light microscopy of B. megaterium SR7 grown in LB+0.4% glucose under 1 atm $CO_2$ appears to show an increase in PHB granules (FIG. 9; polyhydroxybutyrates (PHBs). The membranes of many other cells appear to be nearly completely degraded, causing cells to look completely transparent. Because previous studies have shown high production of PHBs do not have a toxic effect on B. megaterium (Rodriguez-Contreras et al., 2013) it is considered unlikely that PHB accumulation itself is disrupting metabolism or cellular integrity.

Figure 10B:
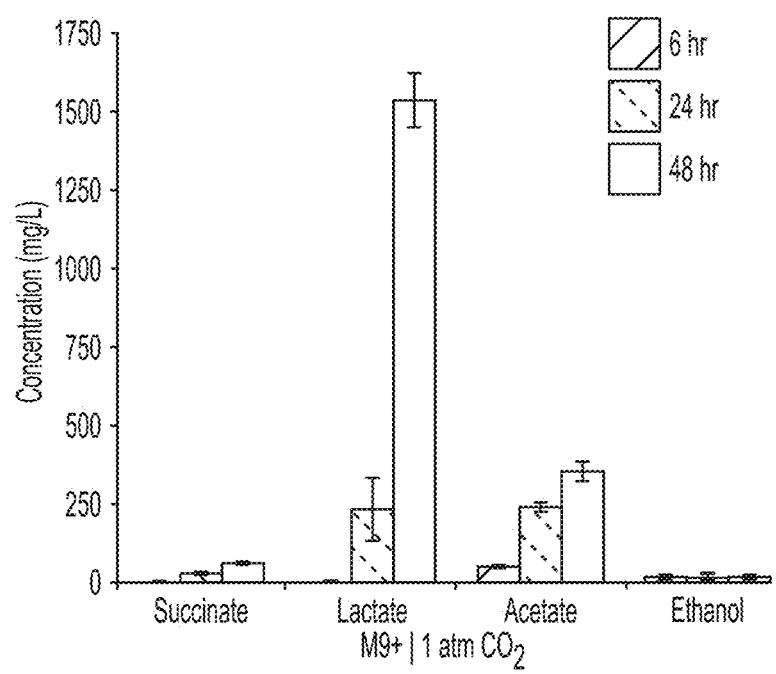

SR7 cultures incubated under 1 atm $CO_2$ in M9+ and LB media generated a variety of fermentative products detected by HPLC (FIG. 10). After 6 hours, cultures in both media generated acetate (LB: 271 mg/L; M9+: 49 mg/L) while LB cultures also generated TCA intermediate succinate (300 mg/L), possibly due to availability of more complex proteinaceous substrates. After 48-hour incubations in M9+ medium, SR7 continued to generate acetate (352 mg/L), while also generating large amounts of lactate (1.54 g/L), and low concentrations of succinate (62 mg/L) and ethanol (17 mg/L). In contrast, 48-hour incubations under 1 atm $CO_2$ in LB medium generated a metabolite profile constrained only to succinate (1.11 g/L) and acetate (235 g/L), which indicates alternative carbon utilization absent lactic acid fermentation. No additional volatile products (e.g., isobutanol, isopentanol, phenethyl alcohol) were detected by gas chromatography at any sub-sampled time points.

B. megaterium SR7 Germination Induction

Figure 11:
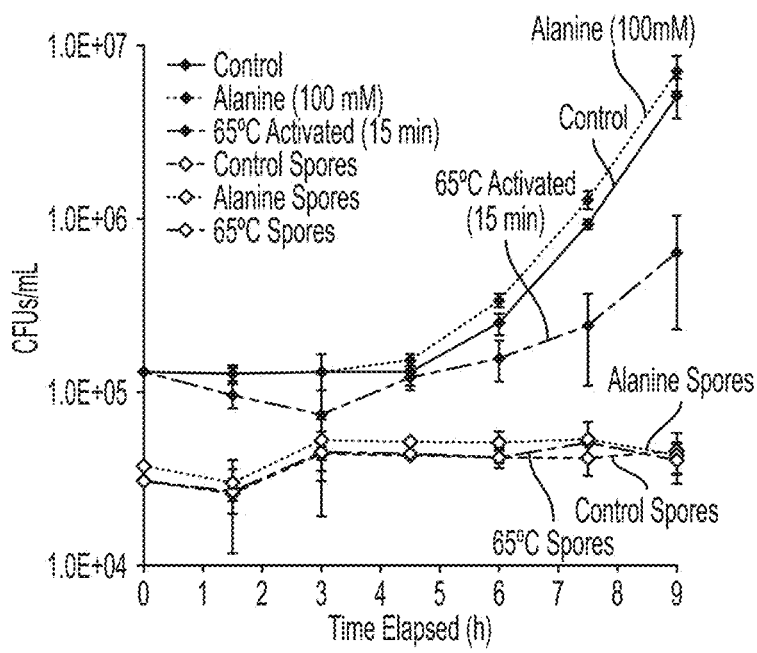
FIG. 11 shows germination of SR7 spores under 1 atm $CO_2$ in LB media, 100 mM L-alanine-amended LB, and LB heated at 65° C. for 10 minutes. Open triangles represent viable spore counts based on heat-killed (80° C. for 15 minutes) CFU counts.

Because germination and growth of spores under $scCO_2$ conditions has previously been shown to be a stochastic process (Peet et al., 2015), an effort was made to improve germination rates during $scCO_2$ incubations in order to be able to express heterologous enzymes more quickly and consistently. The literature has shown that a broad array of compounds, including several L-amino acids, and peptidoglycan are able to induce metabolically dormant endospores to germinate (Wei et al., 2010). These inducers have to be shown to activate germination in Bacillus through several independent pathways (Hyatt and Levinson, 1962). Two amino acids (L-alanine and L-leucine) previously shown to induce germination through different pathways were chosen for investigation with B. megaterium SR7 to increase the likelihood of success in an uncharacterized strain. Initial assays in LB under 1 atm $CO_2$ as a proxy for $scCO_2$ conditions demonstrated that L-alanine-amended cultures germinated by 4.5 hours, while unamended cultures grew between 4.5 and 6 hours after inoculation (FIG. 11).

After germination, growth occurs at nearly identical doubling times by OD600 (M9A+: 0.86 h; M9+: 0.89 h), suggesting that the effect of alanine is specific to the germination process rather than improved growth rates. Heat treatment reduced *B. megaterium* SR7 germination (marginal growth at 6 hours) rates and increased doubling times (1.11 h), despite previously being shown to induce spore germination spores for certain *Bacillus* species (Hyatt and Levinson, 1962). It is possible though that in the case of *B. megaterium* SR7, rather than inducing germination, the heat treatment is lethal to a sub-population of spores, decreasing the number of viable spores available to germinate and grow. During the initial period of vegetative outgrowth spore concentrations remain nearly constant (FIG. 11). As a result, it appears that individual spores or sub-populations will germinate and commence vegetative growth while remaining spores stay dormant, at least initially. Therefore, adding an inducer such as L-alanine provides a consistent source of growth potential to a pool of dormant cells.

Because phosphate buffered saline (PBS) solution does not have an available carbon source, spore-inoculated PBS cultures with inducer amendments under 1 atm $CO_2$ headspace enabled investigation of the anaerobic germination process independent of growth. Results assayed by fluorescence microscopy, bulk fluorescence and OD600 demonstrate that germination is induced by 3 hours, including with 100 and 250 mM L-alanine, 25 mM L-leucine and heat-treated 100 mM L-alanine (FIGS. 1 and 12). All incubated cultures showed an approximate 2-fold increase (1.9-2.1-fold) in fluorescence magnitude after 3 hours, eventually reaching a maximum at the 8.5 hour endpoint of 2.4-fold the bulk fluorescence (100 mM L-alanine) of PBS only incubated spores. By 24 hours, every inducer-amended sample also had a lower OD600 than unamended PBS samples, indicative of the flooding of the spore interior after spore coat degradation, decreasing the cell's index of refraction.

Figure 12A:
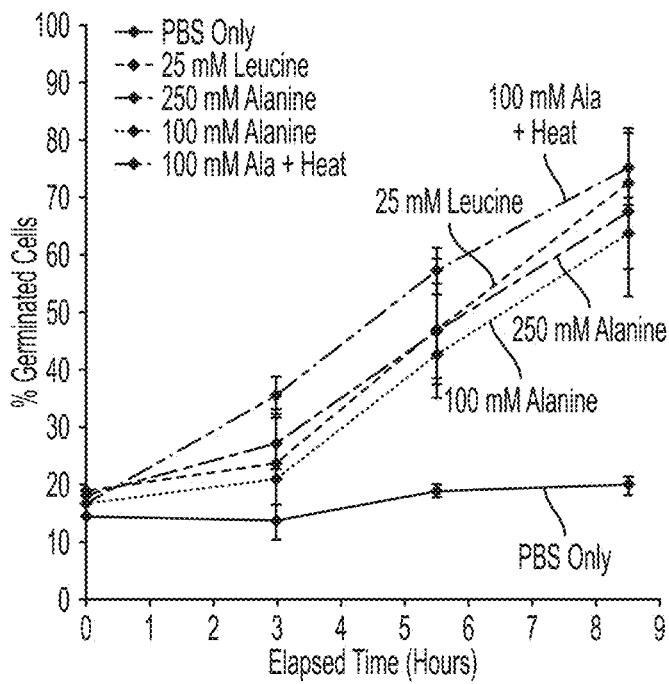

A similarly pronounced inducer effect was observed by fluorescence microscopy direct filter counts based on spore staining patterns indicative of dormancy and germination. All treatments increased the percentage of germinated cells by 3 hours relative to PBS incubated spores (FIG. 12). According to filter counts, unamended PBS incubated spores maintained a constant, low-level abundance of germinated cells, increasing from 14.7% germinated at t0, to 19.8% at 8.5 hours. Inducer-treated cultures increase more substantially, from 16.7-18.9% at t0 to 63.8-75.1% at 8.5 hours. Since all cells that showed stain membrane penetration, including whole cell and center-localized (FIG. 1), were considered "germinated," it is possible that "percentage germination" values in FIG. 12A may be overestimates. Microscopic inspection of inducer-amended PBS incubations did not reveal any vegetative cell morphologies, suggesting that L-alanine and L-leucine are not being utilized as a carbon source for growth in PBS.

The effect of heat treatment on PBS cultured spores (also amended with 100 mM L-alanine) generated mixed results. After initially increasing in bulk fluorescence, heat-treated cultures steadily decreased in bulk fluorescence, while microscopy indicated that heat treatment increased germination to the highest observed frequencies (FIG. 12A). However, this result may be due to spore coat damage during heat treatment at 70° C. that caused more cells to become susceptible to membrane penetration by Syto9 cell stain. Therefore, without further physical evidence it is difficult to conclude whether the apparent germination inducing effect by heat treatment is a genuine result or false positive.

Delayed germination induction experiments in which spores incubated under 1 atm $CO_2$ for 14.5 hours in PBS were amended with L-alanine or L-leucine and assayed for germination after 9.5 hours demonstrated the capacity to actively germinate in the presence of inducers mid-culture. Higher concentrations of L-alanine and L-leucine did not appear to improve the extent of germination relative to lower concentrations, suggesting that the capacity for SR7 spores to be germinated saturates at or below 100 mM L-alanine and 10 mM L-leucine. The observed effects caused by both amino acid inducers were comparable in magnitude (Table 13). Follow-up investigation of a physiological state change in endospores caused by alanine amendment to carbon-free PBS cultures was ultimately verified by use of FCM, as explained below in section "Physiological signatures of induced germination."

TABLE 13

Germination assays 9.5 hours after delayed induction in PBS under 1 atm $CO_2$ (OD decrease indicative of germination)

| Inducer | mM | Fluorescence Fold Increase | $OD_{600}$ Fold Decrease |
|---|---|---|---|
| L-alanine | 250 | 1.4 | 1.2 |
|  | 100 | 1.4 | 1.2 |
|  | 25 | 2.1 | 1.5 |
| L-leucine | 25 | 2.0 | 1.2 |
|  | 10 | 2.0 | 1.2 |

Physiological Signatures of Induced Spore Germination

Additional investigation using flow cytometry (FCM) sought to build upon preliminary LB-based evidence (FIGS. 11, 12A and 12B; Table 13) to verify a physiological effect of alanine on spores during the transition from dormant to germinated cell. FCM data collected on Syto16-stained SR7 cells from unamended and L-alanine-amended PBS cultures revealed two populations capable of gating on side and forward scatter (FIG. 14): 1) PBS only incubated cells (Population 1) and 2) L-alanine-amended PBS cells (Population 2). Based on Syto16 and propidium iodide (PI) fluorescence intensities, three additional populations could subsequently be gated based on unique Syto16 and propidium iodide (PI) fluorescence signatures. These individual populations appear well correlated with visual evidence by fluorescence microscopy of three staining patterns of varying intensity (whole cell, center localized, edge localized; FIG. 1). These staining patterns and germination stage categories can be thus be mapped onto each other schematically (FIG. 13).

Figure 14C:
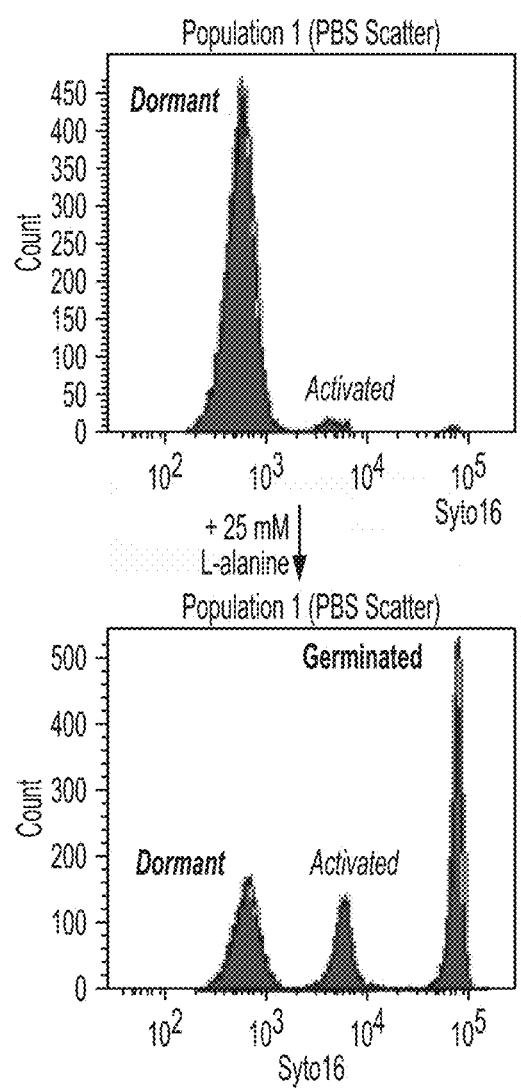
Figure 14D:
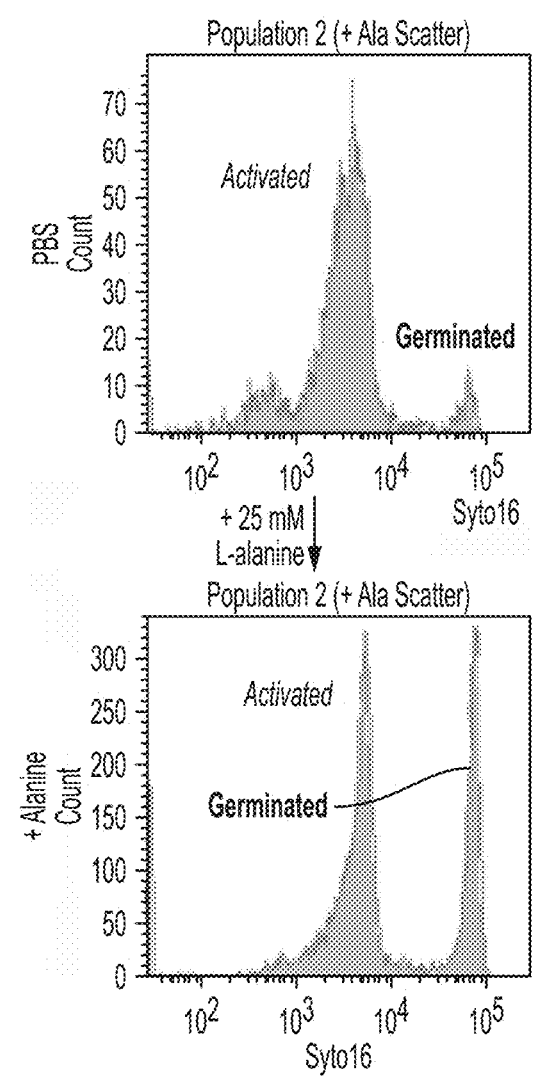
Figure 15:
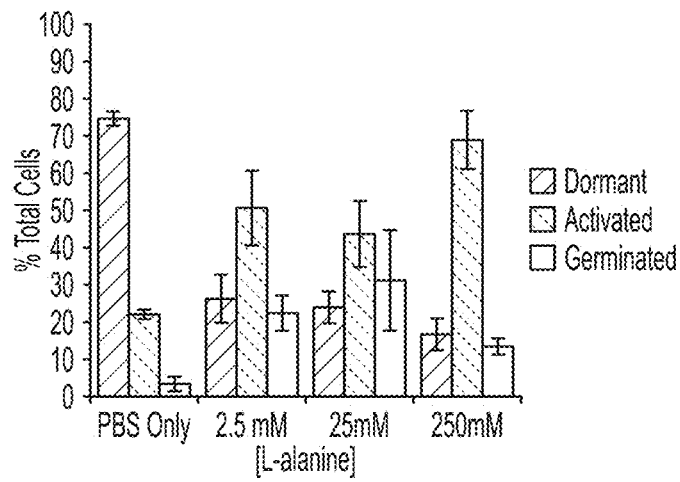
FIG. 15 shows a summary of flow cytometry signatures of *B. megaterium* SR7 spores incubated in PBS or L-alanine-amended (2.5, 25, 250 mM) media. Summed distribution of Population 1 and Population 2 counts within each of the three Syto16/PI fluorescence gates are shown in top panel. Values presented in plot, as well as spore stock distributions, are shown in the bottom panel.

Population 1 (PBS) and 2 (PBS+L-alanine) display marked differences in terms of fluorescence magnitudes and distributions (FIG. 14). A wide majority of spores incubated in PBS are gated as dormant cells (74.3%), with 22.0% and 3.7% gated as activated and germinated, respectively (FIGS. 14 and 15). When L-alanine is amended to PBS cultures, fluorescence distributions shift towards activated (44-69%) and germinated (1.38-31.8%) fluorescence signatures (FIGS. 14 and 15). These results reinforce the implication that L-alanine acts to induce physiological changes involved in the progression from dormant endospore to germinated cell.

*B. megaterium* SR7 Growth and Activity Under Supercritical $CO_2$

Results generated under aerobic and 1 atm $CO_2$ conditions investigating the physiology, growth dynamics and germination induction of *B. megaterium* SR7 were integrated in an effort to generate robust growth and production of natural products under $scCO_2$. Chemical induction experiments in P-LB medium spore-loaded $scCO_2$ incubations (Table 14) revealed that L-alanine confers a statistically significant improvement in germination rates and growth outcomes relative to inducer-free cultures (FIG. 16), while L-leucine reduced growth frequency under $scCO_2$ conditions relative to controls. Growth was defined as at least one order of magnitude increase in biomass according to epifluorescence cell counts:

1) high growth: ≥40-fold increase in direct cell counts relative to $t_0$ cell density
2) low growth: >10-fold increase in direct cell counts relative to $t_0$ cell density
3) germinated: <10-fold increase, mixture of vegetative cells and spores
4) dormant: <10-fold increase, only spore morphologies observed

TABLE 14

Growth outcomes for unamended and induced $scCO_2$ cultures

| Incubation | Duration | Media | Growth |
|---|---|---|---|
| A | 18 days | P-LB | 3/7 |
|   |   | P-LBA | 5/7 |
|   |   | P-LBA (+Heat) | 3/6 |
|   |   | P-LBL | 1/7 |
|   |   | P-LBAL | 2/7 |
|   |   | Neg Ctrl | 0/4 |
| B | 20 days | P-LB | 1/7 |
|   |   | P-LBA | 5/7 |
|   |   | P-LBL | 0/6 |
|   |   | P-LBAL | 2/6 |
|   |   | Neg Ctrl | 0/4 |
| C | 18 days | P-LB | 1/6 |
|   |   | P-LBA | 3/5 |
|   |   | Neg Ctrl | 0/4 |

Overall, growth was observed in 63% of all cultures amended with L-alanine, while only 36% of unamended reactors showed growth (Table 14). Median fold increase in cell concentration for P-LBA cultures was 37.5 and for unamended phosphate-buffered LB (P-LB; Table 1) was 22.8. Using growth frequency and fold change as inputs for non-parametric modeling of $scCO_2$ growth outcomes established that L-alanine conferred a statistically significant improvement on growth (p=0.0036) relative to P-LB cultures by a Wilcoxon/Kruskal-Wallis Test. L-leucine (P-LBL media) only generated growth in 7.7% of reactors, while the combined treatment of L-alanine and L-leucine (P-LBAL) resulted in 31% growth frequency. Diminished growth in L-leucine reactors suggests a neutral to inhibitory effect on B. megaterium SR7 $scCO_2$ germination and growth, which is unexpected based on 1 atm $CO_2$ results (Table 14). As the L-alanine+heat treatment reactors (50%) also did not grow as well as non-heated L-alanine reactors, L-leucine and heat treatment were discarded as potential growth enhancing components of the microbial bioproduction system.

Figure 16:
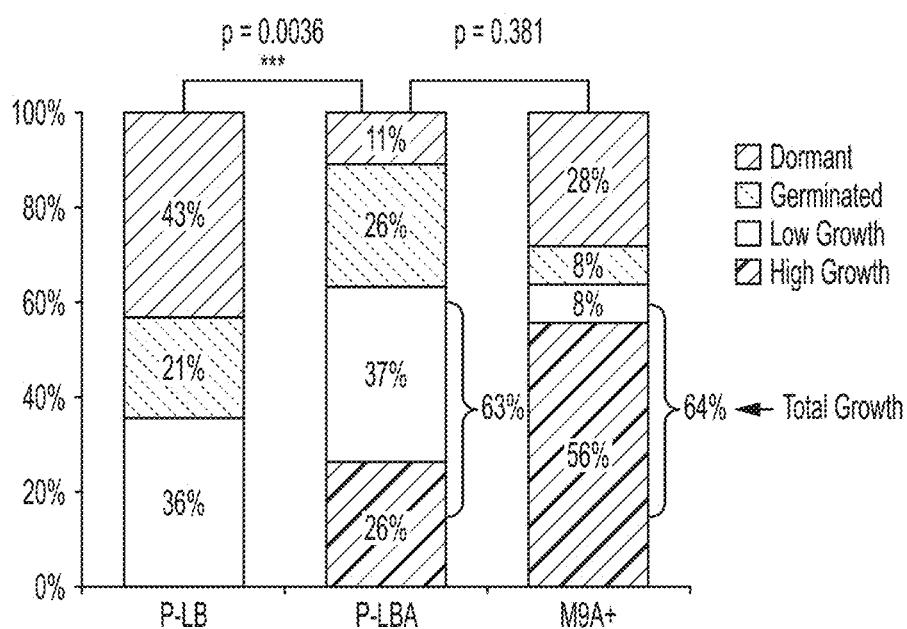
FIG. 16 shows *B. megaterium* SR7 germination and growth frequencies under $scCO_2$ in respective media based on cumulative results pooled from multiple individual experiments, as summarized in Table 14. In each column, the frequencies are presented, from top to bottom, dormant, germinated, low growth, and high growth.

After verifying the positive growth effect of L-alanine on spore-loaded P-LBA $scCO_2$ cultures, two rounds of 18-20 day $scCO_2$ incubations of SR7 spores in M9A+ displayed growth in 11/18 reactors and 5/7 reactors, respectively. The total frequency of growth in M9A+ (64%) is thus comparable to P-LBA (63%), though M9A+ appears to increase the frequency of high level (>40 fold) growth (56% in M9A+ vs. 26% in P-LBA; FIG. 16). Despite similar overall frequencies, median biomass accumulation was improved for cultures grown in M9A+ (64.3 fold increase) relative to P-LBA (37.5 fold).

Figure 17:
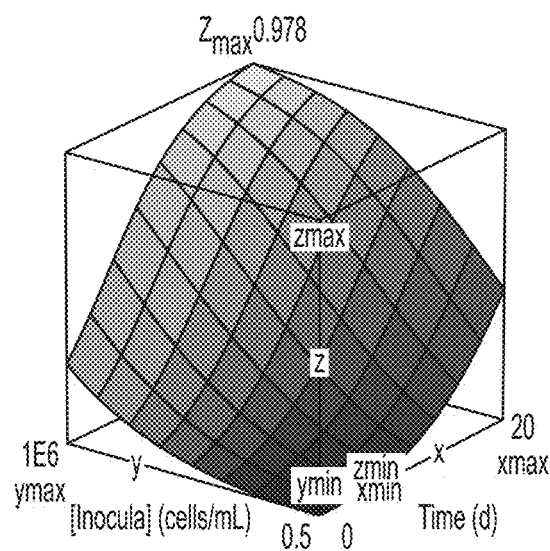
FIG. 17 shows nominal logistic regression of SR7 $scCO_2$ growth frequency (Z axis) as a function of inocula spore density (p=0.0057; Y axis) and incubation time (p=0.003; X axis).

As statistical tests did not establish significance (p=0.381) in differential growth outcomes for P-LB and M9+, subsequent system development proceeded with semi-defined M9A+ minimal media, which simplifies pathway engineering architecture and metabolic flux analysis due to growth on a single carbon source. In order to more fully understand the relationship between starting B. megaterium SR7 spore concentration and likelihood of growth in M9A+ media, a logistic regression model for growth frequency was generated in part using data from an 18 day $scCO_2$ time course experiment (sampled at 6, 12, and 18 days) with starting spore concentrations varied over six orders of magnitude. The results of the incubation are summarized in Table 15, using a 10-fold increase in filter cell counts as the threshold for growth. After merging the time course growth data (Table 15) with previously generated results from M9A+ incubated spores (Table 14) a total of 91 experimental samples and 24 negative controls subjected to logistic regression analysis demonstrated that both loaded spore density (p=0.0057) and incubation time (p=0.003) have statistically significant impacts on growth frequency, while the interaction of their effects was not significant (p=0.89). The overall regression model generated the following equation (plotted in FIG. 17) to describe growth frequency (Z) as a function of incubation time (X) and starting inocula concentration (Y).

$$Z = \frac{1}{1 + e^{4.7849 - .228 * X - (3.8207 * 10^{-6}) * Y}}$$

B. megaterium SR7 Fermentation Products Under $scCO_2$

Figure 18:
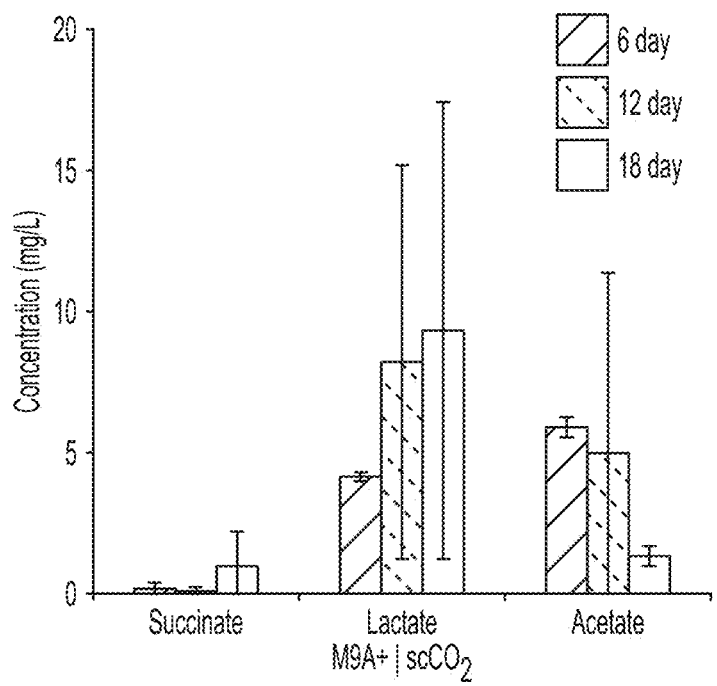
FIG. 18 shows concentrations of fermentative products generated in M9A+ medium by SR7 cultures under $scCO_2$ showing growth, as detected by HPLC. The columns are, from left to right, samples obtained from 6 days, 12 days, and 18 days. No fermentation products were detected in cell-free control incubations or $scCO_2$ cultures not demonstrating growth.

Cultures from 6, 12, and 18-day SR7 time course incubations in M9A+ media demonstrating growth (>10-fold increase in cell counts) under $scCO_2$ were analyzed for natural fermentation products by HPLC. Cultures generated several detectable metabolites, including for succinate (up to 2.4 mg/l), lactate (up to 17.8 mg/l), and acetate (up to 9.5 mg/l) (FIGS. 18A and 18B). All metabolites were also detected in culture under 1 atm $CO_2$ conditions grown in similar M9+ media (FIG. 10), suggesting shared features of active fermentative pathways under both conditions. Normalization of product concentrations by total cell counts enables calculation of metabolite productivities on per cell basis. Maximum per cell productivity values (mg product cell-1) are $1.1 \times 10^{-10}$, $5.0 \times 10^{-10}$, and $1.3 \times 10^{-9}$ for succinate, lactate and acetate, respectively. These productivities are comparable to results observed under 1 atm $CO_2$ (assuming OD600=1.0 corresponds to $10^8$ cells/ml, based on filter counts), which displayed maximum productivities (mg product cell$^{-1}$) in M9+ media of $5.5 \times 10^{-10}$, $3.4 \times 10^{-10}$, and $5.8 \times 10^{-10}$ for succinate, lactate, and acetate, respectively. Therefore, a relationship within roughly an order of magnitude appears to exist between concentration of per cell metabolite production and total cell numbers per culture.

The work described herein allowed for the identification and isolation a $scCO_2$-compatible strain, B. megaterium SR7. This strain was used to develop optimal process engineering and culturing modifications in order demonstrate the capacity for enhanced growth and natural product generation under $scCO_2$.

Example 2: Metabolic Engineering of Bacillus megaterium SR7 for Heterologous Gene Expression and Advanced Biofuel Synthesis and Recovery Under Biphasic Aqueous-Supercritical $CO_2$ Conditions The $scCO_2$ harvesting systems described herein were evaluated for production of biofuels, which due to the semi-hydrophobic chemistry of alcohols like isobutanol and butanol, readily causes compound partitioning from the aqueous phase into $scCO_2$ (e.g., Kow>4; Timko et al., 2004). Although short-to-medium chain alcohols (e.g., isobutanol, isopentanol) were produced in the methods described herein, $scCO_2$ culturing methods holds may be useful for extraction of a broad range of high-value bioproducts.

Figure 19:
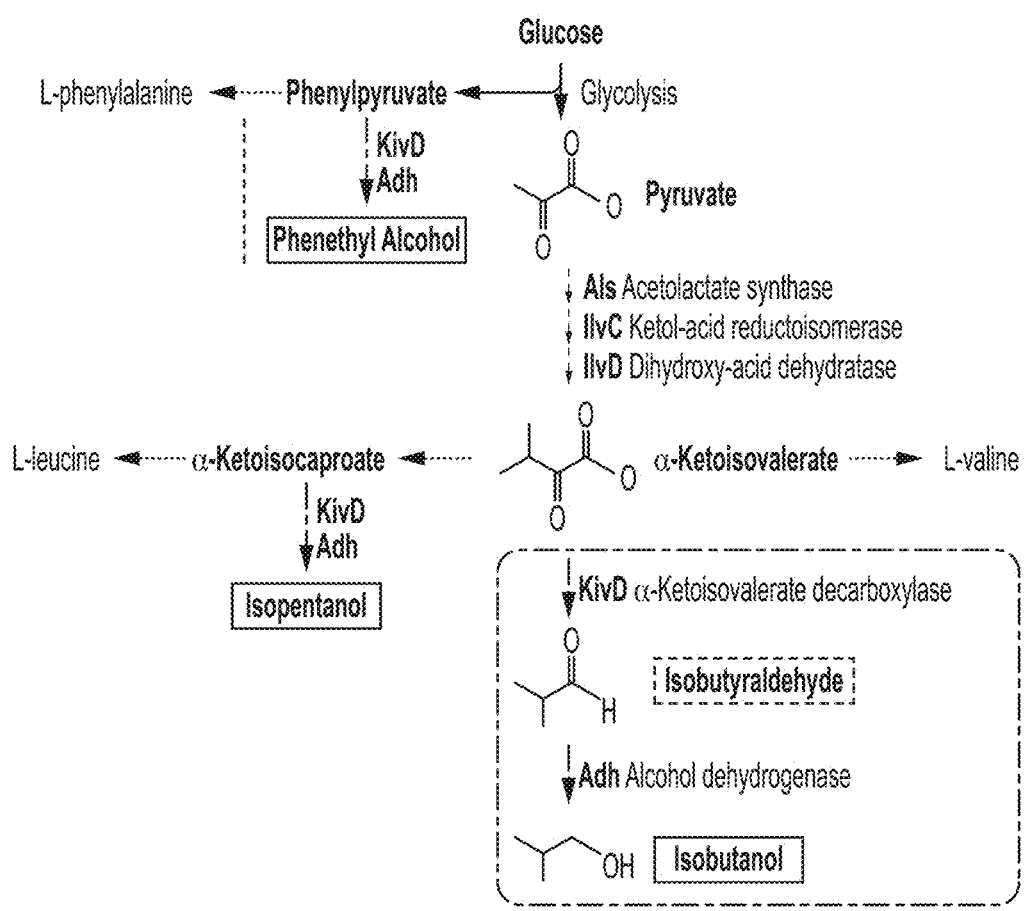
FIG. 19 shows an isobutanol biosynthesis pathway from α-KIV encompassed by the dashed line.

Isobutanol production requires modification of the amino acid valine biosynthesis pathway by directing flux of the intermediate α-ketoisovalerate (α-KIV) away from L-valine production and instead towards isobutyraldehyde and finally isobutanol (Atsumi et al., 2008; FIG. 19). α-KIV itself is generated from the condensation of two pyruvates (via pyruvate kinase, Pyk), which is decarboxylated (via acetolactate synthase, IlvIH) to form 2-acetolactate, then reduced (via acetohydroxy acid isomeroreductase, IlvC) and dehydrated (via dihydroxy acid dehyratase, IlvD) to α-KIV. Insertion of exogenous pathway genes for keto-acid decarboxylase (kivD) and alcohol dehydrogenase (adh) then facilitates isobutanol production from α-KIV.

The results described herein demonstrate a two-phase harvesting method for stripping of microbially produced chemicals using in situ $scCO_2$ extraction. These methods involve the development of a genetic system for expression of single and multi-gene pathways under $scCO_2$ and the first demonstration of in situ bioproduct recovery by partitioning into $scCO_2$, thereby establishing a new branch of microbial bioproduction by enabling access of an engineered bacterial strain to the unique properties of sustainable solvent supercritical carbon dioxide.

Methods

Strain, Media and Culture Conditions

As described herein, environmental strain *Bacillus megaterium* SR7 was isolated through enrichment culture and serial passaging of fluids sourced from the deep subsurface McElmo Dome supercritical $CO_2$ formation (Example 1). Previous *B. megaterium* SR7 development under 1 atm $CO_2$ included the formulation of semi-defined minimal medium M9+, which consists of M9 base medium amended with 0.4% D-glucose, 50 mM yeast extract, 0.1× trace metals solution (Boone et al., 1989). The addition of 100 mM L-alanine to M9+(resulting in medium "M9A+") was previously shown to increase rates of SR7 spore germination and growth rate under $scCO_2$ conditions. Therefore, all culturing experiments conducted under 1 atm $CO_2$ occur in M9+ medium, and under $scCO_2$ in M9A+ medium. All cultures were incubated at 37° C. and 250 rpm based on previous results showing enhanced growth rates and population longevity under these conditions. All 1 atm $CO_2$ and $scCO_2$ experiments were prepared within an anaerobic chamber (Coy Products) containing an atmosphere of 95% $CO_2$ and 5% $H_2$. Experiments conducted under 1 atm $CO_2$ used 10 ml of $CO_2$-degassed culture media in 100 ml serum vials with clamped rubber stoppers. Incubations under $scCO_2$ used ¾ inch 316 stainless steel tubing fitted with quarter turn plug valves (Swagelok (Solon, Ohio) or Hylok (Houston, Tex.)) for 10 ml total capacity. As described in Example 1, reactors were filled to ½ capacity (5 ml) with inocula and degassed media, after which the headspace was pressurized with extraction grade $CO_2$ gas at a rate of 2-3 atm $min^{-1}$ until reaching a final pressure of 100 atm. After pressurization, reactors were incubated in a 37° C. warm room and mixed at 250 rpm until unloading.

Development for SR7 Genetic Manipulation and Expression Vector Construction

Figure 20:
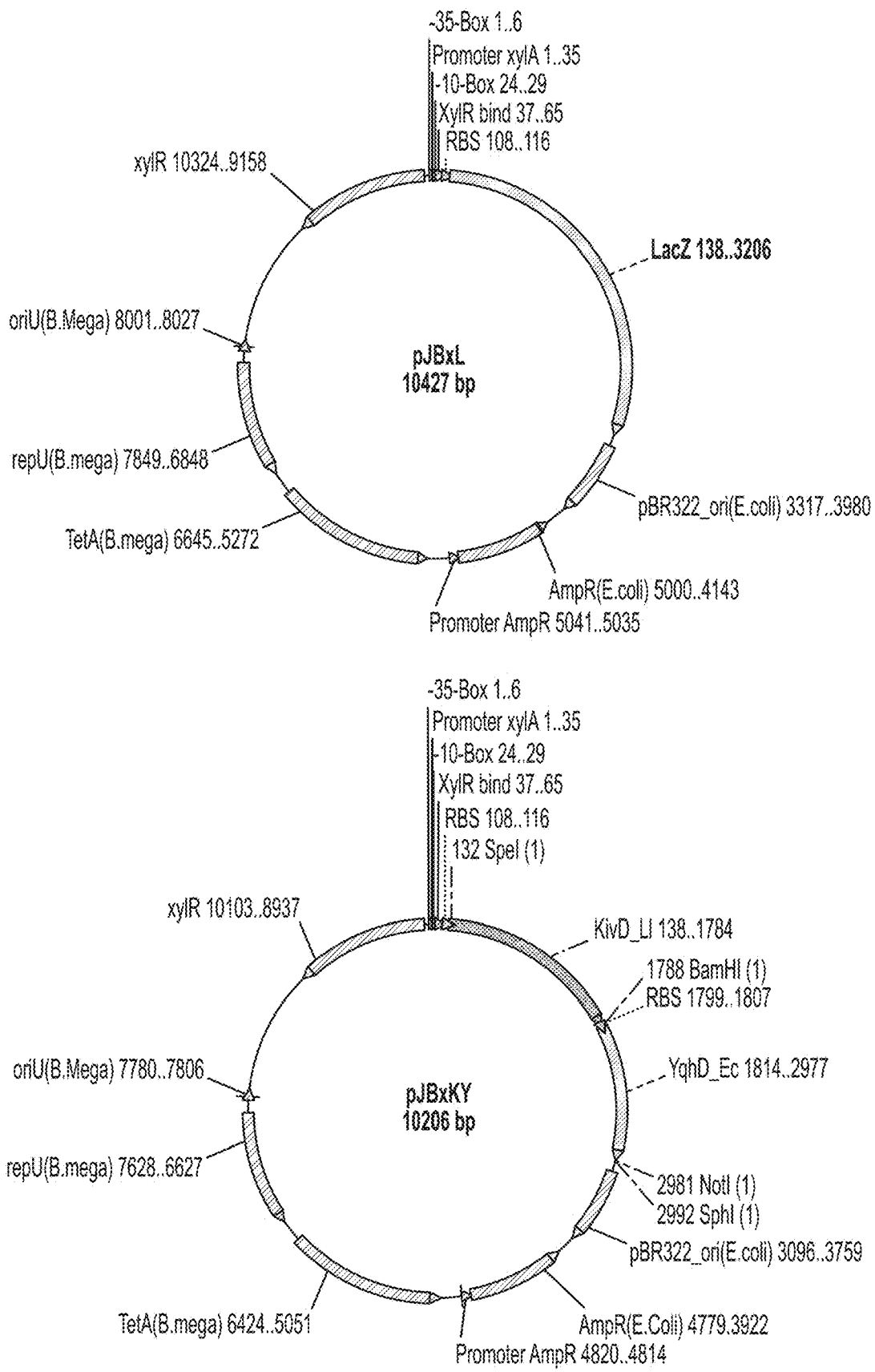
FIG. 20 shows vector maps for pJBxL (left) and pJBxKY (right) using scaffold pRBBm34.

All primers used in plasmid construction, final vector constructs, transformed strains and associated references are presented in Tables 15A and 15B. The lacZ gene was PCR amplified from plasmid pKVS45 LacZ_LVA with primers LacZ_F and LacZ_R. Shuttle vector pRBBm34 (Amp® (*E. coli*), Tet® (*B. megaterium*); pBR322 Ori (*E. coli*), RepU (*B. megaterium*)) was used as a scaffold for pathway genes. PCR products and pRBBm34 were digested with SpeI and SphI prior to ligation to create the pJBxL plasmid (FIG. 20, left panel). The xylose repressor and promoter of pRBBm34 were replaced with a hyper-spank promoter ($P_{Hyper-spank}$) and lacI using circular polymerase extension cloning (CPEC). The pRBBm34 plasmid was PCR linearized with two sets of primers to remove xylR and $P_{Xyl}$: pRBBm34_F/Bla_R and Bla_F/pMM1520R. $P_{Hyper-spank}$ and lacI were PCR amplified from pDR111 using pMM1520-$P_{Hysp}$_F and LacI-pRBBm34_R. Standard CPEC cloning was used to assemble the three PCR products into the $P_{Hyper-spank}$ plasmid. The lacZ gene with a ribosome-binding site was PCR amplified from the plasmid pKVS45 LacZ_LVA using: RBS-LacZ_F and LacZ_R. PCR products and the $P_{Hyper-spank}$ plasmid were digested with SalI and SphI prior to ligation to create the pJBhL plasmid.

TABLE 15A

Primers used for vector construction

| Name | Sequence (5' > 3') | Target | Reference |
| --- | --- | --- | --- |
| LacZ_F | GTCCAAACTAGTACCATGATTACGG ATTCACTGGC (SEQ ID NO: 3) | pKVS45 LacZ_LVA | Solomon et al., 2012 |
| LacZ_R | CCGCCGGCATGCTCATTATTTTGA CACCAGACCAACTGG (SEQ ID NO: 4) | | |
| pRBBm34_F | CGGCGGCACCTCGCTAAC (SEQ ID NO: 5) | pRBBm34 | Biedendieck et al., 2007 |
| Bla_R | GGTGCCTCACTGATTAAGCATTGG (SEQ ID NO: 6) | | |
| Bla_F | CCAATGCTTAATCAGTGAGGCACC (SEQ ID NO: 7) | pMM1520 | Malten et al., 2005 |
| pMM1520_R | AGATCCACAGGACGGGTGTG (SEQ ID NO: 8) | pDRIII | Guerout-Fleury et al., 1996 |
| pMM1520_$P_{Hysp}$_F | CACACCCGTCCTGTGGATCTGACTC TCTAGCTTGAGGCATC (SEQ ID NO: 9) | | |

TABLE 15A-continued

Primers used for vector construction

| Name | Sequence (5' > 3') | Target | Reference |
|---|---|---|---|
| LacI_pRBBM34_R | GTTAGCGAGGTGCCGCCGGGATCCT AACTCACATTAATTGCG (SEQ ID NO: 10) | pKVS45 LacZ_LVA | Solomon et al., 2012 |
| RBS-LacZ_F | AGCTTAGTCGACAGGGGGAAATGTA CAATGACCATGATTACGGATTCAC GGC (SEQ ID NO: 11) | | |
| KivD_F | GTCCAAACTAGTATGTATACAGTAG GAGATTACCTATTAGACCG (SEQ ID NO: 12) | pCOLA KivD, Fjoh_2967 | Sheppard et al., 2014 |
| KivD_R | GAGGAGCATGCGAGCTCGGATCCT CATTATGATTTATITTGITCAGCAA ATAGTITACCC (SEQ ID NO: 13) | | |
| RBS-ADII6_F | GAGGAGGGATCCTCGACAGGGGGAA ATGTACAATGAGCTACCCGGAAAAG TTCG (SEQ ID NO: 14) | pACYC (car, stp) | |
| ADH6_R | CCGCCGGCATGCAATGCGGCCGCTC ATTAGTCGCTGAATTCTTTATCGTA ACCAACC (SEQ ID NO: 15) | | |
| RBS-YqhD_F | TAATGAGGATCCTCGACAGGGGGAA ATGTACAAATGAACAACTTTAATCT GCACACCC (SEQ ID NO: 16) | E. coli MG1655 gDNA | Common lab strain |
| YqhD_R | GCATGCAATGCGGCCGCTCATTAG CGGGCGGCTTCGTATATAC (SEQ ID NO: 17) | | |

TABLE 15B

Vector constructs and strains used in the work described herein

| Strain | Plasmid | Description/Genotype | Reference |
|---|---|---|---|
| B. megaterium SR7 | Endogenous only | Wild-type isolate from scCO$_2$ subsurface formation | Thesis Ch. 3 |
| SR7JR1 | pJR1 | CmR; mob, oriT, rep (E. coli), pUCTV2 ori$^{ts}$ (Bacillus), sacB (B. subtilis) | Richhardt et al., 2010 |
| SR7x | *pJBx | P$_{Xyl}$-empty construct | This study |
| SR7xL | *pJBxL | P$_{Xyl}$ lacZ; Tet$^R$ | study |
| SR7h | *pJBh | P$_{Hyper-speak}$-empty construct; Tet$^R$ | This study |
| SR7hL | *pJBhL | P$_{Hyper-speak}$ lacZ; Tet$^R$ | This study |
| SR7xK | *pJBxK | P$_{Xyl}$ kivD$_{L1}$; Tet$^R$ | This study |
| SR7xKA6 | *pJBxKA6 | P$_{Xyl}$ kivD$_{L1}$, adh6$_{Sc}$; Tet$^R$ | This study |
| SR7xKY | *pJBxKY | P$_{Xyl}$ kivD$_{L1}$, yqhD$_{Ec}$; Tet$^R$ | This study |
| SR7xKAB | *pJBxKAB | P$_{Xyl}$ kivD$_{L1}$, adhA$_{Bm}$; Tet$^R$ | This study |
| SR7xKAL | *pJBxKAL | P$_{Xyl}$ kivD$_{L1}$, adhA$_{Li}$; Tet$^R$ | This study |
| SR7xKAP | *pJBxKAP | P$_{Xyl}$ kivD$_{L1}$, adhA$_{Ec}$; Tet$^R$ | This study |
| SR7xGFP | *pJBxGFP | P$_{Xyl}$ sfGFP; Tet$^R$ | This study |
| SR7hGFP | *pJBhGFP | P$_{Hyper-speak}$ sfGFP; Tet$^R$ | This study |

*pRBBm34 derivative (Biedendieck et al., 2007)

For solventogenesis strain engineering, kivDL1 sourced from *Lactococcus lactis* and adh6Sc from *Saccharomyces cerevisiae* were placed downstream of xylose-inducible promoter PXyl on pRBBm34. Vector construction began by PCR amplifying kivDL1 from pCOLA KivD, Fjoh_2967 using primers KivD_F and KivD_R. PCR products and the pRBBm34 plasmid were digested with SpeI and SphI prior to ligation to create the pJBxK plasmid. Adh6Sc from *S. cerevisiae* was PCR amplified from pACYC (car,sfp; adh6) with the same ribosome binding site as was used for kivDL1 using primers RBS-ADH6_F and ADH6_R. Adh6Sc was added between the BamHI and SphI restriction sites in PXyl KivDL1 to create pJBxKA6. YqhDEc from *E. coli* was PCR amplified from *E. coli* MG1655 genomic DNA with the same ribosome binding site as was used for kivDL1 using primers RBS-YqhD_F and YqhD_R. YqhDEc was added between the BamHI and SphI restriction sites in PXyl KivDL1 to create pJBxKY (FIG. 20, right panel). All constructs were verified by DNA sequencing.

Transformation Methods

Initial attempts to genetically transform strain SR7 with shuttle vector pRBBm34 (Addgene; Cambridge, Mass.) used an established *Bacillus* electroporation protocol (Zhang et al. (2011; Analytical Biochemistry). Modifications to the method included the addition of cell wall weakeners (3.9% glycine, 80 mM DL-threonine) one hour prior to electroporation, and testing a wide range of plasmid concentrations (10-200 ng/µl) and cell densities (OD600 0.6-1.2). Conjugation-based transformation was attempted with SR7 using mating strain *E. coli* S-17 and plasmid pJR1 (provided courtesy of the Meinhardt Lab, University of Muenster, Germany; Table 1B), following the protocol of Richhardt et al. (2010). To optimize the protocol, a range of donor to recipient strain volumes were tested (e.g., 10:1 to 1:1000) after reaching protocol-prescribed OD600 values. Post-transformation counter-selection included pasteurization and the sacB suicide system. The final transformation method attempted was protoplast fusion based on von Tersch and Robbins (1990) and Biedendieck et al. (2011) using shuttle vector pRBBm34. The cell wall removal step was optimized to increase viable protoplasts by modifying lysozyme concentrations and transformed protoplast incubation times. Counter-selection occurred by plating protoplasts on a soft agar overlay above LB agar containing 5 μg/ml tetracycline.

Plasmid Maintenance

Several assays were utilized to verify exogenous plasmid stability in SR7 during growth under 1 atm $CO_2$. To assay for maintenance of pRBBM34 in SR7 under 1 atm $CO_2$, singleton incubations of SR7 empty vector control strain (SR7x), which constitutively expresses tetracycline resistance, were inoculated at a concentration of $10^5$ spores/ml and passaged three times in LB for 24 hours with and without supplementation of 0.5 μg/ml tetracycline. After each passage, cultures were plated on LB agar with or without 0.5 μg/ml tetracycline to determine if cultures grown without antibiotics maintained the transformed vector over multiple growth cycles in the absence of a selective pressure. SR7 wild-type and SR7x strains were also assayed to determine minimum required tetracycline concentration to select for transformed strains containing the vector. Cultures inoculated with $10^5$ spores/ml were incubated in LB amended with a range of tetracycline concentrations under both aerobic (Tet 0.05-10.0 μg/ml) and 1 atm $CO_2$ conditions (Tet 0.1-10.0 μg/ml) and scored for growth by $OD_{600}$ relative to cultures that were not amended with Tet.

Heterologous Single Gene Expression Under 1 Atm $CO_2$ and $scCO_2$

B. megaterium SR7 strains SR7xL and SR7hL (bearing genetic constructs pJBxL and pJBhL, respectively) and empty vector control strains SR7x and SR7h were assayed for protein expression in B. megaterium SR7 under 1 atm $CO_2$ and $scCO_2$ conditions. 1 atm $CO_2$ cultures grown overnight were diluted in fresh media to $OD_{600}$ 0.01, cultured for 2 hours, then amended with 0.4% D-xylose ($P_{Xyl}$: SR7x, SR7xL) or 5 mM ITPG ($P_{Hyper-spank}$; SR7h, SR7hL) to induce expression. After 24 hours, 1 ml of culture volume was spun down for 5 min×21,000 g and the remaining pellet was stored at −20° C. until analysis.

Supercritical $CO_2$ cultures were loaded with $3\times10^5$ spores/ml (as described in Example 1) of strain SR7xL. A subset of reactors was amended with 0.5% xylose inducer. Reactor cultures were incubated for 21 days then depressurized and prepared for fluorescence microscopy as previously described. 2 ml of culture volume was spun down for 5 min×21,000 g, after which the supernatant and pellet were separately stored at −20° C. until analysis. Supernatant was prepared for GC-MS analysis by methods described below and for HPLC analysis by methods described in Example 1.

Pellets from 1 atm $CO_2$ and $scCO_2$ cultures were lysed by addition of 100 μl of Bacterial Protein Extraction Reagent (B-PER; Thermo Scientific; Waltham, Mass.) and vortexed for 30 minutes. After lysed pellets were centrifuged for 20 min×18,500 g at 4° C., supernatants were prepared for total protein analysis using the Pierce™ BCA Protein Assay Kit (Thermo Scientific; Waltham, Mass.) according to manufacturer's instructions. Colorimetric signatures proportional to total sample protein were measured by $OD_{562}$, including for cell-free B-PER negative controls. Total protein standard curves were generated using 0.05-1.0 mg/ml of bovine serum albumin (BSA) according to the same protocol. Samples and B-PER negative control were prepared for LacZ activity assays by adding 70 μl of lysed culture supernatant to 730 μl of assay buffer (0.1 M sodium phosphate buffer, 10 mM KCl, 1 mM MgSO4) and 200 μl of β-galactosidase substrate (4 mg/ml o-nitrophenyl-β-D-galactoside, ONPG). LacZ activity was quantified as the rate of $OD_{420}$ absorbance per minute, as the product of ONPG cleavage by B-galactosidase absorbs at 420 nm. Absorbance rate was normalized by total protein per culture using BSA standard curves. Protein-normalized rates were converted to specific activity using the assay extinction coefficient and volume to generate units of $\mu mol\ min^{-1}\ mg^{-1}$.

Heterologous Biofuel Production Under 1 Atm $CO_2$

Vegetative cultures of SR7x and SR7xKA6 were prepared by growing $10^5$ spores/ml of each strain in $CO_2$-degassed LB $tet_{0.5}$ for overnight growth. Stationary phase cultures were then diluted in 10 ml of fresh LB+$tet_{0.5}$ to $OD_{600}$ 0.01. After 2 hours, passaged cultures were amended with 5 mM α-KIV substrate and 0.4% D-xylose to induce gene expression. Passaged cultures were grown for 24 hours post-induction, with sub-sampling at 4 and 24 hours by aseptic needle extraction. After 1 ml samples were centrifuged for 5 minutes×21,000 g, 500 μl supernatant was pipetted into separate tubes with 500 μl of ethyl acetate solvent (≥99.9% pure GC-grade, Sigma Aldrich) and vortexed for 5 minutes. The ethyl acetate fraction was pipetted into analysis vials (Agilent) and loaded on the Agilent Technologies 7890B GC system (using Agilent J&W VF-WAXms GC Column) (Agilent Technologies; Santa Clara, Calif.) and 5977A MSD for gas chromatography-mass spectrometry (GC-MS) analysis using MassHunter Qualitative Analysis (Agilent; Santa Clara, Calif.) software to measure compound concentrations. Peaks in the resulting total ion current (TIC) chromatogram were input into the NIST MS Search 2.2 database for compound prediction. Prior to running incubated samples, standard curves were generated using a range of concentrations (0.2-5.0 g/l) of expected products (isobutyraldehyde, isobutanol, isopentanol, phenethyl alcohol, acetate) using flame ionization detector (FID) spectra. Integrated total ion current (TIC) chromatogram peaks for differentially produced compounds were measured and converted to g/l concentrations according to standard curve conversion factors.

Alcohol Dehydrogenase Screening

To assay for differential alcohol dehydrogenase activity under aerobic and 1 atm $CO_2$ conditions, pRBBm34 vectors were constructed using previously described methods with xylose-inducible promoter $P_{Xyl}$ upstream of $kivD_{L1}$ and one of five alcohol dehydrogenase variants: adh6/pJBxA6 (S. cerevisiae), $adhA_{Bm}$/pJBxKAB (B. megaterium SR7), $adhA_{LL}$/pJBxKAL (L. lactis), $adhP_{Ec}$/pJBxKAP (E. coli), and yqhD/pJBxKY (E. coli) (constructs and strains summarized in Tables 15A and 15B).

For aerobic screens, freezer stocks of each strain were streaked onto LB agar plates supplemented with tetracycline (5 μg/ml) and grown at 37° C. overnight. For each alcohol dehydrogenase, three colonies were added separately to 5 ml of LB with tetracycline and grown at 37° C. overnight. Each sample was sub-cultured to an $OD_{600}$ of 0.05 in 3 ml of LB with tetracycline in a 50 ml screw-capped glass tube. Cultures were grown at 37° C. and 250 RPM until an $OD_{600}$ of ~1.0 was reached, at which point 5 mM α-ketoisovalerate (α-KIV) precursor was added and protein production induced by supplementing with 0.5% D-xylose. Cultures were grown at 37° C. and 250 RPM. Time points were taken at 4 hours, 24 hours and 48 hours by removing 1 ml of culture volume. Samples were centrifuged at 20,000×g for 5 minutes and the supernatant removed. Alcohols were extracted from the supernatant using a 1:1 ratio of supernatant to ethyl acetate and vortexed at maximum speed for 5 minutes. The ethyl acetate fraction was recovered by centrifugation at 20,000×g for 5 minutes and removal of the upper solvent fraction. Sample analysis by GC-FID and concentrations of produced alcohols by standard curve calculations used previously described methods.

1 atm $CO_2$ cultures inoculated with 10 spores/ml of each strain were grown overnight and passaged by syringe needle into fresh $CO_2$-degassed LB+$tet_{0.5}$. Two hours after passaging, cultures were amended with 5 mM α-KIV substrate and 0.5% D-xylose for gene induction. Sampling of strain variant cultures took place at 24 and 48 hours by syringe needle. Samples were then prepared for GC-MS analysis and post-run data processing as previously described.

Full Isobutanol Pathway

Figure 26A:
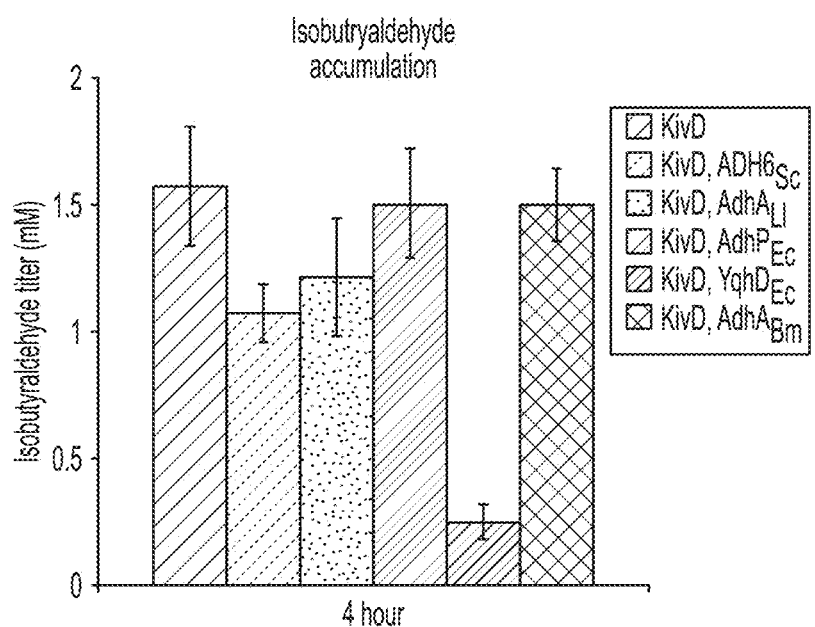
FIGS. 26A-26D show bioproduct concentrations generated under aerobic conditions.
Figure 26B:
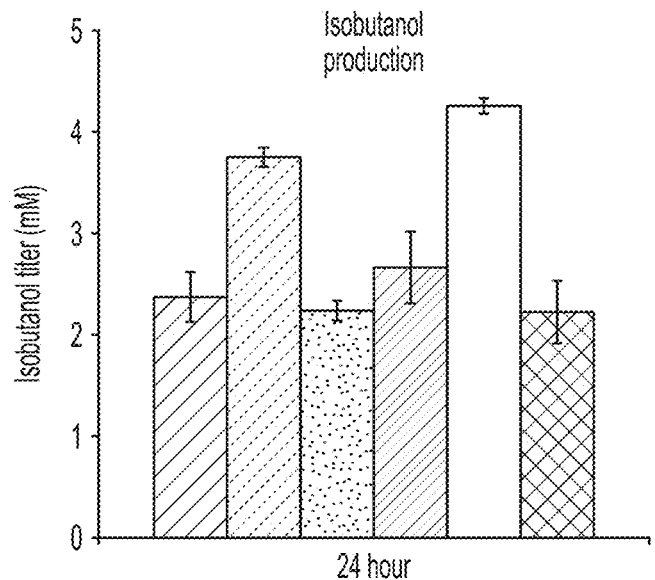
Figure 26C:
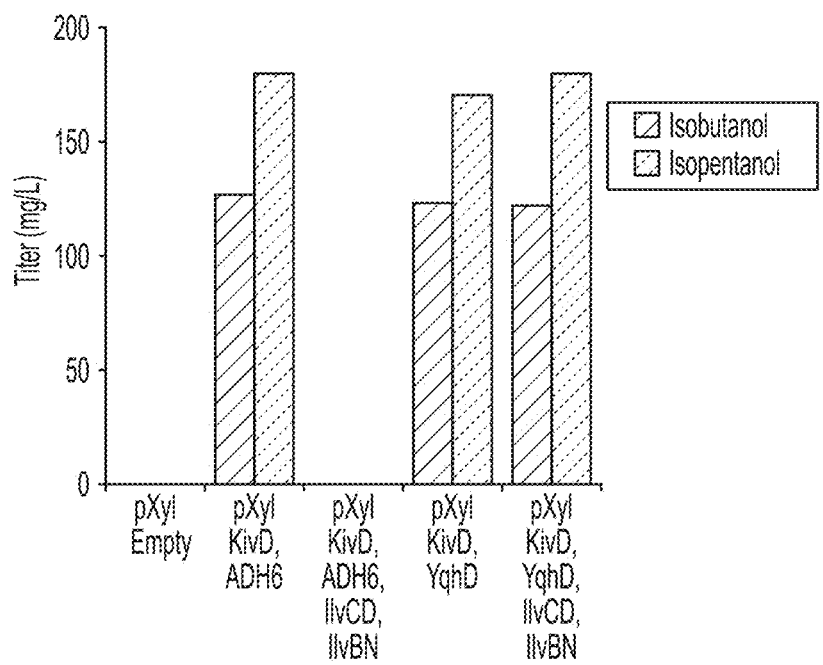

Although production of isobutanol through a two-step conversion of α-KIV using keto-isovalerate decarboxylase and various alcohol dehydrogenases has been demonstrated, α-KIV is an expensive substrate for isobutanol production. It may be desired to use an inexpensive, six-carbon substrate such as glucose for isobutanol production. Isobutanol production from glucose utilizes two endogenous cellular pathways, glycolysis to convert glucose to pyruvate and valine synthesis to convert pyruvate to α-KIV (FIG. 19). The ilvCD and ilvBN operons from *E. coli* were added to pJBxKA6 or pJBxKY vectors to generate the full 6 enzyme pathway for the conversion of pyruvate to isobutanol. After transforming the plasmids into SR7, the functionality of the pathway was assessed in the presence of glucose and xylose (as inducer and carbon source) for SR7 grown in M9+ media (FIG. 26C).

After initial biofuel screens, the pathway was regenerated such that each gene contained a ribosome-binding site that has previously shown high production in SR7. Instead of using the ilvBN operon from *E. coli*, the acetolactate synthase gene, alsS, was selected from *B. subtilis* to be paired with ilvC and ilvD from *E. coli*. The new plasmid contained five genes, including the alcohol dehydrogenase $ADH6_{Sc}$ that was previously tested in SR7. After confirming the transformation of the new plasmid in SR7, cells were grown in M9+ with 10-25 g/L glucose and 5 g/L xylose to determine if the full isobutanol pathway would lead to titers greater than 125 mg/L isobutanol that had been observed for the partial pathway.

Assay for Quantification of Isobutanol Production Under $scCO_2$

A headspace extraction setup was constructed to collect the $scCO_2$ phase with dissolved species from high-pressure growth reactors. 316 stainless steel lines and valves connected to the reactor pressurization manifold enabled direct depressurization of the $scCO_2$ headspace into ethyl acetate solvent for subsequent GC-MS analysis. To generate standard curves for isobutanol $scCO_2$ phase extraction, duplicate 10 ml incubation reactors were filled with cell-free LB medium amended with 5% isobutanol, 0.5% isobutanol and unamended LB. Reactors were pressurized with $CO_2$ to 100 atm, heated to 37° C. and shaken for 3 days to allow equilibration. Individual reactors were then slowly depressurized into 10 ml of chilled ethyl acetate at a rate of ~1 atm/min. This process was repeated a second time with several modifications, including submerging reactors in a heat bath at 55° C., increased depressurization rates (1.5-2 atm/min) and extraction into larger solvent volume (20 ml). A standard curve generated by GC-MS analysis of the initial extraction run enabled conversion of FID isobutanol peak areas to mg/l concentrations.

To determine whether SR7xKY produces isobutanol during growth under $scCO_2$ headspace, high-pressure reactors were loaded with $3 \times 10^5$ spores/ml of SR7xKY, control strain SR7xL, or cell-free media controls. A subset of reactors was amended with 0.5% xylose to induce gene expression. Reactors were pressurized to 100 atm $CO_2$, heated to 37° C. and incubated under $scCO_2$ for 21-22 days while shaking at 250 rpm. Reactors with identical inocula/media conditions (e.g., strain±xylose) or cell-free controls were simultaneously depressurized into chilled ethyl acetate at a rate of ~1 atm/min. Between each round of unloading, manifold lines and valves were flushed with ethyl acetate. Samples were prepared for GC-MS analysis as previously described. Quadruplicate technical replicates were run for all $scCO_2$ bulk phase-collected samples. Culture supernatant glucose concentrations were measured using the YSI 2900 with YSI 2814 glucose starter kit after spinning down 1 ml culture volume for 5 minutes×21.000 g. Depressurized cultures were prepared for epifluorescence microscopy by methods described in Example 1. Cultures were considered to have grown when demonstrating at least 10-fold increase in cell counts relative to loaded spore concentrations. The limit of detection was considered to be one half of a cell per 15 grids, which corresponds to $1.15 \times 10^3$ cells/ml.

Results

Development of a Genetic System for *B. megaterium* SR7

Three methods for transforming strain *B. megaterium* SR7 were tested: electroporation, conjugation and protoplast fusion. Genetic transformation of SR7 by electroporation using plasmid pRBBm34 was unsuccessful despite multiple attempts to modify protocol parameters based on published studies in other *B. megaterium* strains (Moro et al., 1995). Transformation by conjugation using the *E. coli* S-17 mating strain and vector pJR1 (Richhardt et al., 2010; Table 15B) gave mixed results with conferral of chloramphenicol resistance up to 10 μg/ml and positive PCR amplification of the plasmid-specific marker (sacB) in the resistant strains confirming transformation, albeit at a low frequency (e.g., 1 transformant per 107 SR7 cells). However, subsequent attempts to transform SR7 by the described conjugation protocol were not successful and thus prevented its further use in this specific study.

Protoplast fusion transformation, previously demonstrated in several *B. megaterium* strains (Bunk et al., 2010) proved successful at introducing all constructs used in this study via shuttle vector pRBBm34. Despite protocol modifications that increased viable protoplasts by fifty-fold, transformation efficiencies remained low (~1 transformed cell/107 viable protoplasts), frequently generating 1-3 successfully transformed colonies per μg of plasmid DNA. Protoplast transformation first enabled conferral of constitutive tetracycline resistance (10 μg/ml aerobic; 1.0 μg/ml under 1 atm $CO_2$). Maintenance of tetracycline resistance under 1 atm $CO_2$ was verified by nearly identical growth of cultures passaged three times in either LB or tetracycline-amended LB on unamended and tetracycline-amended plates. All subsequent genetic manipulation of strain SR7 was conducted using the modified protocol for protoplast fusion transformation.

Inducible Heterologous Enzyme Production Under 1 Atm $CO_2$ and $scCO_2$

Figure 21:
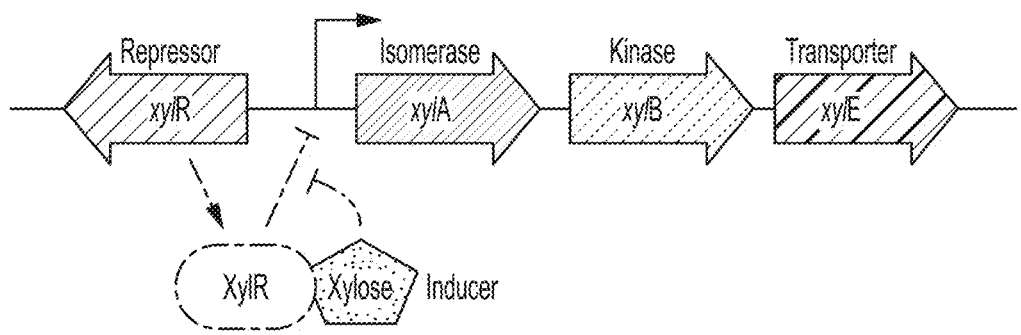
FIG. 21 shows a xylose promoter system endogenous to *B. megaterium*.

After demonstrating constitutive antibiotic expression, two promoters (PXyl and PHyper-spank) were investigated for inducible protein expression in SR7. The D-xylose-inducible PXyl promoter (FIG. 21) is endogenous to all sequenced *B. megaterium* strains, including SR7:

Rather than using the xylose promoter native to SR7, a previously optimized PXyl system (Biedendieck et al., 2007) was used to avoid uncharacterized endogenous promoter regulation specific to SR7. The IPTG-inducible hyper-spank promoter (PHyper-spank) had previously been transformed into and expressed in *B. subtilis* (van Ooij and Losick, 2003), but had never been utilized in *B. megaterium*.

Figure 22:
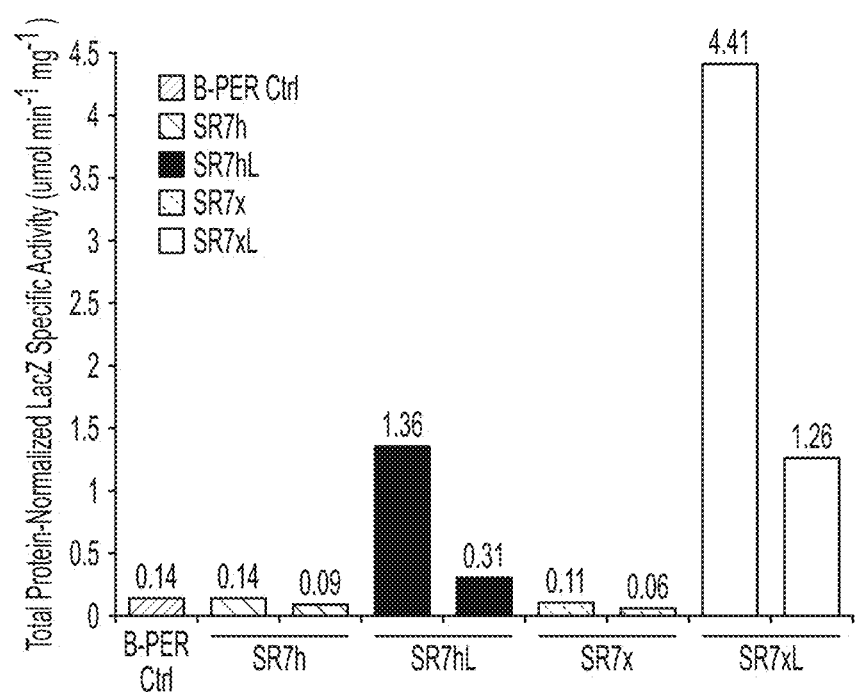
FIG. 22 shows LacZ specific activity of duplicate cultures using IPTG and xylose-inducible promoters under 1 atm $CO_2$, with B-PER as the negative control.

Plasmids pJBxGFP and pJBhGFP, where reporter super-folder GFP was placed under the control of the PXyl and PHyper-spank promoters, respectively, demonstrated induced expression in SR7 at nearly equal strengths under aerobic conditions assayed by GFP fluorescence intensity (data not shown). Low-level fluorescence in uninduced cultures appeared to show minor leakiness by PXyl. However, since fluorescent protein reporters including GFP are typically active only under aerobic conditions, an anaerobically functional reporter was necessary to verify promoter activity under 1 atm $CO_2$. Therefore, both promoters were placed upstream of the lacZ reporter, which is O2-independent. Cultures of transformed strains SR7xL and SR7hL passaged under 1 atm $CO_2$ and induced with D-xylose and IPTG, respectively, were analyzed for LacZ production 24 hours after induction. Total protein-normalized LacZ specific activities (e.g., activity of enzyme per mg total protein; μmol min-1 mg-1; U/min) for duplicate lacZ strain cultures, empty vector controls, and a LacZ assay reagent (B-PER; Thermo Scientific; Waltham, Mass.) control are displayed in FIG. 22.

LacZ specific activity values from duplicate incubations of xylose-amended cultures of SR7xL (1.26-4.41 U/min) and SR7x (0.06-0.11 U/min) demonstrate that LacZ activity is increased by induction relative to empty vector controls. Relative to empty vector samples and the B-PER assay control (≤0.14 U/min), LacZ activity increased 9-32 fold. Differential expression of LacZ by IPTG induction of $P_{Hyper-spank}$ was also observed, but at lower total protein-normalized specific activity levels than by xylose-induction (0.31-1.36 U/min). LacZ production under aerobic and anaerobic 1 atm $CO_2$ conditions represents the first successful use of IPTG-inducible $P_{Hyper-spank}$ in *B. megaterium*. This development, and verification of strong $P_{Xyl}$ activity under 1 atm $CO_2$ expands the list of genetic tools available for SR7 engineering, as well as alternative *B. megaterium* strains used for biotechnological applications.

Figure 23:
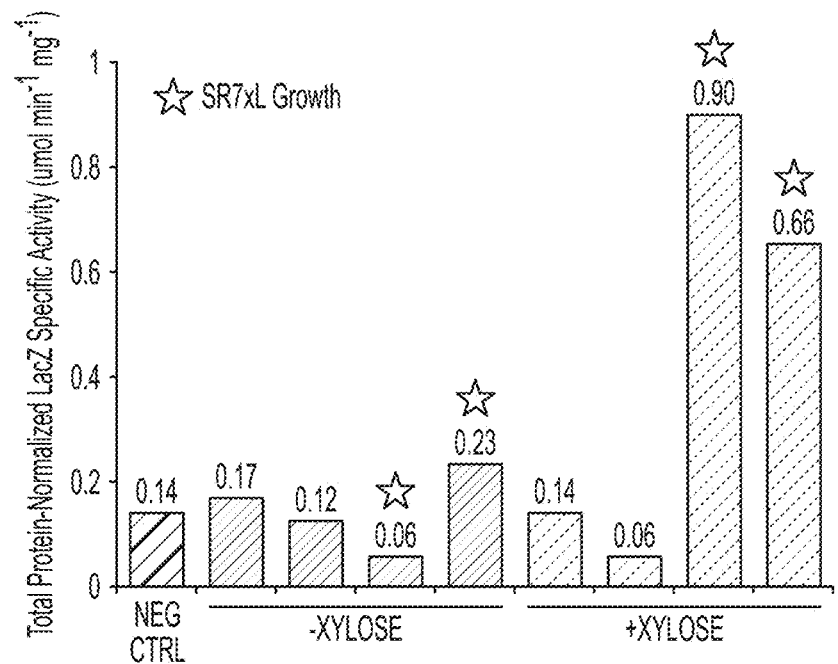
FIG. 23 shows LacZ-specific activity in $scCO_2$ cultures in the absence and presence of 0.5% xylose, with B-PER negative control. SR7xL cultures demonstrating robust growth are highlighted with stars. Cultures without stars germinated but did not demonstrate robust outgrowth.

After exhibiting superior total protein-normalized LacZ activity under 1 atm $CO_2$, the SR7xL strain was investigated for expression under $scCO_2$. Duplicate cultures with and without 0.4% xylose inducer demonstrated robust germination and growth after 21 days under $scCO_2$ conditions, with appearance of vegetative cell morphologies and at least 15-fold increase in cell counts relative to starting cultures. Duplicate cultures of induced and uninduced reactors showing vegetative cell morphologies, but not robust outgrowth (<10-fold increase in cell counts) were utilized for comparison of LacZ activity in germinated/low-level growth cultures. Both cultures that grew under $scCO_2$ in the presence of xylose showed elevated total protein-normalized LacZ specific activity (0.66-0.90 U/min) relative to uninduced cultures that grew (0.06-0.23 U/min) (FIG. 23). Uninduced cultures may display low-level LacZ activity due to minor leakiness of the xylose promoter, as also demonstrated under aerobic conditions. Duplicate induced cultures that did not grow but appeared to have germinated (by microscopy) displayed activity values (0.06-0.17 U/min) on par with the negative control (0.14 U/min), indicating that active growth is required for heterologous enzyme expression under $scCO_2$. Successful LacZ production by SR7 under $scCO_2$ was the first demonstration that exogenous gene expression in a $scCO_2$ headspace bioreactor is possible.

Engineering and Expression of a Heterologous Pathway for Biofuel Synthesis in $scCO_2$-Tolerant Strain SR7 Under Aerobic, 1 Atm $CO_2$ and $scCO_2$ Conditions The final two steps in the production of isobutanol using the valine biosynthesis pathway requires catalytic conversion of α-KIV to isobutyraldehyde by α-ketoisovalerate decarboxylase (KivD), followed by conversion to isobutanol by alcohol dehydrogenase (FIG. 19). Since the kivD gene is not present in the SR7 genome, it required exogenous introduction in order to be to be expressed. The well-described *Lactococcus lactis* version of keto-isovalerate decarboxylase commonly used for isobutyraldehyde production (de la Plaza et al., 2004) was utilized in this study. Though the SR7 genome indicates that the gene then required for conversion of isobutyraldehyde to isobutanol, alcohol dehydrogenase, is present in the cell, its production is likely lower than if transformed on a plasmid with a strong promoter. As a result, the *E. coli* version, adh6$_{Ec}$, was initially used in SR7 due to laboratory availability.

Figure 24:
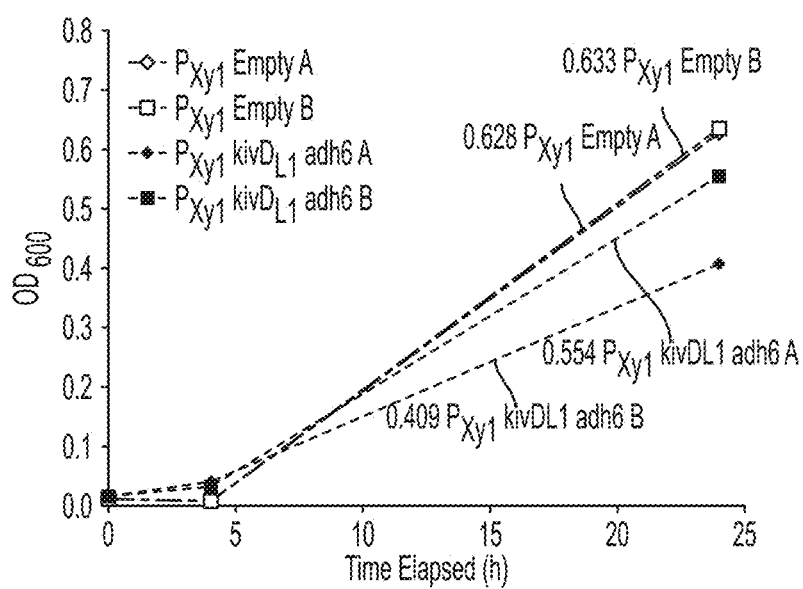
FIG. 24 shows growth of biofuel and empty vector control strains under 1 atm $CO_2$

While upstream optimization may enable efficient conversion of glucose to α-KIV, initial pathway engineering relied on an exogenous supply of α-KIV to constrain heterologous enzyme activity assays to the final two steps of the pathway. Because the isobutanol pathway genes should be functional under both anaerobic and aerobic conditions, induction of the final two steps was first characterized under aerobic and 1 atm $CO_2$ conditions to validate expression under both conditions. After demonstrating initial activity, subsequent screening for highly active alcohol dehydrogenase enzymes in SR7 under aerobic and 1 atm $CO_2$ ultimately enabled the use of an optimized construct under $scCO_2$. 1 atm $CO_2$ passaged cultures of strains SR7xKA6 and SR7x (empty vector control) in LB media grew similarly well 24 hours after gene expression was induced. Based on averaged $OD_{600}$ values, heterologous pathway expression appeared to impose a metabolic burden that results in a 24% decrease in biomass yield relative to the empty vector control (FIG. 24). GC-MS analysis verified production of several biofuel products in the 1 atm $CO_2$ cultures grown in LB after 4 and 24 hours, including expected compounds isobutyraldehyde and isobutanol (Table 16). In a somewhat surprising result, isopentanol and phenethyl alcohol were also produced, indicating that pJBxKA6 genes kivD$_{L1}$ and adh6$_{Sc}$ appear to redirect flux of alternative amino acid biosynthesis pathways, including those of leucine (to isopentanol) and phenylalanine (to phenethyl alcohol; FIG. 19). No biofuel peaks were detected in either of the $P_{Xyl}$ Empty replicate cultures.

The biofuel strain replicates (A & B) showed accumulation of the intermediate product isobutyraldehyde at the 4-hour time point (A: 1.34, B: 1.66 mM) with trace level accumulation of isobutanol (A & B: 0.01 mM) and isopentanol (A & B: 0.01 mM) and no detectable phenethyl alcohol (Table 16).

TABLE 16

Summary of bioproducts (mM, mg/l) generated by SR7xKA6 under 1 atm $CO_2$

| | | [Biofuel] (mM) | | | | | |
|---|---|---|---|---|---|---|---|
| Time | Replicate | Isobutyraldehyde | Isobutanol | Isopentanol | Phenethyl Alcohol | Sum | Culture Conditions |
| 4 | A | 1.66 | 0.01 | 0.01 | 0 | 1.69 | Supplemented α-IKV: 5 mM |
| 4 | B | 1.34 | 0.01 | 0.01 | 0 | 1.35 | Strain: SR7 $P_{Xyl}$ $kivD_{Ll}$ $Adh6_{Sc}$ |
| 24 | A | 1.7 | 4.00 | 1.95 | 0.22 | 7.87 | Media:LB + tet 0.1 ug/mL |
| 24 | B | 1.85 | 4.08 | 1.98 | 0.26 | 8.17 | Induced: 0.5% xylose |

| | | [Biofuel] (mg/L) | | | | | | Std Curve Conversion |
|---|---|---|---|---|---|---|---|---|
| Time | Replicate | Isobutyraldehyde | Isobutanol | Isopentanol | Phenethyl Alcohol | Sum | Compounds | y = counts; x = mM |
| 4 | A | 23.0 | 0.1 | 0.1 | 0.0 | 23.3 | Isobutyraldehyde | y = 27623x; R = 0.81 |
| 4 | B | 18.6 | 0.1 | 0.1 | 0.0 | 18.8 | Isobutanol | y = 169971x; R = 1.00 |
| 24 | A | 23.6 | 54.0 | 22.1 | 1.8 | 101.5 | Isopentanol | y = 184505x; R = 0.97 |
| 24 | B | 25.7 | 55.0 | 22.5 | 2.1 | 105.3 | Phenethyl Alcohol | y = 434871x; R = 1.00 |

A marked shift in production was observed in duplicate cultures at the 24-hour time point, with significant accumulation of isobutanol (A: 4.00, B: 4.08 mM), isopentanol (A: 1.95, B: 1.98 mM) and small amounts of phenethyl alcohol (A: 0.22, B: 0.26 mM), while maintaining comparable aldehyde accumulation (A: 1.70, B: 1.85 mM). It therefore appears that while a certain concentration of aldehyde will build up due to the limits of $Adh6_{Sc}$ activity in SR7, by 24 hours the majority of α-KIV substrate has been converted to final biofuel products isobutanol and isopentanol.

Figure 25:
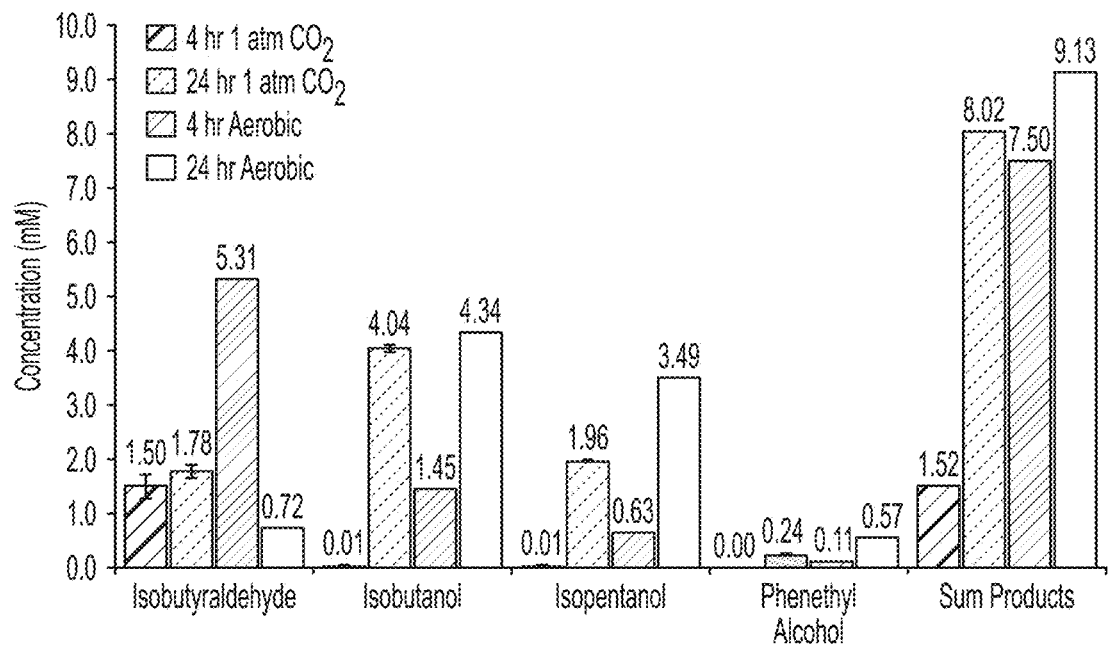
FIG. 25 shows SR7xKA6 bioproduct concentrations under 1 atm $CO_2$ and aerobic conditions 4 and 24 hours after induction. Bars, left to right: 4 hr 1 atm $CO_2$, 24 hr 1 atm $CO_2$, 4 hr Aerobic, and 24 hr Aerobic. Measurements of biofuel production from aerobically-incubated cultures may be underestimated due to the removal of caps during subsampling of aerobic cultures, which may have resulted in some volatile product losses.

1 atm $CO_2$ cultures of SR7xKA6 generated bioproducts at a slower rate than under aerobic conditions, but final 24-hour titers were similar under both conditions (FIG. 25), indicating reduced catalytic efficiency but comparable total substrate conversion. At 4 hours, the sum of 1 atm $CO_2$ bioproduct concentrations was 28% of the summed concentrations under aerobic conditions, increasing to 88% of the aerobic sum by 24 hours. Specifically with regard to isobutanol, by 24 hours the 1 atm $CO_2$ incubations generated 93% of the concentration detected in aerobic cultures. Overall, these results suggest that reduced production rates under 1 atm $CO_2$ relative to aerobic conditions may be due to slower microbial growth/metabolism or diminished enzyme activity.

While nearly identical amounts of isobutanol were produced under both aerobic and 1 atm $CO_2$ conditions, 1 atm $CO_2$ titers of isopentanol and phenethyl alcohol were about half as concentrated as under aerobic conditions. Therefore, it appears that alternative amino acid pathway enzymes (FIG. 19) may be operating at reduced efficiency in siphoning off α-KIV substrate, possibly due to dependence on $O_2$-dependent co-factor NAD(P)H.

Alcohol Dehydrogenase Screening

The accumulation of isobutyraldehyde in initial SR7xKA6 cultures under 1 atm $CO_2$ (Table 16, FIG. 25) prompted additional screening of alcohol dehydrogenase gene variants in order to improve the rate and completeness of isobutyraldehyde conversion to isobutanol. This enzymatic reaction is of particular importance in the proposed biofuel production system because isobutyraldehyde is soluble in $scCO_2$ and thus premature partitioning of accumulated isobutyraldehyde into the $scCO_2$ headspace would reduce overall yields, titers and purity of the desired isobutanol end product. Vectors constructed with PXyl kivDL1 alone and with one of five alcohol dehydrogenase variants (adh6Sc, adhABm, adhALL, adhPEc, and yqhDEc) were thus assayed for biofuel production under aerobic and 1 atm $CO_2$ conditions. Aerobic results for GC-MS detected compounds after 4 and 24 hours are presented in FIGS. 26A and 26B.

Results from subsequent alcohol dehydrogenase variant screens (including raw and OD-normalized values) under 1 atm $CO_2$ are presented in FIGS. 27A-27D.

Under aerobic conditions concentrations of aldehyde and alcohol products demonstrate that yqhDEc variant cultures (SR7xKY) outperformed all other alcohol dehydrogenases according to several metrics. By 4 hours, while all other variants generated isobutyraldehyde above 1.5 mM, SR7xKY cultures prevented intermediate accumulation by converting nearly all α-KIV substrate to isobutanol and isopentanol (FIG. 26A). By 24 hours, while all alcohol dehydrogenase variants had converted isobutyraldehyde to alcohol products, SR7xKY cultures generated the highest titers for both isobutanol (4.6 mM) and isopentanol (3.4 mM). Overall, $YqhD_{Ec}$ results in >90% conversion of α-KIV substrate to biofuel products (FIG. 26B).

Under 1 atm $CO_2$ isobutyraldehyde, isobutanol, and isopentanol concentrations were nearly identical for all strains at both 24 and 48 hours based on raw values (FIGS. 27A and 27C), suggesting that effectively all α-KIV substrate had been converted by 24 hours. The fact that low levels of isobutyraldehyde persist at both 24 and 48 hours also suggests that alcohol dehydrogenase activity may become limited once the aldehyde concentration drops below a threshold level, as all aldehyde concentrations from both time points fell within a narrow range, (0.193-0.457 mM; 0.014-0.033 g/l). The best performing enzyme variants after 24 and 48 hours as determined by maximum alcohol and minimum aldehyde concentrations are listed in Table 17.

TABLE 17

1 atm $CO_2$ alcohol dehydrogenase variant performance summary based

| | | [Isobutanol]$_{Max}$ | | | [Isopentanol]$_{Max}$ | | | [Isobutyraldehyde]$_{Min}$ | |
|---|---|---|---|---|---|---|---|---|---|
| Time (h) | Enzyme | mM | g/L | Enzyme | mM | g/L | Enzyme | mM | g/L |
| 24 | YqhD | 4.43 | 0.342 | Adh6$_{Sc}$ | 1.893 | 0.167 | YqhD | 0.193 | 0.014 |
| 48 | YqhD | 4.448 | 0.343 | Adh6$_{Sc}$ | 2.025 | 0.178 | AhdA | 0.203 | 0.015 |

OD-normalized product concentrations (FIGS. 27B and 27D) suggest that AdhA$_L$ may be especially efficient at product generation on a per-cell basis, which in addition to displaying the lowest aldehyde concentration at 48 hours indicates it may be one of the better performing variants. In addition to yqhD$_{Ec}$ strain SR7xKY demonstrating the fastest aldehyde conversion rates and highest final titers under aerobic conditions (FIG. 26), results from 1 atm $CO_2$ cultures also displayed the highest final titers (FIG. 27C), although performance differences under 1 atm $CO_2$ were marginal relative to aerobic results. With available data especially encouraging for variant YqhD$_{Ec}$, subsequent incubation experiments under sc$CO_2$ proceeded with the pJBxKY construct-bearing strain SR7xKY.

Bench Scale Abiotic Isobutanol sc$CO_2$ and Aqueous Phase Extractions

Figure 28A:
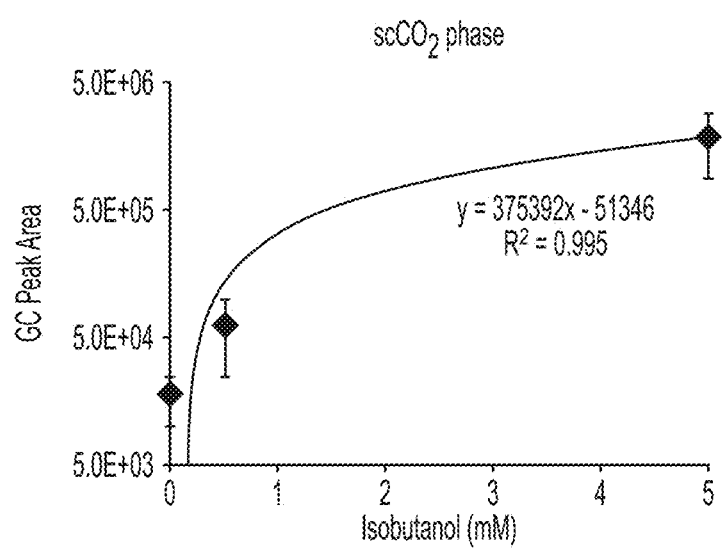
FIGS. 28A and 28B show standard curves based on abiotic $scCO_2$ phase (FIG. 28A) and aqueous phase extraction of isobutanol (FIG. 28B)
Figure 28B:
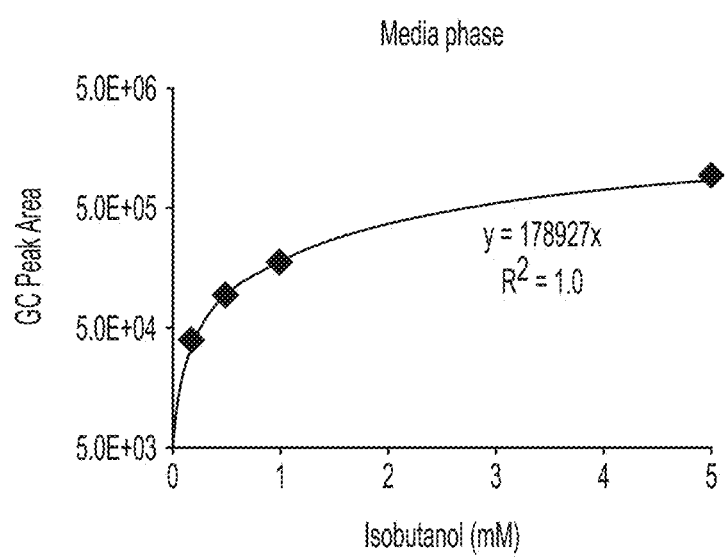

In situ extraction via sc$CO_2$ relies on the partitioning of a compound from the aqueous phase to the sc$CO_2$ phase followed by product recovery. After manifold modifications, batch reactors used for culturing under sc$CO_2$ in this study were utilized for bench scale in situ extraction, as described in the Methods. Standard curves generated for partitioning of isobutanol from aqueous media into the sc$CO_2$ phase demonstrated that isobutanol at concentrations from 0.5-5.0 mM (37-371 mg/l) could be quantitatively stripped from the media phase and recovered in the sc$CO_2$ phase (FIGS. 28A and 28B).

Process modifications including continuous reactor heating, increased depressurization rates and increased ethyl acetate solvent volume appeared to significantly improve supercritical $CO_2$ phase recovery efficiencies during a second round of abiotic isobutanol extractions, increasing the percent of total isobutanol recovered from the sc$CO_2$ phase by an order of magnitude from 2% to 20% between the initial and second runs. Overall mass balance calculations of the second run demonstrated that between 75-90% of loaded isobutanol concentration was recovered by the sum of aqueous and sc$CO_2$ phase products after three-day sc$CO_2$ incubations. Since the batch bioreactor set up used in this work is not optimized for solvent stripping using sc$CO_2$, 2-20% product recovery in sc$CO_2$ is satisfactory in the context of this study. However, further work to optimize the reactor and stripping configuration may enable more efficient in situ extraction.

Biosynthesis and In Situ Extraction of Natural Products and Biofuels Under sc$CO_2$ Having established alcohol dehydrogenase variant YqhD$_{Ec}$ as the best performing enzyme for isobutanol production, cultures loaded with spores of SR7xKY in the presence of xylose inducer were anticipated to generate biofuel products. Conversely, metabolically inactive cultures and LacZ-generating SR7xL control cultures were not expected to show signatures of alcohol production. Uninduced biofuel strain cultures showing growth were anticipated to generate low-level biofuel concentrations due to the mildly leaky nature of P$_{Xyl}$. A summary of growth outcomes from sc$CO_2$-incubated cultures of genetically modified strains and wild-type SR7 is presented in Table 18.

TABLE 18

Summary of growth outcomes for cultures of SR7 wild-type and modified strains in M9A+ media incubated under sc$CO_2$

| Inocula | ±Xylose | Starting spores/mL | M9A+ Growth Frequency | Max Biomass (cells/mL) |
|---|---|---|---|---|
| SR7xKY | + | $3 \times 10^5$ | 33% (5/15) | $5.96 \times 10^7$ |
| | − | $1 \times 10^5$ | 17% (1/6) | $2.88 \times 10^7$ |
| SR7xL | + | $5 \times 10^5$ | 13% (2/15) | $1.34 \times 10^7$ |
| | − | $3 \times 10^5$ | 33% (2/6) | $9.69 \times 10^6$ |
| Wild-type SR7 | − | $3 \times 10^4$ | 64% (16/25) | $1.63 \times 10^7$ |
| Media Control | + | b.d. | b.d. | b.d. |

Decreased growth frequencies observed in transformed strains relative to wild-type SR7 may indicate a metabolic burden associated with carrying and expressing the pRBBm34 vector, as observed under 1 atm $CO_2$ (FIG. 24), that reduces germination frequency and/or vegetative outgrowth, though these hypotheses will require additional investigation.

Figure 29A:
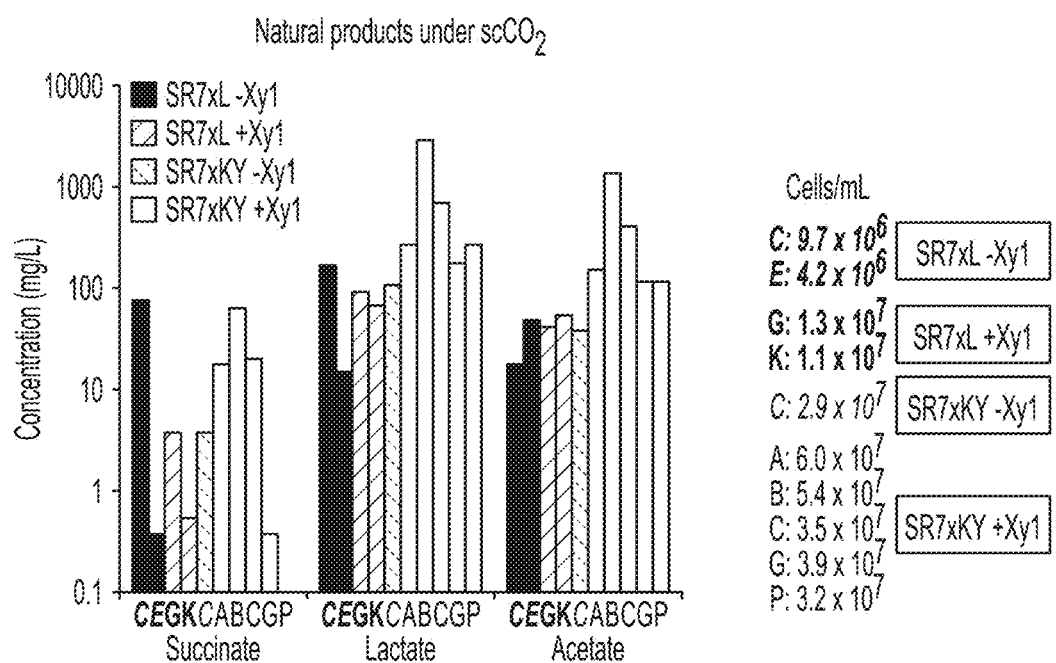
FIGS. 29A to 29B show natural fermentative products generated by SR7xL and SR7xKY cultures under $scCO_2$ showing growth, as detected by HPLC.
Figure 29B:
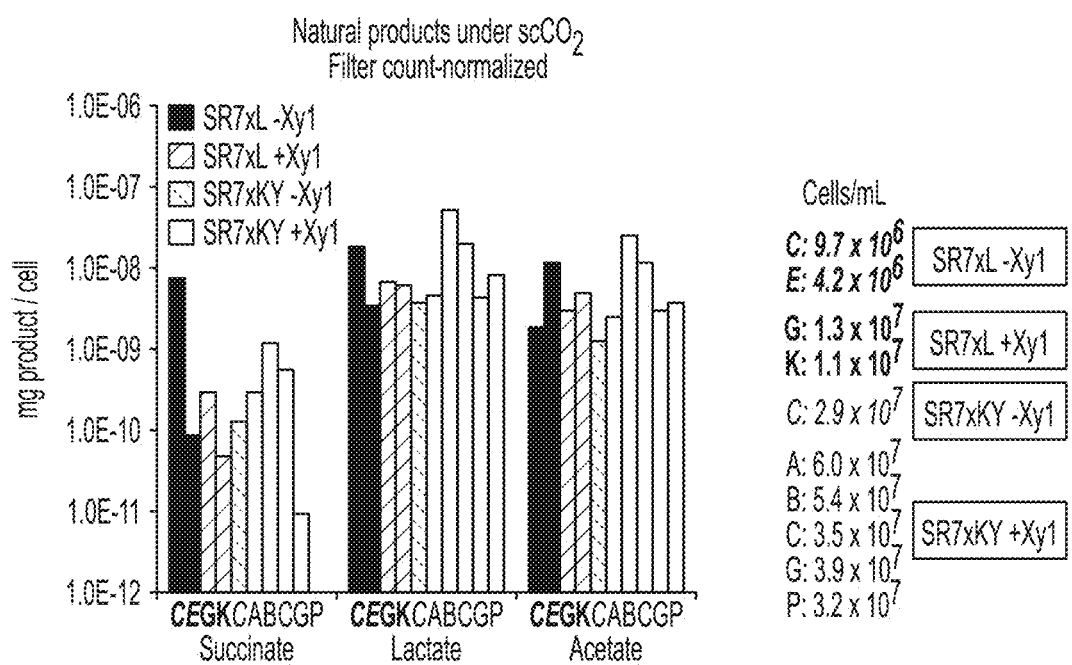

Natural fermentation products were detected by HPLC in the media phase of all reactors demonstrating growth (>10-fold increase in cell counts) over 21-22 day sc$CO_2$ incubations, including induced and uninduced cultures of both SR7xL and SR7xKY. Detected compounds were consistent with those generated by wild-type SR7 sc$CO_2$ cultures (Example 1), including succinate (up to 73.2 mg/l), lactate (up to 2.8 g/l), and acetate (up to 1.3 g/l) (FIGS. 29A and 29B), which reinforces the suggestion of growth via the TCA Cycle and mixed acid fermentation. Total cell-normalized metabolite concentrations demonstrate maximum per cell productivities of $7.6 \times 10^{-9}$, $5.3 \times 10^{-8}$, and $2.5 \times 10^{-8}$ mg product cell$^{-1}$ for succinate, lactate and acetate, respectively, which are also similar to maximum per cell productivities of the wild-type strain under 1 atm $CO_2$ and sc$CO_2$ (Example 1). The quantification of natural metabolites thus has potential for use as an indicator of active growth under sc$CO_2$.

Figure 30A:
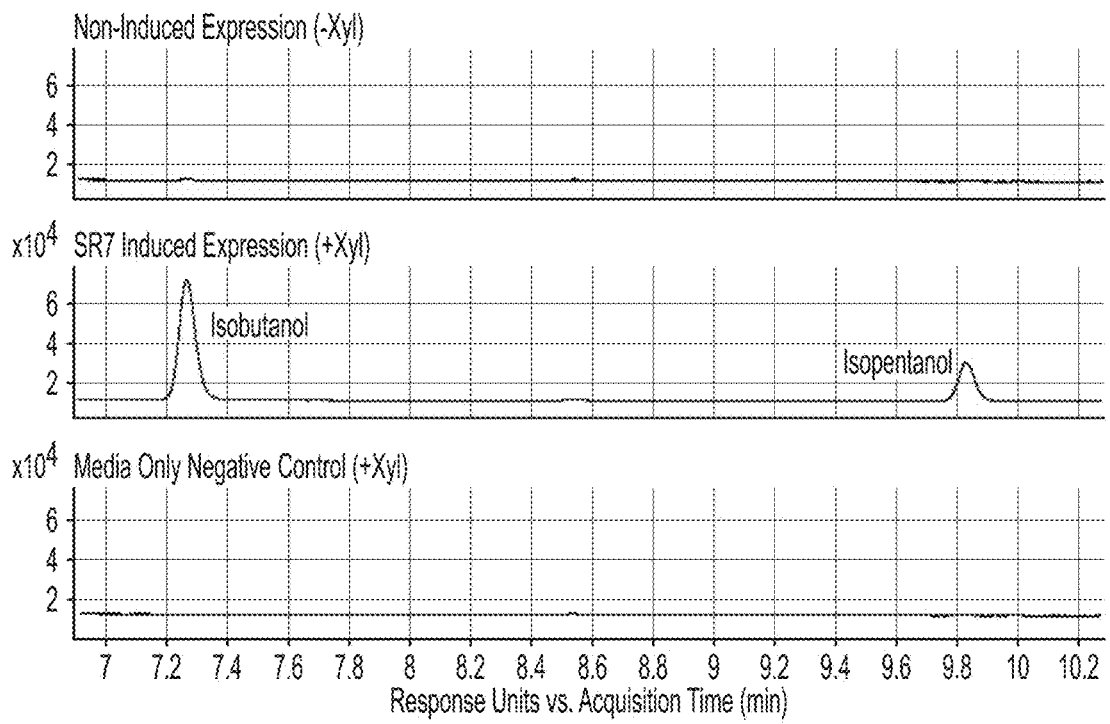
FIGS. 30A to 30B show examples of GC-FID traces detecting biofuel products isobutanol and isopentanol in the media phase (FIG. 30A) and $scCO_2$-extracted phase (FIG. 30B) of $scCO_2$-incubated SR7xKY cultures.
Figure 30B:
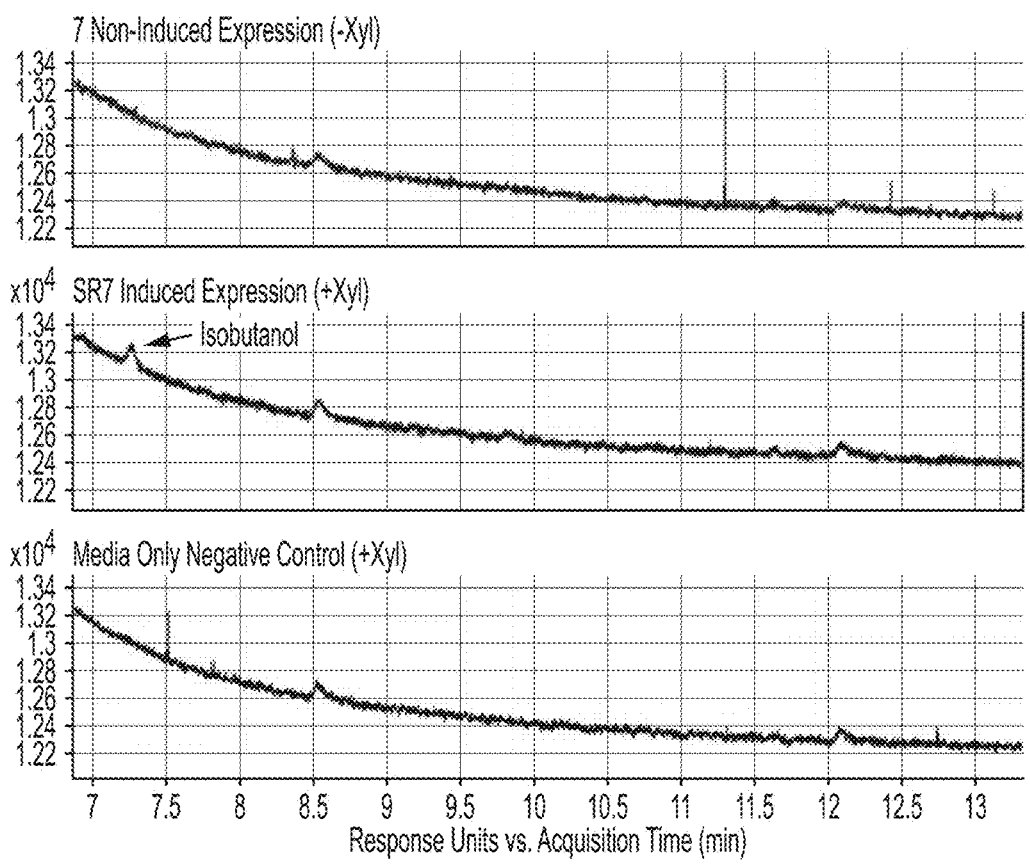
Figure 31:
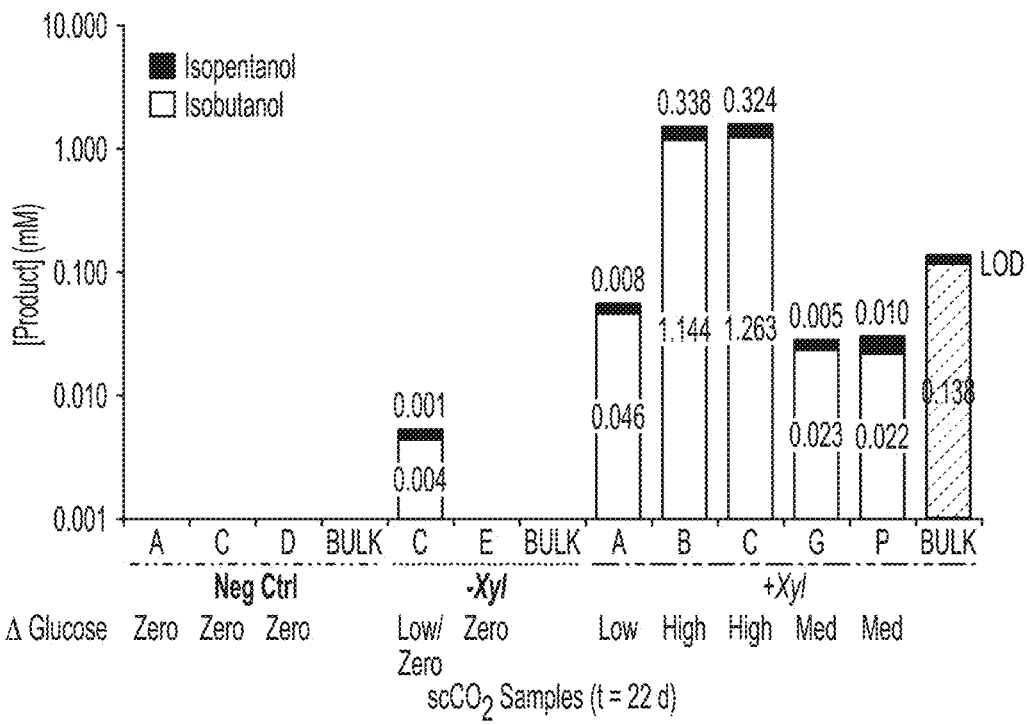
FIG. 31 shows recovered bioproduct concentrations from cultures showing growth in xylose-induced and uninduced cultures, and media only negative controls. "Bulk" refers to $scCO_2$ phase-extracted headspace volumes from all induced, uninduced, or negative control reactors. Glucose consumption designated as zero, low/zero (0-5% consumed), low (5-20%), medium (20-40%), and high (>40%). "LOD"=limit of detection for $scCO_2$-extracted isobutanol (0.13 mM). Isobutanol is shown for each culture in gray bars; and isopentanol is shown in white above the isobutanol bars. Independent replicates are identified by the letter beneath each column.

Biofuels were detected by GC-MS in the media phase of all five reactors loaded with SR7xKY that showed growth and were induced with xylose (FIGS. 30A, 30B, and 31; Table 5). Of the two SR7xKY cultures showing growth in the absence of xylose, one showed low level biofuel production (0.3 mg/l isobutanol, 0.1 mg/l isopentanol), putatively as the result of the mildly leaky xylose promoter. No biofuel was generated in any of the reactors that did not show vegetative growth, verifying that metabolic activity (e.g., growth) under sc$CO_2$ is required for heterologous compound production (e.g., FIG. 23). No biofuels were detected in SR7xL cultures or media only negative controls.

Measured isobutanol concentrations in the aqueous phase of induced cultures ranged from 1.6 to 93.5 mg/l, while isopentanol concentrations varied from 0.5 to 29.7 mg/l. Observed maximum titers of 0.094 g/l isobutanol and 0.030 g/l isopentanol in scCO$_2$ incubations are approximately two orders of magnitude lower than under 1 atm CO$_2$, possibly due to reduced growth rates and biomass accumulation, or potential redirection of carbon flux under scCO$_2$ conditions.

In order to maximize direct scCO$_2$ phase biofuel compound recovery, all reactors loaded with strain SR7xKY that were induced were depressurized into a single collection solvent to maximize the likelihood of biofuel recovery. Similarly, all reactors loaded with SR7xKY that were uninduced were pooled via a single collection solvent. A pronounced GC-MS peak for isobutanol was observed only for the pooled samples from induced reactors while no isobutanol peak was observed from non-induced samples, indicating inducible gene expression led to biofuel generation under scCO$_2$ (FIGS. 30B and 31). Based on the abiotic scCO$_2$-extracted isobutanol standard curve (FIG. 28), the total scCO$_2$ phase isobutanol concentration was 10.2 mg per liter of media (0.138 mM; Table 19), which represents 5.2% of the total recovered isobutanol from both the media and scCO$_2$ phases. The detection of biogenic isobutanol in the scCO$_2$ phase represents the first biofuel production under scCO$_2$ conditions, as well as the first harvesting of biofuels from microbial cultures incubated under scCO$_2$.

Figure 26D:
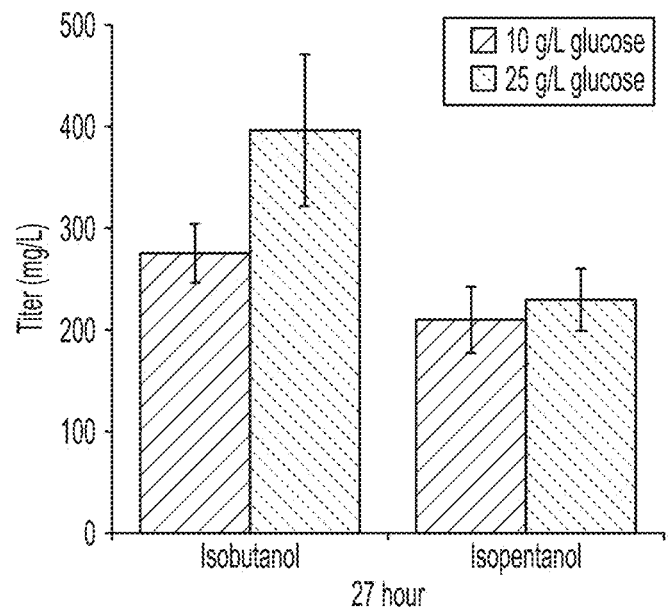
Figure 27A:
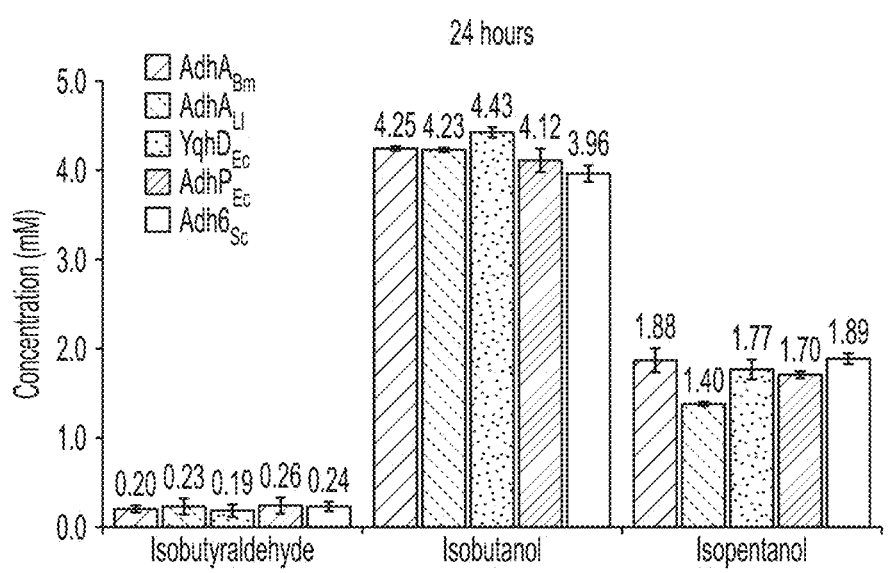
FIGS. 27A-27D show bioproduct concentrations generated under 1 atm $CO_2$ by SR7 PXyl kivDL1 in tandem with five alcohol dehydrogenase variants at 24 hours presented as raw (FIG. 27A), OD-normalized values (FIG. 27B), 48 hours as raw (FIG. 27C) and OD-normalized values (FIG. 27D). From left to right: $AdhA_{Bm}$, $AdhA_{L1}$, $YqhD_{Ec}$, $AdhP_{Ec}$, $Adh6_{Sc}$.
Figure 27B:
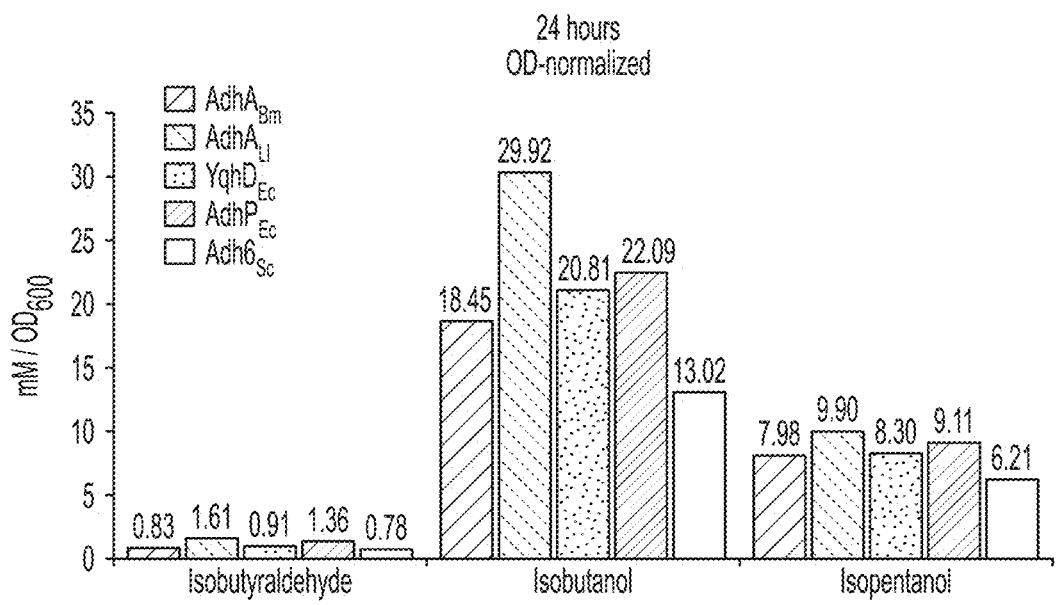
Figure 27C:
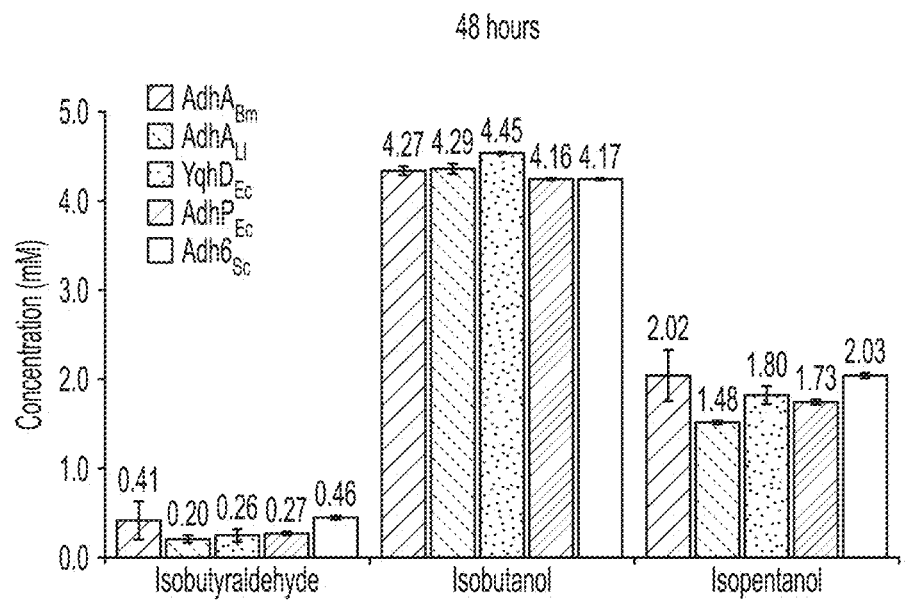
Figure 27D:
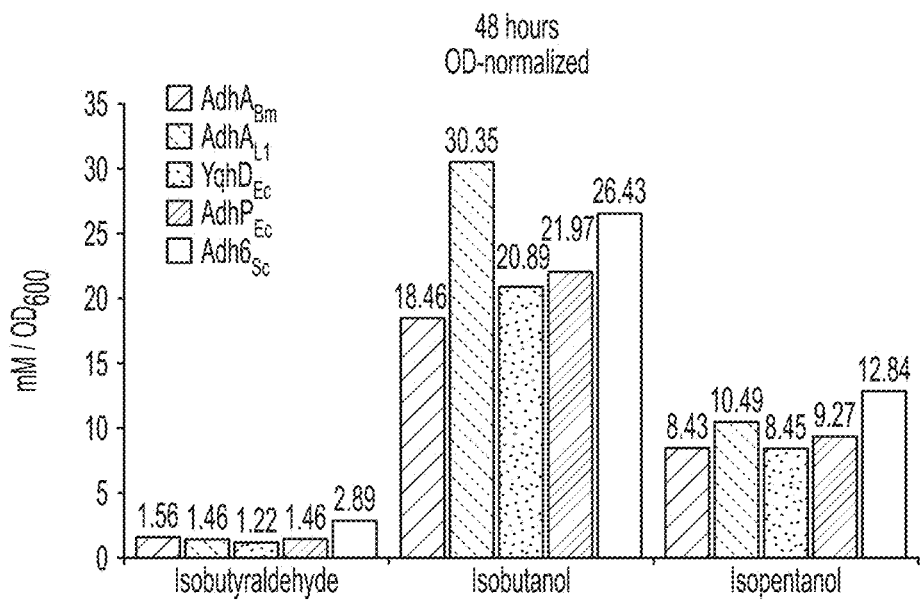

After regenerating the full isobutanol pathway to include ribosome binding sites for each individual gene of the pathway, observed production titers included approximately 275 mg/L for isobutanol and 200 mg/L for isopentanol (FIG. 26D). Further, after additional glucose was supplied to 25 g/L, isobutanol titers reached almost 400 mg/L (FIG. 26D). Inclusion of this pathway in SR7 shows the potential for this organism to make biofuel from low-cost, common substrates such as glucose as well as begins the metabolic engineering of this host to make a variety of products.

Example 3: Continuous Butanol Extraction Using Supercritical CO$_2$

Butanol is an example of a potentially valuable bioproduct that may be produced using the methods and cells described herein. Butanol can be used as a drop-in biofuel or as a fuel additive that can be blended with gasoline at much higher proportions than ethanol. To date, economical production of butanol has been hampered largely by its cytotoxicity, which becomes limiting at levels as low as several weight percent. Compared to other butanol recovery approaches, scCO$_2$-extraction has sterilization and potential

TABLE 19

Summary of scCO$_2$-incubation outcomes for SR7xKY-loaded columns that showed increased biomass relative to starting concentrations

| Culture Sample | Induced (+Xyl) | Replicate | Filter Count (cells/mL) | Filter Std Dev | Fold Growth [t22]/[t0] | [Glucose] (g/L) | Isobutanol (IBuOH) GC Area | mM | mg/L | Isopentanol (IPnOH) GC Area | mM | mg/L | Sum [Biofuel] mg/L |
|---|---|---|---|---|---|---|---|---|---|---|---|---|---|
| Cell-Free M9A + Control | Yes | A | 0.00E+00 | 0.00E+00 | 0 | 3.21 | 0 | 0 | 0 | 0 | 0 | 0 | 0 |
|  | C | 0.00E+00 | 0.00E+00 | 0 | 3.14 | 0 | 0 | 0 | 0 | 0 | 0 | 0 |
|  | D | 0.00E+00 | 0.00E+00 | 0 | 3.10 | 0 | 0 | 0 | 0 | 0 | 0 | 0 |
|  |  |  | Bulk (scCO$_2$) |  |  | 0 | 0 | 0 | 0 | 0 | 0 | 0 |
| SR7xKY | No | C | 2.88E+07 | 8.13E+06 | 195.3 | 3.05 | 765 | 0.004 | 0.316 | 239 | 0.001 | 0.094 | 0.411 |
|  |  | E | 4.36E+05 | 3.68E+05 | 3.0 | 3.14 | 0 | 0.000 | 0.000 | 0 | 0.000 | 0.000 | 0.000 |
|  |  |  | Bulk (scCO$_2$) |  |  | 0 | 0 | 0 | 0 | 0 | 0 | 0 |
|  | Yes | A | 5.96E+07 | 1.66E+07 | 190.0 | 2.45 | 8229 | 0.046 | 3.403 | 1698 | 0.008 | 0.669 | 4.072 |
|  |  | B | 5.37E+07 | 1.01E+07 | 171.3 | 0.01 | 204775 | 1.144 | 84.690 | 75485 | 0.338 | 29.745 | 114.435 |
|  |  | C | 3.48E+07 | 6.73E+06 | 111.0 | 1.91 | 225969 | 1.263 | 93.455 | 72353 | 0.324 | 28.511 | 121.966 |
|  |  | G | 3.88E+07 | 9.54E+06 | 123.5 | 2.70 | 4146 | 0.023 | 1.715 | 1181 | 0.005 | 0.465 | 2.180 |
|  |  | P | 3.18E+07 | 1.91E+05 | 101.5 | 2.60 | 3922 | 0.022 | 1.622 | 2126 | 0.010 | 0.838 | 2.460 |
|  |  |  | Bulk (scCO$_2$) |  |  | 563 | 0.138 | 10.212 | 0 | 0 | 0 | 10.212 |

In addition to endogenous metabolites and heterologous biofuels, differentially extracted compounds present in the bulk scCO$_2$ phase of grown cultures that are absent in the aqueous phase may hold promise as SR7 natural products able to be extracted by the scCO$_2$ phase. If these products can be identified, it is possible that optimization of product-generating pathways may enable future production and extraction of these unknown compounds. Peaks differentially present in the scCO$_2$ bulk phase include compounds with retention times of 19.75, 25.34, 25.4, and 26.97 minutes, however the these compounds were not identified.

Full Isobutanol Pathway

Due to the endogenous ability of SR7 to produce α-KIV, conversion to isobutanol and isopentanol was observed for just the keto-isovalerate decarboxylase and alcohol dehydrogenase containing cells (pXyl KivD, ADH6 and pXyl KivD, YqhD), with titers of approximately 125 mg/L for isobutanol and 175 mg/L for isopentanol when feeding 10 g/L glucose. The addition of the valine synthesis operons from E. coli did not show any increased production suggesting that the operons were not correctly transcribed in SR7 or at least one of the pathway enzymes was not functional in SR7.

energy balance advantages. Because scCO$_2$ selectively extracts butanol instead of water, a highly concentrated butanol stream can be recovered which requires minimal post-processing purification.

Specifically, butanol extraction performance was evaluated, initially using a batch-wise extraction to study the effects of initial butanol concentration, extraction vessel pressure, and scCO$_2$ volumetric flow rate on butanol extraction rate. Additionally, the data was modeled using a standard liquid-liquid mass transfer model to determine the values for the mass transfer coefficient, $\kappa_\alpha$. In all cases tested, the mass transfer model adequately described the experimental data. Best-fit values of $\kappa_\alpha$ did not vary within our estimated limits of uncertainty for variation in extraction pressure (from 10.3 to 13.7 MPa—the range over which the scCO$_2$-tolerant bacterial strain has exhibited growth); therefore it was determined that operation at lower pressures should be favored to achieve better process economy. Similar analysis was performed to interpret the mass transfer coefficient from correlations developed for gas-liquid and liquid-liquid extraction and compared to interfacial area results obtained from scCO$_2$-droplet size analysis.

Figure 32:
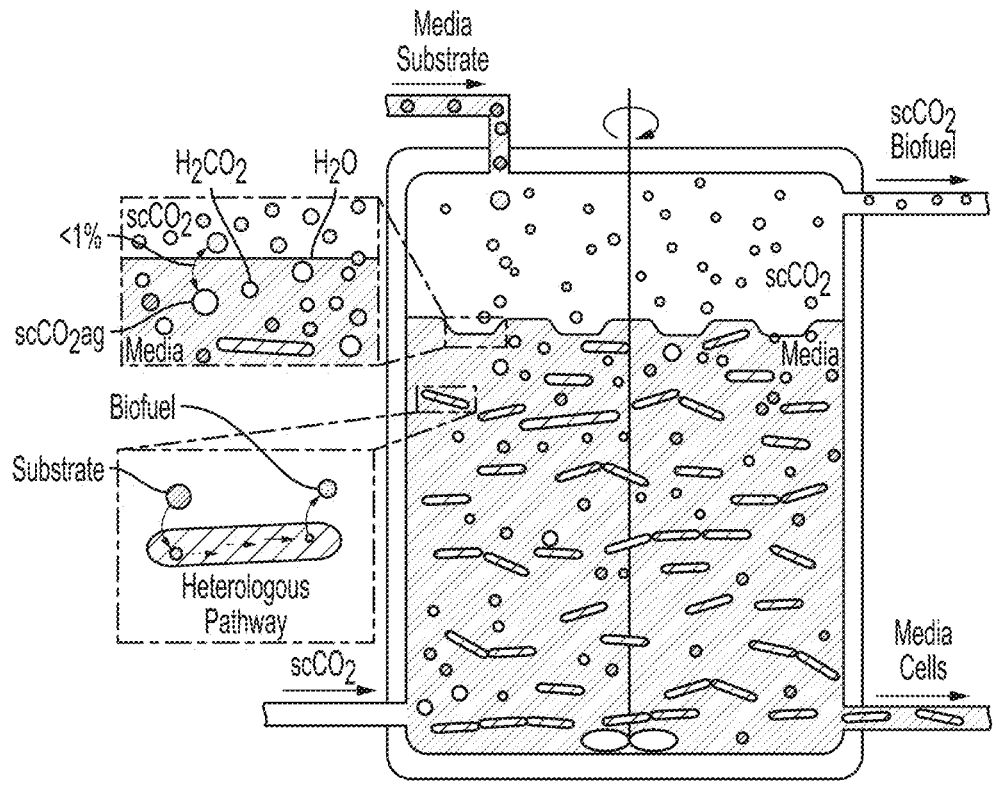
FIG. 32 shows a schematic of an example of a continuously $CO_2$-stripped bioreactor. The reactor includes two distinct phases: a $scCO_2$ phase and a media phase containing the cells producing the bioproduct (e.g., biofuels). The media/substrate and $scCO_2$ are continuously provided to the reactor, and $scCO_2$, bioproducts, media, and cells are removed.

A diagram of an example continuously $CO_2$-stripped multiphase reactor that may be used in the methods described herein is presented in FIG. 32. Briefly, use of $scCO_2$ provides a number of benefits to the system and allows for the continuous production and stripping of the bioproduct when the bioproduct is present in the solvent ($scCO_2$) phase of the reactor. Stripping the bioproduct may maintain a low concentration of the bioproduct in the reactor and alleviate end product toxicity.

Figure 38A:
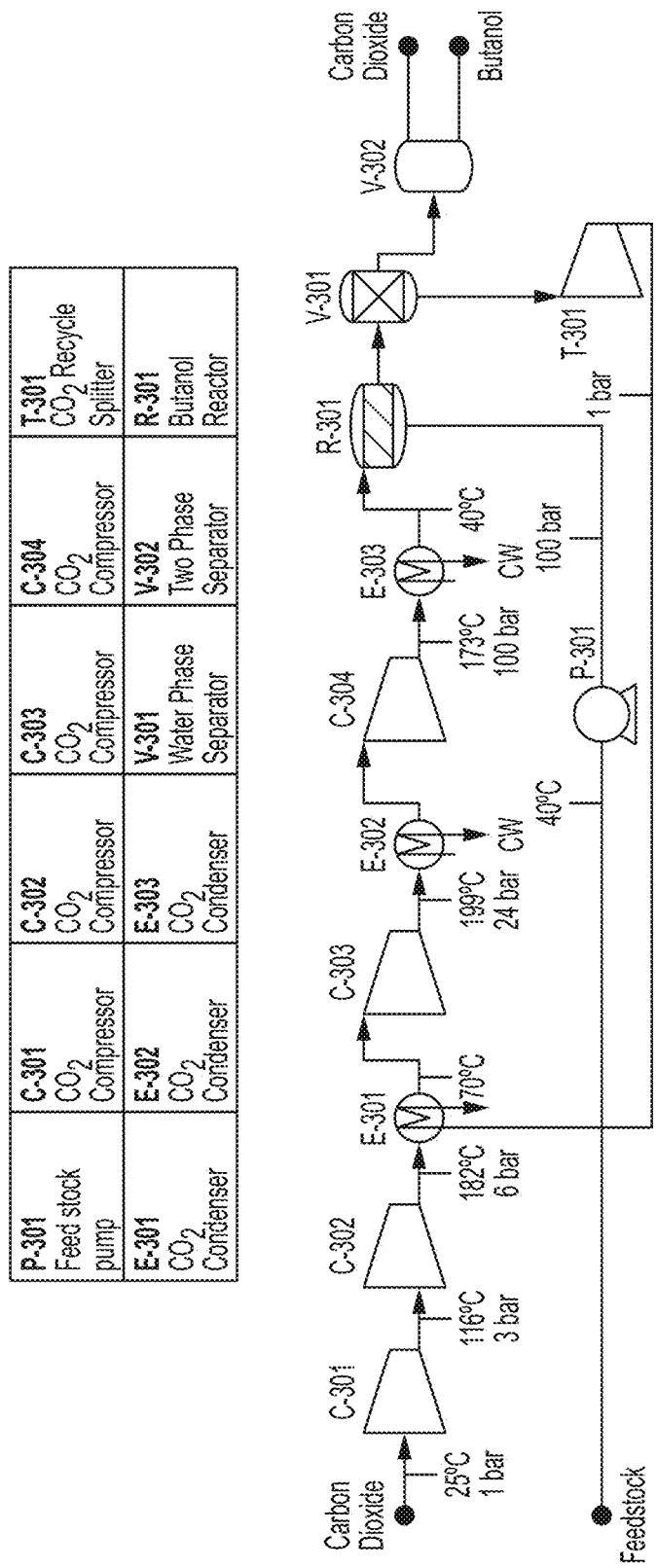
FIGS. 38A and 38B show energy demand for butanol extraction.
Figure 38B:
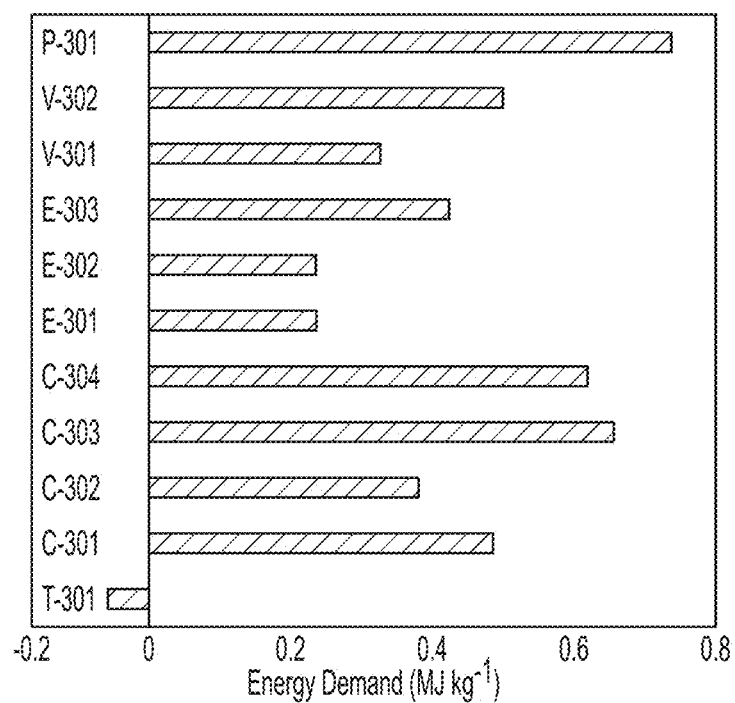

Specifically, FIG. 38A shows compression of $CO_2$ to liquid, near-critical or supercritical state (here, 100 bar and 40° C.), feeding it to a fermenter producing butanol for extraction, then recovery by de-pressurization. Table 20 provides performance metrics for the extraction process, including energy requirement and butanol purity. The data in Table 20 were calculated using thermodynamic efficiencies of 90% and mechanical efficiency of 30%, as is typical. The purity can be increased by additional steps. FIG. 38B provides energy requirements for the operations in the overall process. $CO_2$ compression represents the main energy requirement (C301, C302, and C303). Heat exchange, especially to cool $CO_2$ during stage-wise compression, is the next most significant energy requirement (E301, E302, and E303, as well as V301 and V302). Turbine expansion (T-301) partially offsets the compression energy.

TABLE 20

Performance metrics for extraction process

| | |
|---|---|
| Mass % Butanol in Product | 96.0% |
| Butanol Energy Requirement (MJ/kg) | 3-2 |
| Butanol recovery | 97.8% |

Such an example reactor was used to study higher alcohol (e.g., 1-butanol, n-butanol, pentanol, hexanol) extraction using $scCO_2$ and provided a simple mass transfer model of extraction. Extraction of the bioproducts using multiphase reactors, such as the reactor presented in FIG. 32, allows for dynamic extraction by flowing the $scCO_2$ phase and a non-flowing aqueous (media) phase. The conditions used in the experiments were focused on 100 bar and 40° C., conditions in which *B. megaterium* SR7 is capable of growing. Both the alcohol bioproduct and the rate of extraction were varied between experiments.

Figure 33:
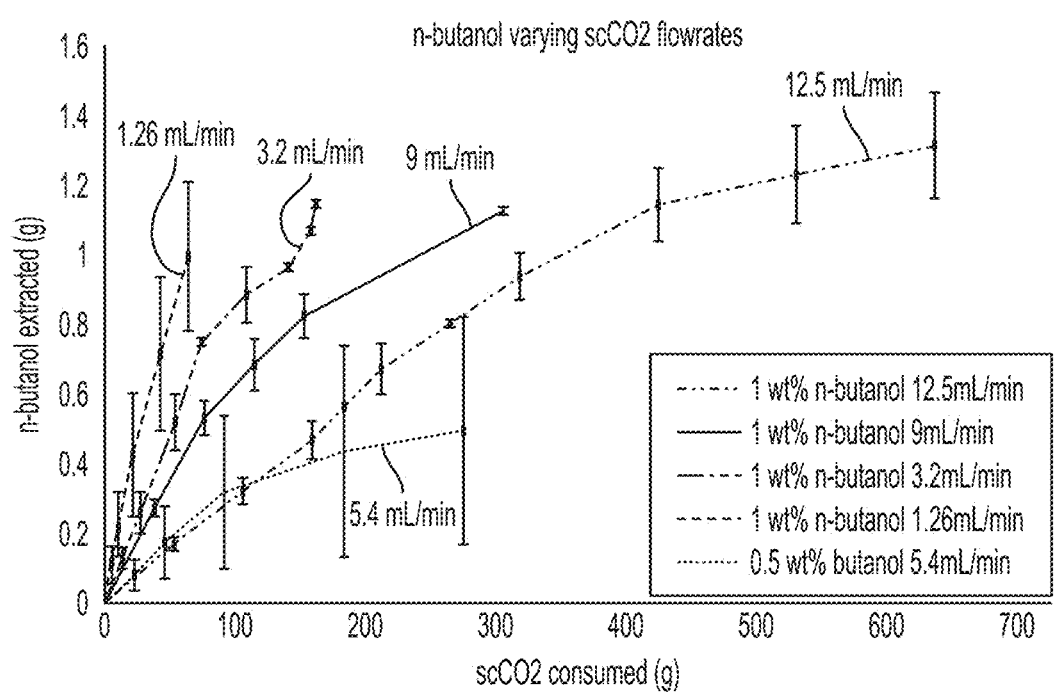
FIG. 33 presents n-butanol extraction profiles at varying $scCO_2$ flow rates (12.5 mL/min, 9 mL/min, 5.4 mL/min, 3.2 mL/min, and 1.26 mL/min).
Figure 34:
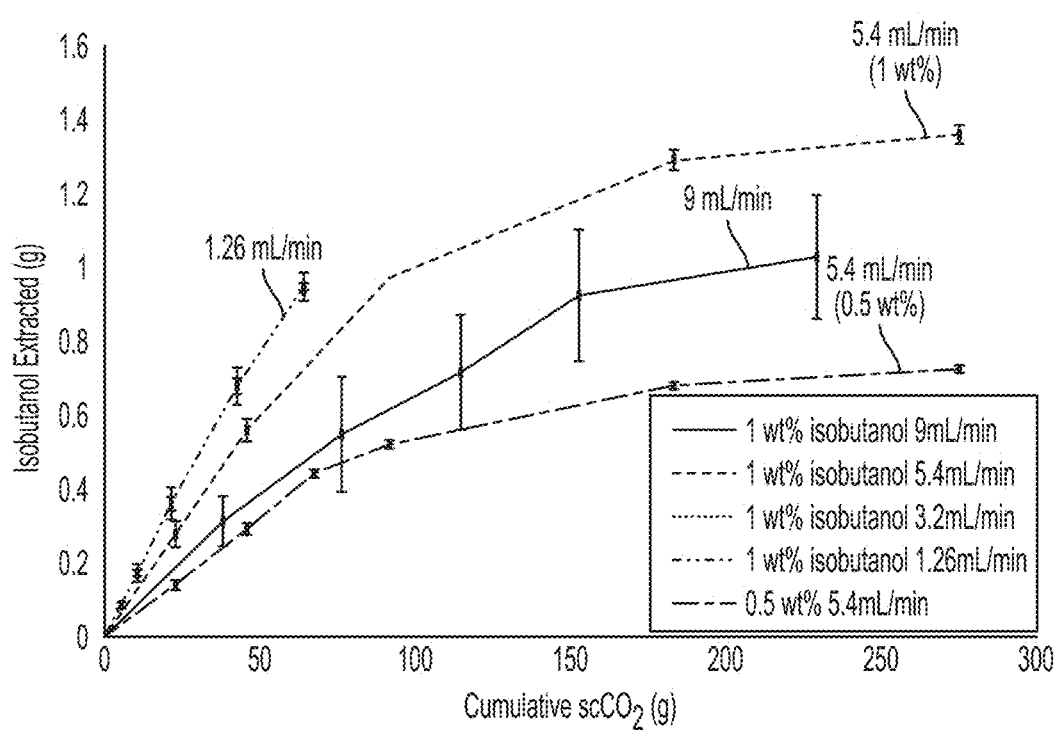
FIG. 34 presents isobutanol extraction profiles at varying $scCO_2$ flow rates (9 mL/min, 5.4 mL/min, 3.2 mL/min, and 1.26 mL/min).
Figure 35:
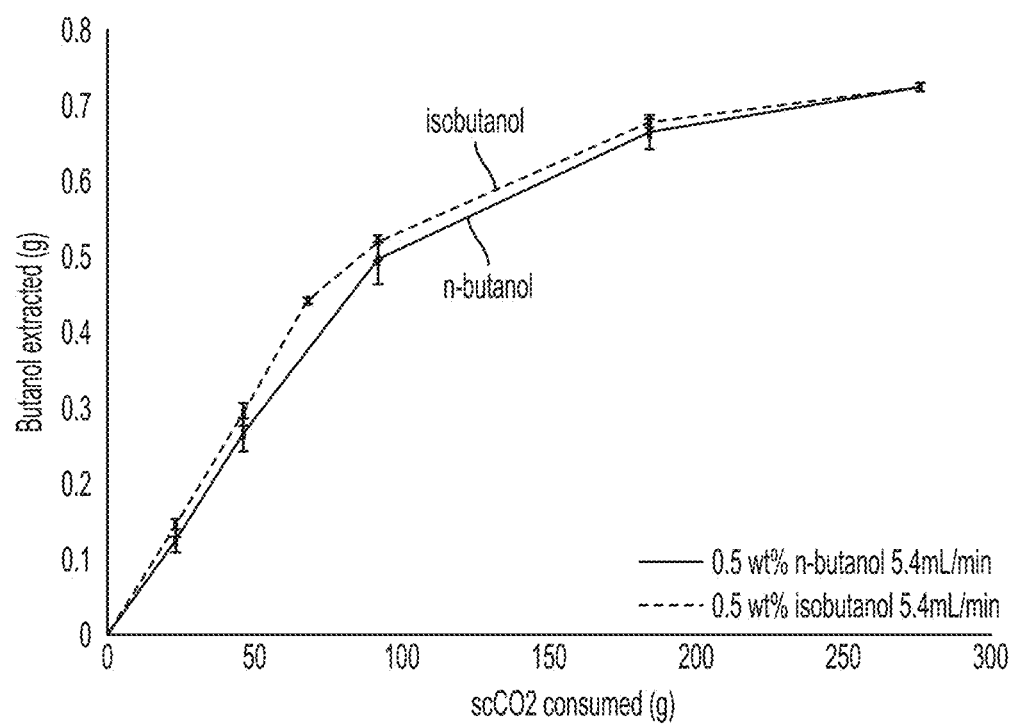
FIG. 35 is a graph comparing the n-butanol extraction profile to the isobutanol extraction profile using a $scCO_2$ flow rate of 5.4 mL/min.

The results of the extraction experiments for n-butanol, isobutanol, n-pentanol, n-hexanol, are presented in FIGS. 33, 34, 36, and 37, respectively. Briefly, for n-butanol and isobutanol, a slow rate of extraction was found to be most efficient (FIGS. 33 and 34). The fast flow rate (12.5 mL/min) resulted in extraction of the most butanol, whereas the 5.4 mL/min rate extracted the most isobutanol. Overlaying the extraction profiles for n-butanol and isobutanol shows that $scCO_2$ extraction of the two bioproducts occurs at the same rate at 5.4 mL/min $scCO_2$ (FIG. 35).

Figure 36:
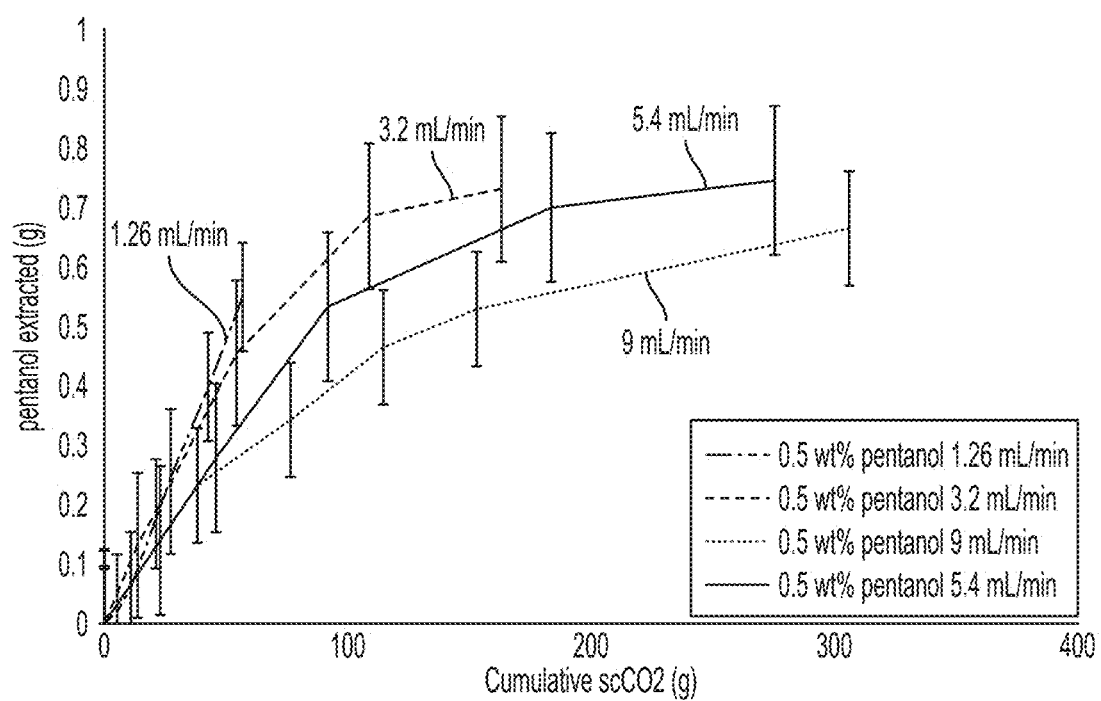
FIG. 36 presents n-pentanol extraction profiles at varying $scCO_2$ flow rates (9 mL/min, 5.4 mL/min, 3.2 mL/min, and 1.26 mL/min).
Figure 37:
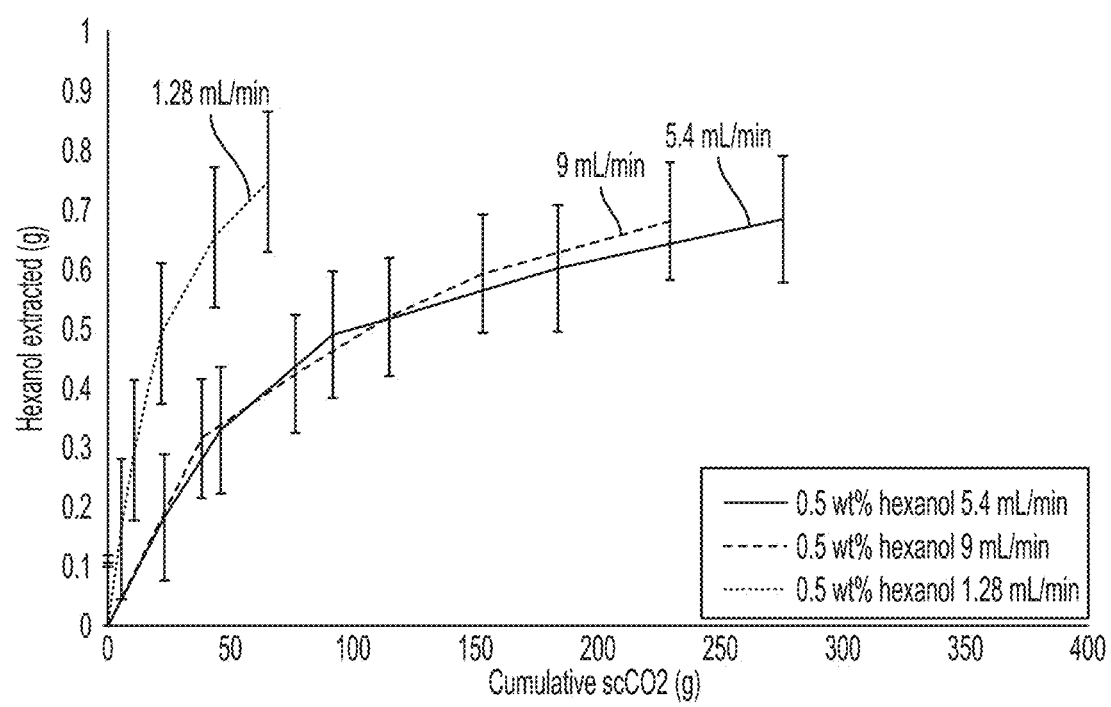
FIG. 37 presents n-hexanol extraction profiles at varying $scCO_2$ flow rates (9 mL/min, 5.4 mL/min, and 1.28 mL/min).

For n-pentanol, the 3.2 mL/min $scCO_2$ flow rate resulted in the superior extraction, whereas the extraction trends declined with increasing flow rates above 3.2 mL/min (FIG. 36). For n-hexanol, it was observed that increasing the $scCO_2$ flow rate above 5.4 mL/min did not increase the extraction rate (FIG. 37).

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. A method of producing a bioproduct, comprising culturing a cell in a multiphase reactor comprising an aqueous phase and a solvent phase, wherein the solvent phase comprises supercritical $CO_2$ (sc$CO_2$), near critical $CO_2$, or liquid $CO_2$, wherein the bioproduct is selected from the group consisting of isobutanol, butanol, isopentanol, phenyl-ethyl-alcohol and 4-methyl-pentanol; and/or wherein the bioproduct is a hydrocarbon, oxygenated hydrocarbon, aldehyde, alcohol, fatty acid, or ketone.

2. The method of claim 1, wherein
   (a) the cell is a viable cell;
   (b) the cell is a bacterial cell;
   (c) the cell is in spore-form or has been acclimated to sc$CO_2$, optionally wherein the cell has been acclimated to sc$CO_2$ by previous exposure to sc$CO_2$; and/or
   (d) the cell is engineered to recombinantly express one or more genes.

3. The method of claim 2, wherein the bacterial cell is resistant to sc$CO_2$ and/or the bacterial cell is a spore-forming bacterium belonging to the genus *Firmicutes*, optionally wherein the bacterial cell is a *Bacillus* spp, optionally selected from the group consisting of *Bacillus cereus*, *Bacillus subterraneus*, *Bacillus amyloliquefaciens*, *Bacillus safensis*, and *Bacillus megaterium*, optionally *Bacillus megaterium* SR7.

4. The method of claim 1, wherein the bioproduct is partitioned into the sc$CO_2$, near critical $CO_2$, or liquid $CO_2$ and/or wherein the bioproduct is isolated from the solvent phase and/or the aqueous phase.

5. The method of claim 1, wherein the bioproduct is isobutanol and the cell is engineered to recombinantly express an isoketovalerate decarboxylase and an alcohol dehydrogenase; optionally, wherein the isoketovalerate decarboxylase is a *Lactococcus lactis* gene and/or wherein the alcohol dehydrogenase is an *E. coli* gene.

6. The method of claim 1, wherein the bioproduct is 4-methyl-pentanol and the cell is engineered to recombinantly express one or more enzymes selected from the group consisting of an acetolactate synthase, a ketol-acid reductoisomerase, a dihydroxy-acid dehydratase, an alpha-ketoisovalerate decarboxylase, an aldehyde dehydrogenase, a propionyl-CoA transferase, a beta-keto-thiolase, a beta-keto-acyl-CoA reductase, an enoyl-CoA hydratase, a trans-enoyl-CoA reductase, a carboxylic acid reductase, a 4'-phosphopantenheinyl transferase, and an alcohol dehydrogenase.

7. The method of claim 1, wherein the solvent phase further comprises less than or equal to about 3% inert helium, and/or wherein the aqueous phase comprises a growth media, optionally wherein the growth media comprises a spore germination inducer that is optionally D-alanine.

8. The method of claim 1, wherein the culturing comprises incubating the cell in the multiphase reactor for at least 5 hours and/or the culturing comprises incubating the cell in the multiphase reaction at a temperature between 35° C.-40° C.

* * * * *